US008618119B2

(12) United States Patent
Nell et al.

(10) Patent No.: US 8,618,119 B2
(45) Date of Patent: Dec. 31, 2013

(54) FUSED CYANOPYRIDINES AND THE USE THEREOF

(75) Inventors: Peter Nell, Wuppertal (DE); Alexandros Vakalopoulos, Hilden (DE); Frank Süßmeier, Wuppertal (DE); Barbara Albrecht-Küpper, Wülfrath (DE); Katja Zimmermann, Düsseldorf (DE); Joerg Keldenich, Wuppertal (DE); Daniel Meibom, Leverkusen (DE)

(73) Assignee: Bayer Intellectual Property GmbH, Monheim (DE)

( * ) Notice: Subject to any disclaimer, the term of this patent is extended or adjusted under 35 U.S.C. 154(b) by 338 days.

(21) Appl. No.: 12/809,688

(22) PCT Filed: Dec. 9, 2008

(86) PCT No.: PCT/EP2008/010410
§ 371 (c)(1),
(2), (4) Date: Sep. 20, 2010

(87) PCT Pub. No.: WO2009/080198
PCT Pub. Date: Jul. 2, 2009

(65) Prior Publication Data
US 2011/0046162 A1 Feb. 24, 2011

(30) Foreign Application Priority Data
Dec. 20, 2007 (DE) .................. 10 2007 061 764

(51) Int. Cl.
*A01N 43/90* (2006.01)
*A61K 31/519* (2006.01)
*C07D 491/00* (2006.01)

(52) U.S. Cl.
USPC ...................................... 514/264.1; 544/278

(58) Field of Classification Search
USPC .......... 544/278, 279, 276; 514/264.1, 264.11, 514/265.1
See application file for complete search history.

(56) References Cited

U.S. PATENT DOCUMENTS

| | | | |
|---|---|---|---|
| 4,052,510 A | 10/1977 | Simpson et al. |
| 5,670,525 A | 9/1997 | Urbahns et al. |
| 5,889,002 A | 3/1999 | Nielsen et al. |
| 6,191,280 B1 | 2/2001 | Hamprecht et al. |
| 6,586,441 B2 | 7/2003 | Barroni et al. |
| 6,632,823 B1 | 10/2003 | Vernier et al. |
| 6,693,102 B2 | 2/2004 | Stasch et al. |
| 6,706,717 B2 | 3/2004 | Barrish et al. |
| 6,743,798 B1 | 6/2004 | Straub et al. |
| 6,833,364 B1 | 12/2004 | Straub et al. |
| 6,864,287 B1 | 3/2005 | Alonso-Alija et al. |
| 7,045,631 B2 | 5/2006 | Rosentreter et al. |
| 7,078,417 B2 | 7/2006 | Rosentreter et al. |
| 7,109,218 B2 | 9/2006 | Rosentreter et al. |
| 7,129,255 B2 | 10/2006 | Rosentreter et al. |
| 7,135,486 B1 | 11/2006 | Rosentreter et al. |
| 7,173,036 B2 | 2/2007 | Sircar et al. |
| 7,173,037 B2 | 2/2007 | Alonso-Alija et al. |
| 7,186,716 B2 | 3/2007 | Wei et al. |
| 7,674,825 B2 | 3/2010 | Alonso-Alija et al. |
| 7,692,017 B2 | 4/2010 | Dinsmore et al. |
| 7,705,043 B2 | 4/2010 | Alonso-Alija et al. |
| 7,709,504 B2 | 5/2010 | Krahn et al. |
| 7,781,470 B2 | 8/2010 | Alonso-Alija et al. |
| 7,825,255 B2 | 11/2010 | Rosentreter et al. |
| 7,855,219 B2 | 12/2010 | Rosentreter et al. |
| 7,932,259 B2 | 4/2011 | Nakazato et al. |
| 7,951,811 B2 | 5/2011 | Nakazato et al. |
| 2003/0232860 A1 | 12/2003 | Harada et al. |
| 2004/0162427 A1 | 8/2004 | Rosentreter et al. |
| 2004/0176446 A1 | 9/2004 | Alonso-Alija et al. |
| 2005/0182105 A1 | 8/2005 | Nirschi et al. |
| 2005/0227972 A1 | 10/2005 | Rosentreter et al. |
| 2005/0250774 A1 | 11/2005 | Ono et al. |
| 2006/0264432 A1 | 11/2006 | Rosentreter et al. |
| 2007/0066630 A1 | 3/2007 | Palani et al. |
| 2007/0293670 A1 | 12/2007 | Nakazato et al. |
| 2008/0167321 A1 | 7/2008 | Kamboj et al. |
| 2008/0269300 A1 | 10/2008 | Erguden et al. |
| 2009/0221649 A1 | 9/2009 | Krahn et al. |
| 2010/0009973 A1 | 1/2010 | Rhodes et al. |
| 2010/0022544 A1 | 1/2010 | Nell et al. |
| 2010/0048641 A1 | 2/2010 | Nell et al. |
| 2010/0069363 A1 | 3/2010 | Nell et al. |
| 2010/0093728 A1 | 4/2010 | Nell et al. |

(Continued)

FOREIGN PATENT DOCUMENTS

EP          0 608 565 A1     12/1993
JP           09-132529         5/1997

(Continued)

OTHER PUBLICATIONS

Eissa et al., "Synthesis and biological evaluation of . . . ", Egyptian J'nal of Chem., (2006). 49(6), 761-774.*
Anand, et al.:"Novel Dipeptide Prodrugs of Acyclovir for Ocular Herpes Infections: Bioreversion, Antiviral Activity and Transport Across Rabbit Cornea," Current Eye Research, Mar. 2003, 26 (3-4):151-163.
Avila, et al.: A1-, A2A- and A3-subtype adenosine receptors modulate intraocular pressure in the mouse, British Journal of Pharmacology, 2001, 134:241-245.
Barnaby, et al.:"Structure-Activity Relationship Study of Prion Inhibition by 2-Aminopyridine-3,5-dicarbonitrile-Based Compounds: Parallel Synthesis, Bioactivity, and in Vitro Pharmacokinetics," J. Med. Chem., 2007, 50:65-73.
Barton et al.,:"Homologation of Acids via Carbon Radicals Generated from the Acyl Derivatives of N-Hydroxy-2-Thiopyrodine. (The Two-Carbon Problem)," Tetrahedron Letters, 1991, 32(28): 3309-3312.
Bauman:"Updating the Evidence that Physical Activity is Good for Health: An Epidemiological Review 2000-2003," J. Sci. Med. Sport, Apr. 2004, 7(1): Suppl:6-19.

(Continued)

*Primary Examiner* — Paul V. Ward
(74) *Attorney, Agent, or Firm* — Karen B. King

(57) ABSTRACT

The present application relates to novel substituted fused cyanopyridine derivatives, to processes for their preparation, to their use for the treatment and/or prevention of diseases and to their use for preparing medicaments for the treatment and/or prevention of diseases, preferably for the treatment and/or prevention of cardiovascular disorders.

9 Claims, No Drawings

(56) References Cited

U.S. PATENT DOCUMENTS

| | | | |
|---|---|---|---|
| 2011/0003845 A1 | 1/2011 | Nell et al. |
| 2011/0130377 A1 | 6/2011 | Nell et al. |
| 2011/0136871 A1 | 6/2011 | Hübsch et al. |
| 2011/0207698 A1 | 8/2011 | Meibom et al. |
| 2011/0237629 A1 | 9/2011 | Meibom et al. |
| 2011/0294718 A1 | 12/2011 | Lerchen et al. |

FOREIGN PATENT DOCUMENTS

| | | |
|---|---|---|
| JP | 10-324687 | 12/1998 |
| JP | 2003-183254 | 7/2003 |
| WO | 95/34563 | 12/1995 |
| WO | 97/27177 A2 | 7/1997 |
| WO | 99/03861 A1 | 1/1999 |
| WO | 02/48115 A2 | 6/2002 |
| WO | 02/50071 A1 | 6/2002 |
| WO | 03/091246 | 11/2003 |
| WO | 2004/014372 A1 | 2/2004 |
| WO | 2004/054505 A2 | 7/2004 |
| WO | 2005/007647 | 1/2005 |
| WO | 2007/073855 | 7/2007 |
| WO | 2008/008059 | 1/2008 |

OTHER PUBLICATIONS

Beaumont, et al.:"Design of Ester Prodrugs to Enhance Oral Absorption of Poorly Permeable Compounds: Challenges to the Discovery Scientist," Current Drug Metabolism, 2003, 4(6):461-485.
Beukers, et al.:"New, Non-Adenosine, High-Potency Agonists for the Human Adenosine A2B Receptor with an Improved Selectivity Profile Compared to the Reference Agonist N-Ethylcarboxamidoadenosine," Journal of Medicinal Chemistry, Jul. 15, 2004, 47(15): 3707-3709.
Bundgaard:"Design of Prodrugs: Bioreversible Derivatives for Various Functional Groups and Chemical Entities," Elsevier Science Publishers B.V., 1985, pp. 1092.
Castedo, et al.:"Synthesis and Pharmacological Activity of Some Nitrofuraldehyde Cyanopyridine Derivatives," Eur. J. Med. Chem., 1984, 19(6):555-557, abstract retrieved from CAPLUS Accession No. 1985:437337, EPO Document XP002202946.
Cesar, et al.:"Trimethylsilyldiazomethane in the Preparation of Diazoketonesvia Mixed Anhydride and Coupling Reagent Methods:A New Approach to the Arndt-Eistert Synthesis," Tetrahedron Letters, 2001, 42: 7099-7102.
Crosson: "Intraoccular Pressure Responses to the Adenosine Agonist Cyclohexyladenosine: Evidence for a Dual Mechanism of Action," IOVS, Jul. 2001, 42(8): 1837-1840.
Dhalla, et al.:"Pharmacology and Theraputic Applications of A1 Adenosine Receptor Ligands," Current Topics In Medicinal Chemisty, 2003, 3:369-385.
Dyachenko, et al.:"Single Stage Synthesis of 2-Alkylthio(seleno)-4-Hetaryl-3-cyano-5,6,7,8-Tetrahydroquinolines," Chemistry of Heterocyclic Compounds, 1997, 33(10): 1203-1208.
Dyachenko, et al.:"New Route to 6-Amino-4-aryl-3,5-dicyanopyridine-2(1H)-thiones," Russian Journal of Organic Chemistry,1997, 33(7):1014-1017.
Dyachenko, et al.:"Michael Reaction in SyntheSis of 6-Amino-4-(4-Butoxyphenyl)-3,5- Dicyanopyridine-2(1H)-thionene," Chemistry of Heterocyclic Compounds, 1998, 34(2):188-194.
Dyachenko:"Cyclohexanecarbaldehyde in Multicomponent Syntheses of Functionalized Cyclohexyl-Substituted Acrylonitriles, 4H-Chalcogenopyrans, 1,4-Dihydropyridines, and Pyridines," Russian Journal of General Chemistry, 2006, 76(2):282-291.
Dyachenko, et al.,:"Synthesis and Recyclization of 4-Aryl-2,6-diamino-3,5-dicyano-4H-thiopyrans," Russian Journal of Organic Chemistry, 1998, 34(4): 557-563.
Eissa, et al.:"Synthesis and Biological Evaluation of Pyrido[2,3-d]pyrimidine as Antitumor Effect," Egypt. J. Chem., 2006, 49(6):761-774.
Elnagdi, et al.:"Studies with Polyfunctionally Substituted Heterocycles: Synthesis of New Pyridines, Naphtho[1,2-b] pyrans, Pyrazolo[3,4]pyridines and Pyrazolo[1,5-a]pyrimidines," Z. Naturforsch., 1992, 47b:572-578.

El-Torgoman, et al.:"Nitriles in Heterocyclic Synthesis: The reaction of 2-Thiocarbamoyl Cinnamonitriles with Active Methylene Reagents," Z. Naturforsch., 1987, 42b:107-111.
Ettmayer, et al.:"Lessons Learned from Marketed and Investigational Prodrugs," J. Med. Chem., May 6, 2004, 47(10)2393-2404.
Fuentes, et al.:"Heterocycle Synthesis. XVI. Reaction of Malononitrile with Benzylidenemalononitriles in Presence of Amines." An. Quim., Ser. C., 1980, 76(1): 68-69, English language abstract retrieved from CAPLUS Accession No. 1981:139574, EPO Document No. XP002202947.
Goto, et al.:"Studies on Azole Compounds.III.1 Reactions of Oxazole N-Oxides with Phosphoryl Chloride and Acetic Anhydride 2", Chem. Pharm. Bull. 1971, 19: 2050-2057.
Ibrahim, et al.:"Synthesis and Biological Activity of Some New Heterocyclic Quinoline Derivatives," Phosphorus, Sulfer, and Silicon, 1991, 57: 293-301.
Jacobson, et al,:"Adenosine Receptors as Theraputic Targets," Nat. Rev. Drug Discover.,2005, 5:247-264.
Jacobson, et al.:"Adenosine Receptor Ligands: Differences with Acute Versus Chronic Treatment," Trends in Pharmacological Sciences, Mar. 1996, 17(3):108-113.
Kambe, et al.:"Synthetic Studies Using $\alpha,\beta$-Unsaturated Nitriles: Facile Synthesis of Pyridine Derivatives," Synthesis Communications, Jul. 1981, pp: 531-533.
Klotz, et al.:"Comparative Pharmacology of Human Adenosine Receptor Subtypescharacterization of Stably Transfected Receptors in CHO Cells," Naunyn-Schmiedeberg's Arch Pharmacol, 1998, 357:1-9.
Klotz:"Adenosine Receptors and their Ligands," Naunyn-Schmiedeberg's Arch. Pharmacol., 2000, 362: 382-391.
Müller, et al.:"Adenosine Receptor Antagonists: Structures and Potential Therapeutic Applications," Current Pharmaceutical Design, 1996, 2:501-530.
Müller:"Adenosine Receptor Ligands-Recent Developments Part I. Agonists," Current Medicinal Chemistry, 2000, 7:1269-1288.
Müller:"Review. Cardiovascular & Renal. A1-Adenosine Receptor Antagonists," Exp. Opin. Ther. Patents, 1997, 7(5):419-440.
Inotek Pharmaceuticals Press Release, "Inotek Pharmaceuticals Initiates Multiple-Dose Phase 2 Clinical Trial of INO-8875 in Patients with Glaucoma," Jun. 17, 2010.
Olah, et al.:"Cloning, Expression, and Characterization of the Unique Bovine A1 Adenosine Receptor," Journal of Biological Chemistry, May 25, 1992, 267(15):10764-10770.
Patani, et al.: "Bioisosterism: A Rational Approach in Drug Design," Chem. Rev., 1996, 96:3147-3176.
Pflueger, et al.:"Role of Adenosine in Contrast Media-Induced Acute Renal Failure in Diabetes Mellitus," Mayo Clin Proc., Dec. 2000, 75(12):1275-1283.
Poulsen, et al.:"Adenosine Receptors: New Opportunities for Future Drugs," Bioorganic & Medicinal Chemistry, Jan. 8, 1998, 6(6): 619-641.
Quintela, et al.:"Reactivity of Heterocyclic Compounds. V. Behavior of 6-alkoxy-2-amino-(or chloro)-4-aryl-3,5-dicyanopyridines in the Presence of Nucleophiles," Anales de Quimica, Serie C: Quimica Organica y Bioquimica, 1984, 80(3):268-72, English language abstract retrieved from CAPLUS Accession No. 1985:437345, CAPLUS Document No. 103:37345, EPO Document No. XP002202945.
Quintela, et al.:"Synthesis, Antihistaminic and Cytotoxic Activity of Pyridothieno- and Pyridodithienotriazines", Eur. J. Med. Chem, 1998, 33:887-897.
Rodinovskaya, et al.:"Substituted 4-(3-Cyanopyridin-2-ylthio)acetoacetates: New Convenient Reagents for the Synthesis of Heterocycles," Synthesis, 2006, (14): 2357-2370.
Rosenman:"Do Environmental Effects on Human Emotions Cause Cardiovascular Disorders?," Acta Physiologica Scandinavica, Supplement,1997, 161/640 (133-136), abstract retrieved from EMBASE Accession No. 97358868.
Ruhe, et al.:"Use of Antioxidant Nutrients in the Prevention and Treatment of Type 2 Diabetes," Journal of the American College of Nutrition, 2001, 20(5): 363S-369S.
Shams, et al.:"Nitriles in Organic Synthesis. New Routes for Synthesis of Pyridines and Azinothiopyrans," Journal fuer Praktische

(56) References Cited

OTHER PUBLICATIONS

Chemie (Leipzig), 1988, 330(5):817-13, abstract retrieved from CAPLUS Accession No. 1989:497050.
Sheridan:"The Most Common Chemical Replacements in Drug-Like Compounds," J Chem. Inf. Comput. Sci., 2002, 42:103-108.
Suttner, et al.:"The Heart in the Elderly Critically III Patient," Curr. Opin. Crit. Care, Oct. 2002, 8(5):389-94, abstract retrieved from MEDLINE Accession No. 2002495386, PubMed ID: 12357105.
Szydlowski, et al.:"Biological Role of Chromium," Diabetologia Polska, 2003, 10(3):365-370, English language abstract retrieved from EMBASE Accession No. 2004016455.
Vasudevan A. et al., "Aminopiperidine indazoles as orally efficacious melanin concentrating hormone receptoer-1 antagonists," Bioorg. Med. Chem. Lett. 2005, 15 (23), 5293-5297.
Vippagunta, et al.:"Crystalline Solids," Advanced Drug Delivery Reviews, May 16, 2001, 48(1):3-26.
West:"Solid State Chemistry and its Applications," Wiley, New York, 1988, pp. 358 & 365.
Ye, et al.:Organic Synthesis with α-Diazocarbonyl Compounds, Chem. Rev. 1994, 94:1091-1160.
Yu, et al:"Physical Characterization of Polymorphic Drugs: An Integrated Characterization Strategy," Pharmaceutical Science & Technology Today, Jun. 1998, 1(3):118-127.
Zhu, G. et al., "Design and synthesis of pyridine-pyrazolopyridine-based inhibitors of protein kinase B/Akt," Bioorg. Med. Chem. 2007, 15 (6), 2441-2452.

U.S. Appl. No. 11/607,262, filed Dec. 27, 2011, published as US 2007-0213372.
U.S. Appl. No. 11/661,820, filed Mar. 10, 2008, published as US 2008-0269300.
U.S. Appl. No. 12/516,939, filed Nov. 24, 2009 published as US 2010-0069363.
U.S. Appl. No. 12/440,423, filed Dec. 23, 2009 published as US 2010-0093728.
U.S. Appl. No. 12/516,917, filed May 29, 2009, published as US 2010-0022544.
U.S. Appl. No. 12/671,694, filed Jul. 27, 2011, published as US 2011-0294718.
U.S. Appl. No. 12/922,172, filed May 16, 2011 published as US 2011-0207698.
U.S. Appl. No. 12/995,028, filed Feb. 16, 2011 published as US 2011-0207698.
U.S. Appl. No. 13/132,991, filed Aug. 23. 2011 published as US 2011-0294719.
U.S. Appl. No. 12/697,000, filed Jan. 29, 2010, published as US 2010-0197609.
U.S. Appl. No. 13/210,889, filed Aug. 16, 2011.
U.S. Appl. No. 12/671,019, filed Jan. 27, 2010, published as US 2011-0130377.
U.S. Appl. No. 12/809,674, filed Sep. 21, 2010 published as US 2011-0003845.

\* cited by examiner

FUSED CYANOPYRIDINES AND THE USE THEREOF

The present application relates to novel substituted fused cyanopyridine derivatives, to processes for their preparation, to their use for the treatment and/or prevention of diseases and to their use for preparing medicaments for the treatment and/or prevention of diseases, preferably for the treatment and/or prevention of cardiovascular disorders. Adenosine, a purine nucleoside, is present in all cells and is released by a large number of physiological and pathophysiological stimuli. Adenosine is formed intracellularly as an intermediate during the degradation of adenosine 5'-monophosphate (AMP) and S-adenosylhomocysteine, but it can be released from the cell, in which case it acts as a hormone-like substance or neurotransmitter by binding to specific receptors. Under normoxic conditions, the concentration of free adenosine in the extracellular space is very low. However, under ischemic or hypoxic conditions, the extracellular concentration of adenosine in the affected organs is increased dramatically. Thus, it is known, for example, that adenosine inhibits platelet aggregation and increases the blood supply to the coronary arteries. Furthermore, it acts on the blood pressure, on the heart rate, on the release of neurotransmitters and on lymphocyte differentiation. In adipocytes, adenosine is capable of inhibiting lipolysis, thus lowering the concentration of free fatty acids and triglycerides in the blood.

The aim of these actions of adenosine is to increase the oxygen supply of the affected organs and/or to reduce the metabolism of these organs in order to adjust the metabolism of the organ to the blood supply of the organ under ischemic or hypoxic conditions.

The action of adenosine is mediated via specific receptors. To date, subtypes A1, A2a, A2b and A3 are known. According to the invention, "adenosine-receptor-selective ligands" are substances which bind selectively to one or more subtypes of the adenosine receptors, thus either mimicking the action of adenosine (adenosine agonists) or blocking its action (adenosine antagonists).

The actions of these adenosine receptors are mediated intracellularly by the messenger cAMP. In the case of the binding of adenosine to the A2a or A2b receptors, the intracellular cAMP is increased via activation of the membrane-bound adenylate cyclase, whereas binding of adenosine to the A1 or A3 receptors results in a decrease of the intracellular cAMP concentration via inhibition of adenylate cyclase.

In the cardiovascular system, the main consequences of the activation of adenosine receptors are: bradycardia, negative inotropism and protection of the heart against ischemia ("preconditioning") via A1 receptors, dilation of the blood vessels via A2a and A2b receptors and inhibition of the fibroblasts and smooth-muscle-cell proliferation via A2b receptors.

In the case of A1 agonists (coupling preferably via $G_i$ proteins), a decrease of the intracellular cAMP concentration is observed (preferably after direct prestimulation of adenylate cyclase by forskolin). Correspondingly, A2a and A2b agonists (coupling preferably via $G_s$ proteins) lead to an increase and A2a and A2b antagonists to a decrease of the cAMP concentration in the cells. In the case of A2 receptors, a direct prestimulation of adenylate cyclase by forskolin is of no benefit.

In humans, activation of A1 receptors by specific A1 agonists leads to a frequency-dependent lowering of the heart rate, without any effect on blood pressure. Selective A1 agonists may thus be suitable inter alia for treating angina pectoris and atrial fibrillation. The cardioprotective action of the A1 receptors in the heart may be utilized inter alia by activating these A1 receptors with specific A1 agonists for treatment and organ protection in cases of acute myocardial infarction, acute coronary syndrome, heart failure, bypass operations, heart catheter examinations and organ transplantations. The activation of A2b receptors by adenosine or specific A2b agonists leads, via dilation of blood vessels, to lowering of the blood pressure. The lowering of the blood pressure is accompanied by a reflectory increase in heart rate. The increased heart rate can be reduced by activation of A1 receptors using specific A1 agonists.

The combined action of selective A1/A2b agonists on the vascular system and heart rate thus results in a systemic lowering of the blood pressure without relevant heart-rate increase. Dual A1/A2b agonists having such a pharmacological profile could be employed, for example, for treating hypertension in humans.

In humans, the inhibition of A1 receptors by specific A1 antagonists has a uricosuric, natriuretic and potassium-sparing diuretic effect without affecting the glomerular filtration rate, thus being renoprotective. Accordingly, selective A1 antagonists can be suitable inter alia for treating acute heart failure and chronic heart failure. Furthermore, they can be used for renoprotection in cases of nephropathy and other renal disorders.

In adipocytes, the activation of A1 and A2b receptors leads to an inhibition of lipolysis. Thus, the combined action of A1/A2b agonists on lipid metabolism results in a lowering of free fatty acids and triglycerides. In turn, in patients suffering from metabolic syndrome and in diabetics, reducing lipids leads to lower insulin resistance and improved symptoms.

The abovementioned receptor selectivity can be determined by the effect of the substances on cell lines which, after stable transfection with the corresponding cDNA, express the receptor subtypes in question [see the publication M. E. Olah, H. Ren, J. Ostrowski, K. A. Jacobson, G. L. Stiles, "Cloning, expression, and characterization of the unique bovine A1 adenosine receptor. Studies on the ligand binding site by site-directed mutagenesis", J. Biol. Chem. 267 (1992), pages 10764-10770, the disclosure of which is hereby fully incorporated by way of reference].

The effect of the substances on such cell lines can be studied by biochemical measurement of the intracellular messenger cAMP (see the publication K. N. Klotz, J. Hessling, J. Hegler, C. Owman, B. Kull, B. B. Fredholm, M. J. Lohse, "Comparative pharmacology of human adenosine receptor subtypes—characterization of stably transfected receptors in CHO cells", Naunyn Schmiedebergs Arch. Pharmacol. 357 (1998), pages 1-9, the disclosure of which is hereby fully incorporated by way of reference).

The "adenosine-receptor-specific" ligands known from the prior art are mainly derivatives based on natural adenosine [S.-A. Poulsen and R. J. Quinn, "Adenosine receptors: New opportunities for future drugs", Bioorganic and Medicinal Chemistry 6 (1998), pages 619-641]. However, these adenosine ligands known from the prior art have the disadvantage that their action is not really receptor-specific, that their activity is less than that of natural adenosine or that they have only very weak activity after oral administration. Thus, they are mainly used only for experimental purposes. Compounds of this type which are still in clinical development are hitherto only suitable for intravenous application.

The synthesis of various tetrahydroquinoline derivatives is described in Synthesis 2006, 14: 2357-2370, Chemistry of Heterocyclic Compounds 1997, 33 (10): 1203-1208 and Phosphorus, Sulfur and Silicon 1991, 57: 293-301. 6,7-Dihydro-5H-cyclopent[b]pyridines are described in Ukrainskii Khimicheskii Zhournal (Russian Edition) 2006, 72 (1-2): 116-120 as synthesis intermediates. WO 2004/014372 discloses heteroarylically fused cycloalkenylamines as eNO-synthase stimulators for the treatment of cardiovascular disorders. WO 02/48115 describes pyridinylpyrimidones and quinazolinones for the treatment of parasitic disorders. EP 0 608 565 claims pyrido[2,3-d]pyrimidines substituted in various ways as endothelin receptor antagonists for the treatment of inter alia acute renal failure, hypertension and myocardial infarction. EP 0 537 463 describes substituted pyrido[2,3-d]pyrimidines as herbicides. US 2007/0066630 discloses various fused heterocycles as agonists of the nicotinic acid receptor for the treatment of metabolic syndrome, of dyslipidemia, cardiovascular disorders and disorders of the peripheral and central nervous system.

It is an object of the present invention to provide novel compounds which act as selective ligands of the adenosine A1 and/or adenosine A2b receptor and which, as such, are suitable for the treatment and/or prevention of diseases, in particular for the treatment and/or prevention of cardiovascular disorders.

The present invention provides compounds of the formula (I)

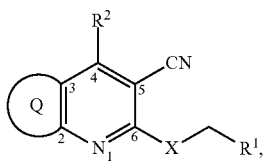

in which ring Q represents a group of the formula

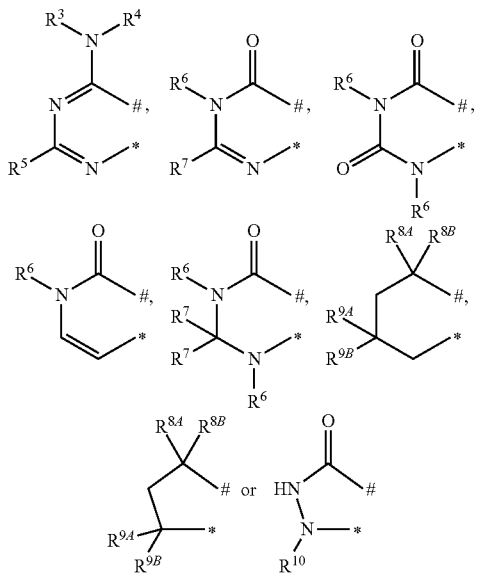

where
* represents in each case the point of attachment to the C2 atom,
# represents in each case the point of attachment to the C3 atom,
$R^3$ represents hydrogen or $(C_1-C_4)$-alkyl,
$R^4$ represents hydrogen or $(C_1-C_4)$-alkyl,
$R^5$ represents hydrogen, $(C_1-C_4)$-alkyl or amino,
$R^6$ represents in each case hydrogen, $(C_1-C_4)$-alkyl or allyl, in which $(C_1-C_4)$-alkyl may be substituted by a substituent selected from the group consisting of hydroxycarbonyl, $(C_1-C_4)$-alkoxycarbonyl and amino,
$R^7$ represents in each case hydrogen, $(C_1-C_4)$-alkyl, trifluoromethyl, amino, mono-$(C_1-C_4)$-alkylamino or di-$(C_1-C_4)$-alkylamino,
in which $(C_1-C_4)$-alkyl may be substituted by 1 or 2 substituents independently of one another selected from the group consisting of hydroxyl, methoxy and amino, and either
i) $R^{8A}$ represents in each case hydrogen, hydroxyl, $(C_1-C_4)$-alkoxy or mono-$(C_1-C_4)$-alkylamino,
in which $(C_2-C_4)$-alkoxy and mono-$(C_2-C_4)$-alkylamino may be substituted by a hydroxyl substituent, and
$R^{8B}$ represents hydrogen,
or
$R^{8A}$ together with $R^{8B}$ forms an oxo, N—$(C_1-C_4)$-alkylimino, N—$(C_1-C_4)$-alkoxyimino or $(C_1-C_4)$-alkoxycarbonylmethylidene group, and
$R^{9A}$ and $R^{9B}$ independently of one another represent in each case hydrogen or $(C_1-C_4)$-alkyl or together with the carbon atom to which they are attached form a spiro-linked 3- to 5-membered cycloalkyl ring, and
$R^{10}$ represents hydrogen, $(C_1-C_4)$-alkyl or phenyl,
in which $(C_1-C_4)$-alkyl may be substituted by 1 or 2 substituents independently of one another selected from the group consisting of hydroxyl and amino,
X represents S or O,
$R^1$ represents $(C_6-C_{10})$-aryl or 5- to 10-membered heteroaryl,
where $(C_6-C_{10})$-aryl and 5- to 10-membered heteroaryl may be substituted by 1 or 2 substituents independently of one another selected from the group consisting of halogen, nitro, cyano, $(C_1-C_6)$-alkyl, trifluoromethyl, hydroxyl, $(C_1-C_6)$-alkoxy, amino, mono-$(C_1-C_6)$-alkylamino, di-$(C_1-C_6)$-alkylamino, hydroxycarbonyl, $(C_1-C_6)$-alkoxycarbonyl, aminocarbonyl, mono-$(C_1-C_6)$-alkylaminocarbonyl, di-$(C_1-C_6)$-alkylaminocarbonyl, pyrrolidino, piperidino, morpholino, piperazino and N'—$(C_1-C_4)$-alkylpiperazino, phenyl and 5- or 6-membered heteroaryl,
in which phenyl and 5- or 6-membered heteroaryl may be substituted by 1 to 3 substituents independently of one another selected from the group consisting of halogen, nitro, cyano, $(C_1-C_6)$-alkyl, difluoromethyl, trifluoromethyl, hydroxyl, $(C_1-C_6)$-alkoxy, difluoromethoxy, trifluoromethoxy, amino, mono-$(C_1-C_6)$-alkylamino, di-$(C_1-C_6)$-alkylamino, hydroxycarbonyl and $(C_1-C_6)$-alkoxycarbonyl,
$R^2$ represents $(C_5-C_6)$-cycloalkyl, 5- or 6-membered heterocyclyl, phenyl or 5- or 6-membered heteroaryl,
where $(C_5-C_6)$-cycloalkyl may be substituted by 1 or 2 substituents independently of one another selected from the group consisting of $(C_1-C_6)$-alkyl, hydroxyl, oxo, $(C_1-C_6)$-alkoxy, amino, mono-$(C_1-C_6)$-alkylamino and di-$(C_1-C_6)$-alkylamino,
in which $(C_1-C_6)$-alkyl and $(C_1-C_6)$-alkoxy may be substituted by 1 or 2 substituents independently of one another selected from the group consisting of hydroxyl, $(C_1-C_4)$-alkoxy and $(C_3-C_7)$-cycloalkyl,
in which $(C_3-C_7)$-cycloalkyl for its part may be substituted by 1 or 2 substituents independently of one another selected from the group consisting of $(C_1-C_4)$-alkyl, hydroxyl, oxo and $(C_1-C_4)$-alkoxy, and
where 5- or 6-membered heterocyclyl may be substituted by 1 to 3 substituents independently of one another selected from the group consisting of oxo, thioxo, hydroxyl, ($C_1$-$C_6$)-alkyl, ($C_1$-$C_6$)-alkoxy, ($C_1$-$C_6$)-alkylcarbonyl, amino, mono-($C_1$-$C_6$)-alkylamino, di-($C_1$-$C_6$)-alkylamino and ($C_3$-$C_7$)-cycloalkyl, in which ($C_1$-$C_6$)-alkyl may be substituted by 1 to 3 substituents independently of one another selected from the group consisting of fluorine, oxo, hydroxyl, trifluoromethyl, ($C_1$-$C_4$)-alkoxy, ($C_1$-$C_4$)-alkylcarbonyloxy, amino, mono-($C_1$-$C_4$)-alkylamino, di-($C_1$-$C_4$)-alkylamino and ($C_3$-$C_7$)-cycloalkyl, in which ($C_3$-$C_7$)-cycloalkyl for its part may be substituted by 1 or 2 substituents independently of one another selected from the group consisting of ($C_1$-$C_4$)-alkyl, hydroxyl, oxo and ($C_1$-$C_4$)-alkoxy, and in which ($C_1$-$C_6$)-alkylcarbonyl may be substituted by a substituent selected from the group consisting of hydroxyl and ($C_1$-$C_4$)-alkoxy, and in which ($C_3$-$C_7$)-cycloalkyl may be substituted by 1 or 2 substituents independently of one another selected from the group consisting of ($C_1$-$C_4$)-alkyl, hydroxyl, oxo and ($C_1$-$C_4$)-alkoxy, and where phenyl and 5- or 6-membered heteroaryl may be substituted by 1 to 3 substituents independently of one another selected from the group consisting of halogen, cyano, hydroxyl, ($C_1$-$C_6$)-alkyl, ($C_1$-$C_6$)-alkoxy, ($C_3$-$C_7$)-cycloalkoxy and —$NR^A R^B$, in which ($C_1$-$C_6$)-alkyl may be substituted by 1 to 3 fluorine substituents, and in which ($C_1$-$C_6$)-alkoxy may be substituted by 1 to 3 substituents independently of one another selected from the group consisting of fluorine, trifluoromethyl, ($C_3$-$C_7$)-cycloalkyl, oxo, hydroxyl, ($C_1$-$C_4$)-alkoxy, hydroxycarbonyl, amino, mono-($C_1$-$C_4$)-alkylamino and di-($C_1$-$C_4$)-alkylamino, and in which ($C_3$-$C_7$)-cycloalkoxy may be substituted by 1 or 2 substituents independently of one another selected from the group consisting of ($C_1$-$C_4$)-alkyl, hydroxyl, oxo and ($C_1$-$C_4$)-alkoxy, and in which $R^A$ represents hydrogen or ($C_1$-$C_6$)-alkyl, in which ($C_1$-$C_6$)-alkyl for its part may be substituted by a substituent selected from the group consisting of hydroxyl and ($C_1$-$C_4$)-alkoxy, $R^B$ represents hydrogen, ($C_1$-$C_6$)-alkyl, ($C_3$-$C_7$)-cycloalkyl, ($C_1$-$C_4$)-alkylsulfonyl or ($C_3$-$C_7$)-cycloalkylsulfonyl, in which ($C_1$-$C_6$)-alkyl for its part may be substituted by 1 or 2 substituents independently of one another selected from the group consisting of ($C_3$-$C_7$)-cycloalkyl, oxo, hydroxyl, ($C_1$-$C_4$)-alkoxy, hydroxycarbonyl, amino, mono-($C_1$-$C_4$)-alkylamino and di-($C_1$-$C_4$)-alkylamino, and in which ($C_3$-$C_7$)-cycloalkyl for its part may be substituted by 1 or 2 substituents independently of one another selected from the group consisting of ($C_1$-$C_4$)-alkyl, hydroxyl, oxo and ($C_1$-$C_4$)-alkoxy, or in which two adjacent substituents at the phenyl together with the carbon atoms to which they are attached may form a 1,3-dioxolane or 2,2-difluoro-1,3-dioxolane, and N-oxides, salts, solvates, salts of the N-oxides and solvates of the N-oxides and salts thereof, except for the compounds 5,6,7,8-tetrahydro-2-[[(2-methylphenyl)methyl]thio]-4-(2-thienyl)-3-quinolinecarbonitrile, 5,6,7,8-tetrahydro-2-[(phenylmethyl)thio]-4-(2-thienyl)-3-quinolinecarbonitrile, 5,6,7,8-tetrahydro-2-[[(2-methylphenyl)methyl]thio]-4-(4-pyridyl)-3-quinolinecarbonitrile, 5,6,7,8-tetrahydro-2-[(phenylmethyl)thio]-4-phenyl-3-quinolinecarbonitrile, 5,6,7,8-tetrahydro-2-[(phenylmethyl)thio]-4-(4-chlorophenyl)-3-quinolinecarbonitrile, 6,7-dihydro-4-(4-hydroxyphenyl)-2-[(phenylmethyl)thio]-5H-cyclopenta[b]pyridine-3-carbonitrile.

Compounds according to the invention are the compounds of the formula (I) and the salts, solvates and solvates of the salts thereof, the compounds which are encompassed by the formula (I) of the formulae mentioned below, and the salts, solvates and solvates of the salts thereof, and the compounds which are encompassed by formula (I) and are mentioned below as exemplary embodiments, and the salts, solvates and solvates of the salts thereof, where the compounds which are encompassed by the formula (I) and are mentioned below are not already salts, solvates and solvates of the salts.

The compounds according to the invention may, depending on their structure, exist in stereoisomeric forms (enantiomers, diastereomers). The invention therefore encompasses the enantiomers or diastereomers and respective mixtures thereof. The stereoisomerically pure constituents can be isolated from such mixtures of enantiomers and/or diastereomers in a known manner.

Where the compounds according to the invention can exist in tautomeric forms, the present invention encompasses all tautomeric forms.

Salts preferred for the purposes of the present invention are physiologically acceptable salts of the compounds according to the invention. Also included are salts which are not themselves suitable for pharmaceutical applications but can be used, for example, for the isolation or purification of the compounds according to the invention.

Physiologically acceptable salts of the compounds according to the invention include acid addition salts of mineral acids, carboxylic acids and sulfonic acids, for example salts of hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, acetic acid, trifluoroacetic acid, propionic acid, lactic acid, tartaric acid, malic acid, citric acid, fumaric acid, maleic acid and benzoic acid. Physiologically acceptable salts of the compounds according to the invention also include salts of conventional bases such as, by way of example and preferably, alkali metal salts (for example sodium and potassium salts), alkaline earth metal salts (for example calcium and magnesium salts) and ammonium salts derived from ammonia or organic amines having 1 to 16 carbon atoms, such as, by way of example and preferably, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

Solvates refer for the purposes of the invention to those forms of the compounds according to the invention which form a complex in the solid or liquid state through coordination with solvent molecules. Hydrates are a specific form of solvates in which the coordination takes place with water. For the purposes of the present invention, preferred solvates are hydrates.

In addition, the present invention also encompasses prodrugs of the compounds according to the invention. The term "prodrugs" encompasses compounds which for their part may be biologically active or inactive but are converted (for example metabolically or hydrolytically) into compounds according to the invention during their residence time in the body.

For the purposes of the present invention, the substituents have the following meaning, unless specified otherwise:

Alkyl is in the context of the invention a straight-chain or branched alkyl radical having 1 to 6 or 1 to 4 carbon atoms. A straight-chain or branched alkyl radical having 1 to 4 carbon atoms is preferred. The following radicals may be mentioned by way of example and by way of preference: methyl, ethyl, n-propyl, isopropyl, n-butyl, isobutyl, sec-butyl, tert-butyl, 1-ethylpropyl, n-pentyl and n-hexyl.

Cycloalkyl is in the context of the invention a monocyclic saturated carbocycle having 3 to 7 or 5 or 6 ring carbon atoms. The following radicals may be mentioned by way of example and by way of preference: cyclopropyl, cyclobutyl, cyclopentyl, cyclohexyl and cycloheptyl.

Alkylcarbonyl is in the context of the invention a straight-chain or branched alkyl radical having 1 to 6 or 1 to 4 carbon atoms and a carbonyl group attached in position 1. The following radicals may be mentioned by way of example and by way of preference: methylcarbonyl, ethylcarbonyl, n-propylcarbonyl, isopropylcarbonyl, n-butylcarbonyl, isobutylcarbonyl and tert-butylcarbonyl.

Alkylcarbonyloxy is in the context of the invention a straight-chain or branched alkyl radical having 1 to 4 carbon atoms and, attached in position 1, a carbonyl group which is attached via an oxygen atom. The following radicals may be mentioned by way of example and by way of preference: methylcarbonyloxy, ethylcarbonyloxy, n-propylcarbonyloxy, isopropylcarbonyloxy and tert-butylcarbonyloxy.

Alkoxy is in the context of the invention a straight-chain or branched alkoxy radical having 1 to 6 or 1 to 4 or 2 to 4 carbon atoms. A straight-chain or branched alkoxy radical having 1 to 4 or 2 to 4 carbon atoms is preferred. The following radicals may be mentioned by way of example and by way of preference: methoxy, ethoxy, n-propoxy, isopropoxy, n-butoxy, tert-butoxy, n-pentoxy and n-hexoxy.

Cycloalkoxy is in the context of the invention a monocyclic saturated alkoxy radical having 3 to 7 carbon atoms. The following radicals may be mentioned by way of example and by way of preference: cyclopropyloxy, cyclobutyloxy, cyclopentyloxy, cyclohexyloxy and cycloheptyloxy.

Alkoxycarbonyl is in the context of the invention a straight-chain or branched alkoxy radical having 1 to 6 or 1 to 4 carbon atoms and a carbonyl group attached at the oxygen. A straight-chain or branched alkoxycarbonyl radical having 1 to 4 carbon atoms in the alkoxy group is preferred. The following radicals may be mentioned by way of example and by way of preference: methoxycarbonyl, ethoxycarbonyl, n-propoxycarbonyl, isopropoxycarbonyl and tert-butoxycarbonyl.

Monoalkylamino is in the context of the invention an amino group having a straight-chain or branched alkyl substituent having 1 to 6 or 1 to 4 or 2 to 4 carbon atoms. A straight-chain or branched monoalkylamino radical having 1 to 4 or 2 to 4 carbon atoms is preferred. The following radicals may be mentioned by way of example and by way of preference: methylamino, ethylamino, n-propylamino, isopropylamino, n-butylamino, tert-butylamino, n-pentylamino and n-hexylamino.

Dialkylamino is in the context of the invention an amino group having two identical or different straight-chain or branched alkyl substituents having 1 to 6 or 1 to 4 carbon atoms each. Straight-chain or branched dialkylamino radicals having 1 to 4 carbon atoms each are preferred. The following radicals may be mentioned by way of example and by way of preference: N,N-dimethylamino, N,N-diethylamino, N-ethyl-N-methylamino, N-methyl-N-n-propylamino, N-isopropyl-N-n-propylamino, N,N-diisopropylamino, N-n-butyl-N-methylamino, N-tert-butyl-N-methylamino, N-ethyl-N-n-pentylamino and N-n-hexyl-N-methylamino.

Monoalkylaminocarbonyl is in the context of the invention an amino group which is attached via a carbonyl group and has a straight-chain or branched alkyl substituent having 1 to 6 or 1 to 4 carbon atoms. A monoalkylaminocarbonyl radical having 1 to 4 carbon atoms in the alkyl group is preferred. The following radicals may be mentioned by way of example and by way of preference: methylaminocarbonyl, ethylaminocarbonyl, n-propylaminocarbonyl, isopropylaminocarbonyl, n-butylaminocarbonyl and tert-butylaminocarbonyl.

Dialkylaminocarbonyl is in the context of the invention an amino group which is attached via a carbonyl group and which has two identical or different straight-chain or branched alkyl substituents having 1 to 6 or 1 to 4 carbon atoms each. A dialkylaminocarbonyl radical having in each case 1 to 4 carbon atoms per alkyl group is preferred. The following radicals may be mentioned by way of example and by way of preference: N,N-dimethylaminocarbonyl, N,N-diethylaminocarbonyl, N-ethyl-N-methylaminocarbonyl, N-methyl-N-n-propylaminocarbonyl, N-n-butyl-N-methylaminocarbonyl and N-tert-butyl-N-methylaminocarbonyl.

Alkylimino is in the context of the invention an imino group having a straight-chain or branched alkyl substituent having 1 to 4 carbon atoms. The following radicals may be mentioned by way of example and by way of preference: methylimino, ethylimino, n-propylimino, isopropylimino, n-butylimino and tert-butylimino.

Alkoxyimino is in the context of the invention an imino group having a straight-chain or branched alkoxy substituent having 1 to 4 carbon atoms. The following radicals may be mentioned by way of example and by way of preference: methoxyimino, ethoxyimino, n-propoxyimino, isopropoxyimino, n-butoxyimino and tert-butoxyimino.

Alkylsulfonyl is in the context of the invention a straight-chain or branched alkyl radical which has 1 to 4 carbon atoms and is attached via a sulfone group. The following radicals may be mentioned by way of example and by way of preference: methylsulfonyl, ethylsulfonyl, n-propylsulfonyl, isopropylsulfonyl, n-butylsulfonyl and tert-butylsulfonyl. Cycloalkylsulfonyl is in the context of the invention a monocyclic saturated alkyl radical which has 3 to 7 carbon atoms and is attached via a sulfone group. The following radicals may be mentioned by way of example and by way of preference: cyclopropylsulfonyl, cyclobutylsulfonyl, cyclopentylsulfonyl, cyclohexylsulfonyl and cycloheptylsulfonyl.

Heterocyclyl is in the context of the invention a saturated heterocycle having a total of 5 or 6 ring atoms which contains one or two ring heteroatoms from the group consisting of N, O and S and is attached via a ring carbon atom or, if appropriate, via a ring nitrogen atom. The following radicals may be mentioned by way of example: pyrrolidinyl, pyrazolidinyl, tetrahydrofuranyl, piperidinyl, piperazinyl, tetrahydropyranyl, morpholinyl, thiomorpholinyl, hexahydroazepinyl and hexahydro-1,4-diazepinyl. Pyrrolidinyl, tetrahydrofuranyl, piperidinyl, piperazinyl, tetrahydropyranyl and morpholinyl are preferred.

$(C_6-C_{10})$-Aryl is in the context of the invention an aromatic carbocycle having 6 or 10 ring carbon atoms. Preferred aryl radicals are phenyl and naphthyl.

Heteroaryl is in the context of the invention a mono- or optionally bicyclic aromatic heterocycle (heteroaromatic) which has a total of 5 to 10 ring atoms, contains up to three identical or different ring heteroatoms from the group consisting of N, O and S and is attached via a ring carbon atom or, if appropriate, via a ring nitrogen atom. The following radicals may be mentioned by way of example: furyl, pyrrolyl, thienyl, pyrazolyl, imidazolyl, thiazolyl, oxazolyl, isoxazolyl, isothiazolyl, triazolyl, oxadiazolyl, thiadiazolyl, pyridyl, pyrimidinyl, pyridazinyl, pyrazinyl, triazinyl, benzofuranyl, benzothienyl, benzimidazolyl, benzoxazolyl, benzothiazolyl, benzotriazolyl, indolyl, indazolyl, quinolinyl, isoquinolinyl, naphthyridinyl, quinazolinyl, quinoxalinyl, phthalazinyl, pyrazolo[3,4-b]pyridinyl. Monocyclic 5- or 6-membered heteroaryl radicals having up to three ring heteroatoms from the group consisting of N, O and S such as, for example, furyl, thienyl, thiazolyl, oxazolyl, isothiazolyl, isoxazolyl, pyrazolyl, imidazolyl, triazolyl, oxadiazolyl, thiadiazolyl, pyridyl, pyrimidinyl, pyridazinyl, pyrazinyl, triazinyl are preferred.

Halogen includes in the context of the invention fluorine, chlorine, bromine and iodine. Preference is given to chlorine or fluorine.

In the formulae of the group which may represent Q, the end point of the line marked by * or # does not represent a carbon atom or a $CH_2$ group but is part of the bond to the atom to which Q is attached.

When radicals in the compounds according to the invention are substituted, the radicals may be mono- or polysubstituted, unless specified otherwise. For the purposes of the present invention, the meanings of all radicals which occur more than once are independent of one another. Preference is given to substitution by one, two or three identical or different substituents. Very particularly preferred is substitution by one or two identical or different substituents.

In the context of the present invention, preference is given to compounds of the formula (I) in which ring Q represents a group of the formula

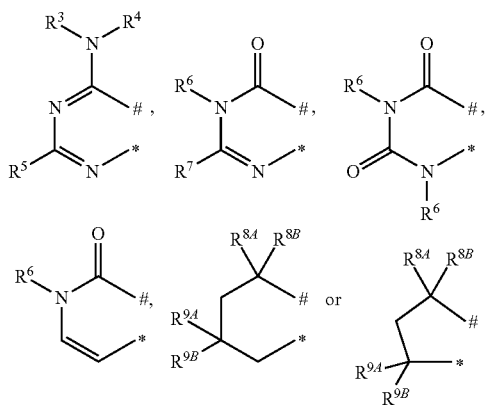

where
* represents in each case the point of attachment to the C2 atom,
# represents in each case the point of attachment to the C3 atom,
$R^3$ represents hydrogen or methyl,
$R^4$ represents hydrogen or methyl,
$R^5$ represents hydrogen or methyl,
$R^6$ represents in each case hydrogen or methyl,
$R^7$ represents in each case hydrogen or methyl,
and either
i) $R^{8A}$ represents in each case hydrogen or hydroxyl, and
$R^{8B}$ represents hydrogen, or
ii) $R^{8A}$ together with $R^{8B}$ forms an oxo group, and
$R^{9A}$ and $R^{9B}$ independently of one another represent in each case hydrogen or methyl,
X represents S or O,
$R^1$ represents phenyl or 5- or 6-membered heteroaryl, where phenyl and 5- or 6-membered heteroaryl are substituted by 1 or 2 substituents independently of one another selected from the group consisting of fluorine, chlorine, cyano, $(C_1-C_4)$-alkyl, trifluoromethyl, hydroxyl, $(C_1-C_4)$-alkoxy, amino, hydroxycarbonyl, $(C_1-C_4)$-alkoxycarbonyl, aminocarbonyl, phenyl and 5- or 6-membered heteroaryl, in which phenyl and 5- or 6-membered heteroaryl may be substituted by 1 to 3 substituents independently of one another selected from the group consisting of fluorine, chlorine, nitro, cyano, $(C_1-C_4)$-alkyl, difluoromethyl, trifluoromethyl, hydroxyl, $(C_1-C_4)$-alkoxy, difluoromethoxy, trifluoromethoxy, amino, hydroxycarbonyl and $(C_1-C_4)$-alkoxycarbonyl, $R^2$ represents cyclohexyl, tetrahydropyranyl, piperidinyl, piperazinyl, morpholinyl, phenyl, pyrazolyl, imidazolyl, oxazolyl, thiazolyl or pyridyl, where cyclohexyl may be substituted by a substituent selected from the group consisting of hydroxyl and $(C_1-C_4)$-alkoxy, in which $(C_2-C_4)$-alkoxy may be substituted by 1 or 2 substituents independently of one another selected from the group consisting of hydroxyl and methoxy, and where piperidinyl, piperazinyl and morpholinyl may be substituted by a substituent selected from the group consisting of $(C_1-C_4)$-alkyl, hydroxyl, $(C_1-C_4)$-alkoxy and $(C_1-C_4)$-alkylcarbonyl, in which $(C_1-C_4)$-alkyl may be substituted by 1 or 2 substituents independently of one another selected from the group consisting of hydroxyl, methoxy, ethoxy, methylcarbonyloxy and ethylcarbonyloxy, and in which $(C_1-C_4)$-alkylcarbonyl may be substituted by a substituent selected from the group consisting of hydroxyl, methoxy and ethoxy, and where phenyl and pyridyl may be substituted by 1 to 3 substituents independently of one another selected from the group consisting of fluorine, chlorine, cyano, hydroxyl, $(C_1-C_4)$-alkyl and $(C_1-C_4)$-alkoxy, in which $(C_2-C_4)$-alkoxy may be substituted by 1 or 2 substituents independently of one another selected from the group consisting of oxo, hydroxyl, $(C_1-C_4)$-alkoxy, hydroxycarbonyl and amino, and where pyrazolyl, imidazolyl, oxazolyl and thiazolyl may be substituted by 1 or 2 substituents independently of one another selected from the group consisting of fluorine, chlorine, cyano, hydroxyl, $(C_1-C_4)$-alkyl and $(C_1-C_4)$-alkoxy, in which $(C_2-C_4)$-alkoxy may be substituted by 1 or 2 substituents independently of one another selected from the group consisting of oxo, hydroxyl, $(C_1-C_4)$-alkoxy, hydroxycarbonyl and amino, and salts, solvates and solvates of the salts thereof, except for the compound 5,6,7,8-tetrahydro-2-[[(2-methylphenyl)methyl]thio]-4-(4-pyridyl)-3-quinolinecarbonitrile.

In the context of the present invention, particular preference is given to compounds of the formula (I) in which ring Q represents a group of the formula

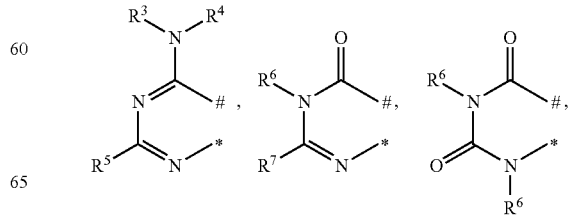

-continued

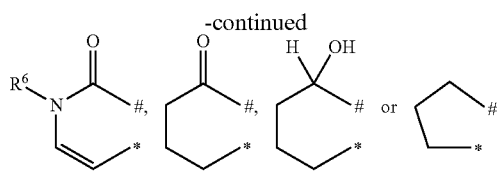

where
* represents in each case the point of attachment to the C2 atom,
# represents in each case the point of attachment to the C3 atom,
$R^3$ represents hydrogen,
$R^4$ represents hydrogen,
$R^5$ represents hydrogen or methyl,
$R^6$ represents in each case hydrogen or methyl, and
$R^7$ represents hydrogen or methyl,
X represents S or O,
$R^1$ represents phenyl or 5- or 6-membered heteroaryl,
where phenyl and 5- or 6-membered heteroaryl are substituted by 1 or 2 substituents independently of one another selected from the group consisting of fluorine, chlorine, cyano, methyl, ethyl, trifluoromethyl, hydroxyl, methoxy, ethoxy, amino, hydroxycarbonyl, methoxycarbonyl, ethoxycarbonyl, aminocarbonyl, phenyl and 5- or 6-membered heteroaryl,
in which phenyl and 5- or 6-membered heteroaryl may be substituted by 1 to 3 substituents independently of one another selected from the group consisting of fluorine, chlorine, methyl, ethyl, difluoromethyl, trifluoromethyl, hydroxyl, methoxy, ethoxy, amino, hydroxycarbonyl, methoxycarbonyl and ethoxycarbonyl,
$R^2$ represents phenyl, pyrazolyl or pyridyl,
where phenyl and pyridyl may be substituted by 1 or 2 substituents independently of one another selected from the group consisting of fluorine, chlorine, cyano, hydroxyl, $(C_1-C_4)$-alkyl and $(C_1-C_4)$-alkoxy,
in which $(C_2-C_4)$-alkoxy may be substituted by 1 or 2 substituents independently of one another selected from the group consisting of oxo, hydroxyl, $(C_1-C_4)$-alkoxy, hydroxycarbonyl and amino,
and
where pyrazolyl may be substituted by a substituent selected from the group consisting of fluorine, chlorine, cyano, hydroxyl, $(C_1-C_4)$-alkyl and $(C_1-C_4)$-alkoxy,
in which $(C_2-C_4)$-alkoxy may be substituted by 1 or 2 substituents independently of one another selected from the group consisting of oxo, hydroxyl, $(C_1-C_4)$-alkoxy, hydroxycarbonyl and amino,
and salts, solvates and solvates of the salts thereof.
In the context of the present invention, very particular preference is given to compounds of the formula (I) in which ring Q represents a group of the formula

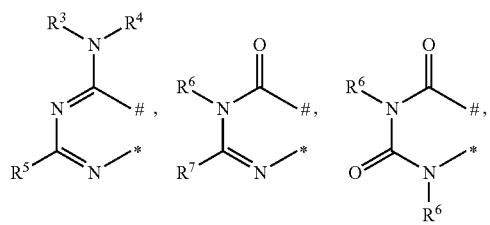

-continued

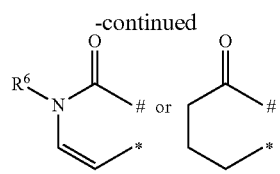

in which
* represents in each case the point of attachment to the C2 atom,
# represents in each case the point of attachment to the C3 atom,
$R^3$ represents hydrogen,
$R^4$ represents hydrogen,
$R^5$ represents methyl,
$R^6$ represents hydrogen, and
$R^7$ represents hydrogen or methyl,
X represents S or O,
$R^1$ represents thiazolyl or oxazolyl,
where thiazolyl and oxazolyl are substituted by a phenyl substituent,
in which phenyl may be substituted by a substituent selected from the group consisting of fluorine, chlorine, cyano, methyl, methoxy, hydroxycarbonyl and methoxycarbonyl, and
where thiazolyl and oxazolyl may be substituted by a substituent selected from the group consisting of fluorine, chlorine, cyano, methyl, ethyl, methoxy, amino, hydroxycarbonyl and methoxycarbonyl,
$R^2$ represents a group of the formula

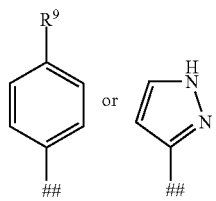

where
## represents the point of attachment to the bicycle,
in which
$R^9$ represents hydrogen or $(C_1-C_4)$-alkoxy,
in which $(C_2-C_4)$-alkoxy may be substituted by 1 or 2 hydroxyl substituents, and salts, solvates and solvates of the salts thereof.
In the context of the present invention, preference is also given to compounds of the formula (I) in which
$R^1$ represents thiazolyl or oxazolyl,
where thiazolyl and oxazolyl are substituted by a phenyl substituent,
in which phenyl may be substituted by a substituent selected from the group consisting of fluorine, chlorine, cyano, methyl, methoxy, hydroxycarbonyl and methoxycarbonyl, and
where thiazolyl and oxazolyl may be substituted by a substituent selected from the group consisting of fluorine, chlorine, cyano, methyl, ethyl, methoxy, amino, hydroxycarbonyl and methoxycarbonyl.
In the context of the present invention, preference is also given to compounds of the formula (I) in which may be substituted, $R^2$ represents a group of the formula

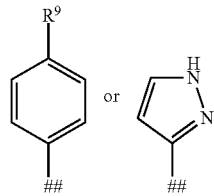

where
## represents the point of attachment to the bicycle,
in which
$R^9$ represents hydrogen or $(C_1-C_4)$-alkoxy,
in which $(C_2-C_4)$-alkoxy may be substituted by 1 or 2 hydroxyl substituents.

The present invention furthermore provides the compound 5,6,7,8-tetrahydro-2-[[(2-methylphenyl)methyl]thio]-4-(2-thienyl)-3-quinolinecarbonitrile, 5,6,7,8-tetrahydro-2-[(2-phenylmethyl)thio]-4-(2-thienyl)-3-quinolinecarbonitrile, 5,6,7,8-tetrahydro-2-[[(2-methylphenyl)methyl]thio]-4-(4-pyridyl)-3-quinolinecarbonitrile, 5,6,7,8-tetrahydro-2-[(phenylmethyl)thio]-4-phenyl-3-quinolinecarbonitrile, 5,6,7,8-tetrahydro-2-[(phenylmethyl)thio]-4-(4-chlorophenyl)-3-quinolinecarbonitrile or 6,7-dihydro-4-(4-hydroxyphenyl)-2-[(phenylmethyl)thio]-5H-cyclopenta[b]pyridine-3-carbonitrile for the prophylaxis and/or treatment of cardiovascular disorders.

The present invention furthermore provides the use of a compound selected from the group consisting of 5,6,7,8-tetrahydro-2-[[(2-methylphenyl)methyl]thio]-4-(2-thienyl)-3-quinolinecarbonitrile, 5,6,7,8-tetrahydro-2-[(2-phenylmethyl)thio]-4-(2-thienyl)-3-quinolinecarbonitrile, 5,6,7,8-tetrahydro-2-[[(2-methylphenyl)methyl]thio]-4-(4-pyridyl)-3-quinolinecarbonitrile, 5,6,7,8-tetrahydro-2-[(phenylmethyl)thio]-4-phenyl-3-quinolinecarbonitrile, 5,6,7,8-tetrahydro-2-[(phenylmethyl)thio]-4-(4-chlorophenyl)-3-quinolinecarbonitrile and 6,7-dihydro-4-(4-hydroxyphenyl)-2-[(phenylmethyl)thio]-5H-cyclopenta[b]pyridine-3-carbonitrile for preparing medicaments or pharmaceutical compositions for the prophylaxis and/or treatment of cardiovascular disorders.

The present invention furthermore provides a process for preparing the compounds of the formula (I) according to the invention, characterized in that [A] a compound of the formula (II)

(II)

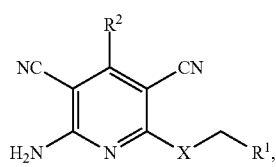

in which X, $R^1$ and $R^2$ each have the meanings given above, is reacted in an inert solvent or in the absence of a solvent with a compound of the formula (III)

(III)

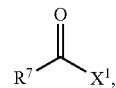

in which $R^7$ has the meaning given above and
$X^1$ represents hydroxyl or $-OC(O)R^7$, in which $R^7$ has the meaning given above, to give a compound of the formula (I-A)

(I-A)

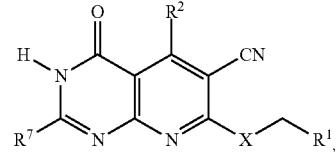

in which X, $R^1$, $R^2$ and $R^7$ each have the meanings given above, or [B] a compound of the formula (II) is reacted in an inert solvent or in the absence of a solvent in the presence of a suitable source of ammonia, such as, for example, ammonium acetate, with a compound of the formula (IV)

(IV)

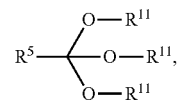

in which $R^5$ has the meaning given above and
$R^{11}$ represents $(C_1-C_4)$-alkyl, to give compounds of the formula (I-B)

(I-B)

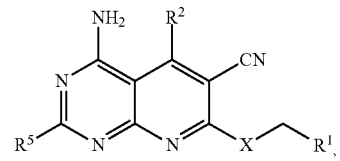

in which X, $R^1$, $R^2$ and $R^5$ each have the meanings given above, or [C] a compound of the formula (V)

(V)

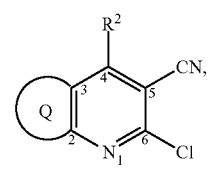

in which $R^2$ has the meaning given above and ring Q represents a group of the formula

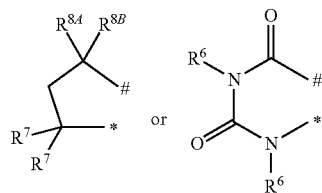

where
* represents in each case the point of attachment to the C2 atom,
# represents in each case the point of attachment to the C3 atom,
$R^6$ represents in each case hydrogen, $(C_1-C_4)$-alkyl or allyl, in which $(C_1-C_4)$-alkyl may be substituted by a substituent selected from the group consisting of hydroxycarbonyl, $(C_1-C_4)$-alkoxycarbonyl and amino,
$R^7$ represents in each case hydrogen or $(C_1-C_4)$-alkyl, and either
i) $R^{8A}$ and $R^{8B}$ represent hydrogen, or
$R^{8A}$ together with $R^{8B}$ forms an oxo group, is reacted in an inert solvent initially with an alkali metal sulfide, such as, for example, sodium sulfide, to give a compound of the formula (VI)

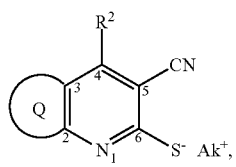
(VI)

in which $R^2$ has the meaning given above,
$Ak^+$ represents an alkali metal salt, preferably a sodium salt, and ring Q represents a group of the formula

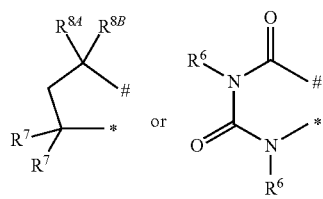

where
* represents in each case the point of attachment to the C2 atom,
# represents in each case the point of attachment to the C3 atom,
$R^6$ represents in each case hydrogen, $(C_1-C_4)$-alkyl or allyl, in which $(C_1-C_4)$-alkyl may be substituted by a substituent selected from the group consisting of hydroxycarbonyl, $(C_1-C_4)$-alkoxycarbonyl and amino,
$R^7$ represents in each case hydrogen or $(C_1-C_4)$-alkyl, and either
i) $R^{8A}$ and $R^{8B}$ represent hydrogen, or
$R^{8A}$ together with $R^{8B}$ forms an oxo group, and this is then reacted in the presence of a suitable base with the compound of the formula (VII)

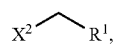
(VII)

in which $R^1$ has the meaning given above and
$X^2$ represents a suitable leaving group, preferably halogen, in particular chlorine, bromine or iodine, or represents mesylate, tosylate or triflate, to give a compound of the formula (I-C)

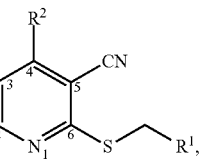
(I-C)

in which $R^1$ and $R^2$ each have the meanings given above, ring Q represents a group of the formula

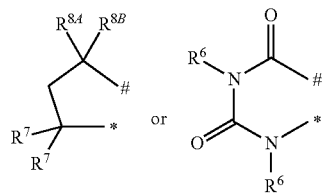

where
* represents in each case the point of attachment to the C2 atom,
# represents in each case the point of attachment to the C3 atom,
$R^6$ represents hydrogen, $(C_1-C_4)$-alkyl or allyl, in which $(C_1-C_4)$-alkyl may be substituted by a substituent selected from the group consisting of hydroxycarbonyl, $(C_1-C_4)$-alkoxycarbonyl and amino,
$R^7$ represents hydrogen or $(C_1-C_4)$-alkyl, and either
i) $R^{8A}$ and $R^{8B}$ represent hydrogen, or
$R^{8A}$ together with $R^{8B}$ forms an oxo group, or [D] a compound of the formula (V) is reacted in an inert solvent in the presence of a base with a compound of the formula (VIII)

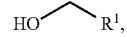
(VIII)

in which $R^1$ has the meaning given above to give compounds of the formula (I-D)

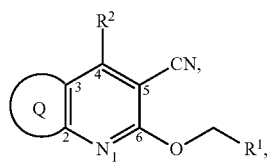
(I-D)

in which $R^1$ and $R^2$ each have the meanings given above, and ring Q represents a group of the formula

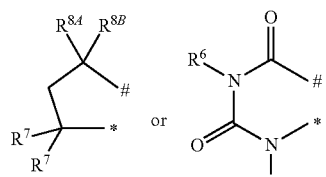

where
* represents in each case the point of attachment to the C2 atom,
# represents in each case the point of attachment to the C3 atom,
$R^6$ represents hydrogen, $(C_1-C_4)$-alkyl or allyl, in which $(C_1-C_4)$-alkyl may be substituted by a substituent selected from the group consisting of hydroxycarbonyl, $(C_1-C_4)$-alkoxycarbonyl and amino,
$R^7$ represents hydrogen or $(C_1-C_4)$-alkyl, and either
i) $R^{8A}$ and $R^{8B}$ represent hydrogen, or
$R^{8A}$ together with $R^{8B}$ forms an oxo group, or [E] a compound of the formula (IX)

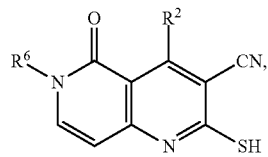

(IX)

in which $R^2$ and $R^6$ each have the meanings given above, is reacted in an inert solvent in the presence of a suitable base with a compound of the formula (VII) to give a compound of the formula (I-E)

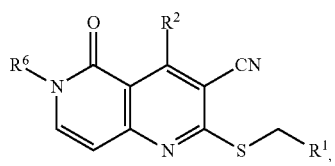

(I-E)

in which $R^1$, $R^2$ and $R^6$ each have the meanings given above, or [F] a compound of the formula (IX) is converted in an inert solvent in the presence of a suitable base with an alkyl halide, such as, for example, methyl iodide, into a compound of the formula (X)

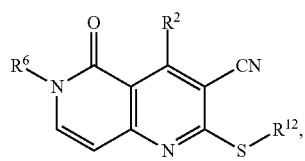

(X)

in which $R^2$ and $R^6$ each have the meanings given above, and $R^{12}$ represents $(C_1-C_4)$-alkyl, and this is then reacted in an inert solvent in the presence of a suitable base with a compound of the formula (VIII) to give a compound of the formula (I-F)

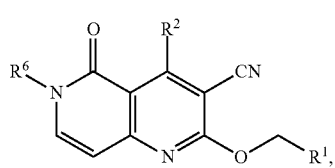

(I-F)

in which $R^1$, $R^2$ and $R^6$ each have the meanings given above, or

[G] a compound of the formula (XI)

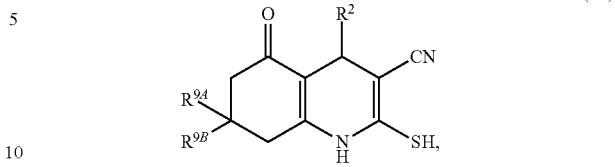

(XI)

in which $R^2$, $R^{9A}$ and $R^{9B}$ each have the meanings given above,
is reacted in an inert solvent in the presence of a suitable base with a compound of the formula (VII) and, if appropriate, with addition of a suitable oxidizing agent, such as, for example, 2,3-dichloro-5,6-dicyano-1,4-benzoquinone, to give a compound of the formula (I-G)

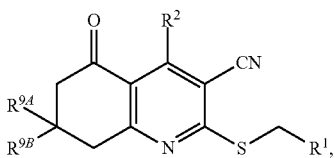

(I-G)

in which $R^1$, $R^2$, $R^{9A}$ and $R^{9B}$ each have the meanings given above, or
[H] a compound of the formula (XI) is converted in an inert solvent in the presence of a suitable base with an alkyl halide, such as, for example, methyl iodide, into a compound of the formula (XII)

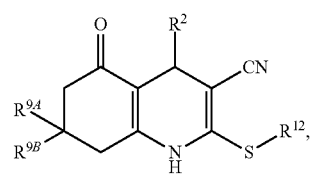

(XII)

in which $R^2$, $R^{9A}$ and $R^{9B}$ each have the meanings given above,
and
$R^{12}$ represents $(C_1-C_4)$-alkyl,
and this is then reacted in an inert solvent in the presence of a suitable base with a compound of the formula (VIII), if appropriate with addition of a suitable oxidizing agent, such as, for example, 2,3-dichloro-5,6-dicyano-1,4-benzoquinone, to give a compound of the formula (I-H)

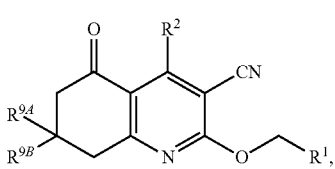

(I-H)

in which $R^1$, $R^2$, $R^{9A}$ and $R^{9B}$ each have the meanings given above, any protective groups present are then cleaved off and the resulting compounds of the formulae (I-A), (I-B), (I-C), (I-D), (I-E), (I-F), (I-G) and (I-H) are, if appropriate, converted with the appropriate (i) solvents and/or (ii) bases or acids into their solvates, salts and/or solvates of the salts.

Any functional groups which may be present in the compounds of the formulae (II), (V), (IX), (X), (XI) and (XII) or in the radicals $R^2$, $R^4$, $R^5$, $R^6$, $R^7$ and/or $R^{8A}$—such as, in particular, amino, hydroxyl and carboxyl groups—may in this process, if expedient or required, also be present in temporarily protected form. The introduction and removal of such protective groups takes place in this connection by conventional methods known to the person skilled in the art [see, for example, T. W. Greene and P. G. M. Wuts, Protective Groups in Organic Synthesis, Wiley, New York, 1999; M. Bodanszky and A. Bodanszky, The Practice of Peptide Synthesis, Springer-Verlag, Berlin, 1984]. If a plurality of protective groups is present, the removal may optionally be carried out simultaneously in a one-pot reaction or in separate reaction steps.

Other compounds according to the invention can be prepared from the compounds, obtained by the above processes, of the formula (I) in which
Q represents a group of the formula

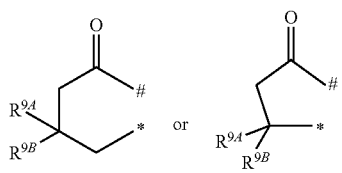

in which #, *, $R^{9A}$ and $R^{9B}$ each have the meanings given above,
by converting these analogously to the process described in Hayakawa M. et al., Bioorg. Med. Chem. 2006, 14 (20), 6847-6858 into compounds of the formula (XIII),

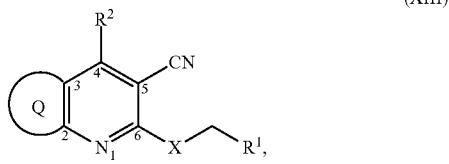

(XIII)

in which X, $R^1$ and $R^2$ have the meanings given above, and $Q_1$ represents a group of the formula

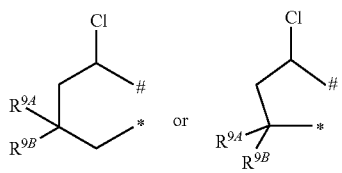

in which #, *, $R^{9A}$ and $R^{9B}$ have the meanings given above, and then reacting these compounds further analogously to processes known from the literature.

Other compounds according to the invention can, if appropriate, also be prepared from the compounds, obtained by the above processes, (I-A), (I-B), (I-C), (I-D), (I-E), (I-F), (I-G) and (I-H) by converting functional groups of individual substituents, in particular those listed under $R^2$ and Q. These conversions are carried out by customary methods known to the person skilled in the art and include, for example, reactions such as nucleophilic and electrophilic substitutions, oxidations, reductions, hydrogenations, transition metal-catalyzed coupling reactions, eliminations, alkylation, amination, esterification, ester cleavage, etherification, ether cleavage, formation of carboxamides, and also the introduction and removal of temporary protective groups.

Other compounds of the formula (I) according to the invention in which Q represents a group of the formula

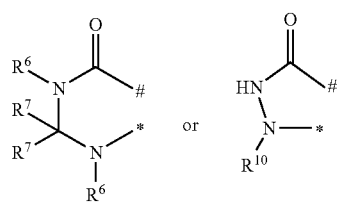

in which $R^6$, $R^7$ and $R^{10}$ have the meanings given above, can be prepared analogously to processes known from the literature [cf., for example, Ghattas A.-B. A. G. et al., Phosphorus, Sulfur, and Silicon 2003, 178, 1781-1794 and Monge A. et al., J. Heterocycl. Chem. 1992, 29, 1545-1549].

The compounds of the formulae (III) and (IV) are commercially available or known from the literature, or they can be prepared analogously to processes known from the literature.

The compounds of the formula (VII) are commercially available or known from the literature, or they can be prepared by methods known from the literature. Thus, substituted oxazole and thiazole derivatives of the formulae (VII-A) and (VII-B) can be obtained, for example, by reaction of amides, thioamides or thiourea derivatives with a 1,3-dihaloacetone (see Scheme 1):

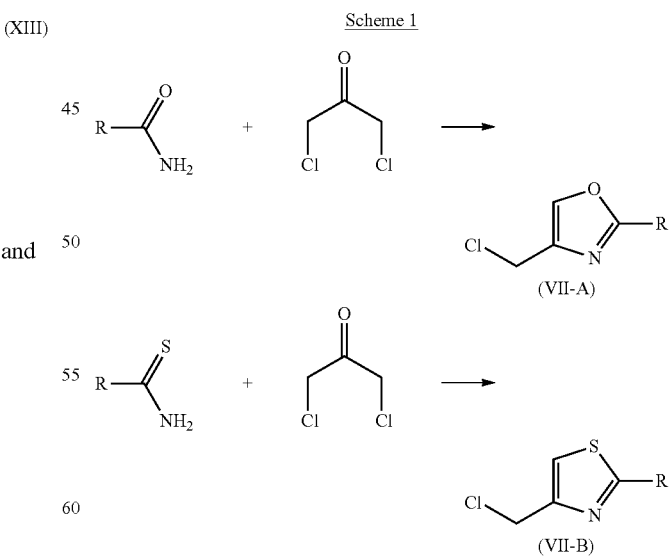

Scheme 1

The compounds of the formula (VIII) are commercially available or known from the literature, or they can be prepared by methods known from the literature. [cf., for example, M. Suzuki et al., J. Org. Chem. 1973, 38, 3571-3575; E. A.

Krasnokutskaya et al., Synthesis 2007, 1, 81-84; J. Hassan et al., Chem. Rev. 2002, 102, 1359-1469].

The compounds of the formula (II) in which X represents S can be prepared by reacting a compound of the formula (XIV)

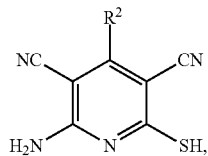
(XIV)

in which $R^2$ has the meaning given above,
in an inert solvent in the presence of a base with a compound of the formula (VII)
to give compounds of the formula (II-A)

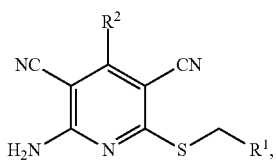
(II-A)

in which $R^1$ and $R^2$ each have the meanings given above.

Compounds of the formula (XIV) can be prepared analogously to methods known from the literature for example by reacting aldehydes of the formula (XV)

(XV)

in which $R^2$ has the meaning given above,
in the presence of a base with two equivalents of cyanothioacetamide [cf., for example, Dyachenko et al., Russ. J. Chem. 1997, 33 (7), 1014-1017, 1998, 34 (4), 557-563; Dyachenko et al., Chemistry of Heterocyclic Compounds 1998, 34 (2), 188-194; Qintela et al., Eur. J. Med. Chem. 1998, 33, 887-897; Kandeel et al., Z. Naturforsch. 1987, 42b, 107-111; Reddy et al., J. Med. Chem. 2006, 49, 607-615; Evdokimov et al., Org. Lett. 2006, 8, 899-902].

The compounds of the formula (XV) are commercially available or known from the literature, or they can be prepared analogously to processes known from the literature. Compounds of the formula (II) in which X represents O can be prepared by reacting a compound of the formula (XVI)

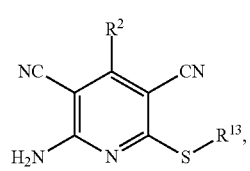
(XVI)

in which $R^2$ has the meaning given above, and
$R^{13}$ represents $(C_1-C_4)$-alkyl or phenyl, in an inert solvent in the presence of a base with a compound of the formula (VIII) to give compounds of the formula (II-B)

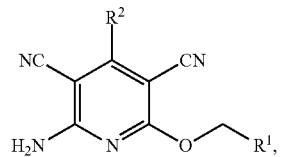
(II-B)

in which $R^1$ and $R^2$ each have the meanings given above.

The compounds of the formula (XVI) can be prepared analogously to processes described in the literature [cf., for example, Kambe et al., Synthesis 1981, 531-533; Elnagdi et al., Z. Naturforsch. 1991, 47b, 572-578; Reddy et al., J. Med. Chem. 2006, 49, 607-615; Evdokimov et al., Org. Lett. 2006, 8, 899-902; Su et al., J. Med Chem. 1988, 31, 1209-1215].

The compounds of the formula (V) can be prepared by reacting a compound of the formula (XVII)

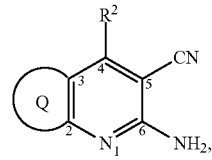
(XVII)

in which Q and $R^2$ have the meanings given above,
in an inert solvent with copper(II) chloride and isopentyl nitrite.

The compounds (XVII) are known from the literature or can be prepared analogously to processes known from the literature [cf., for example, Assy et al., J. Indian. Chem. Soc. 1996, 73(11), 623-624 and Kambe et al., Synthesis 1980, 5, 366-368].

The compounds of the formula (IX) can be prepared by reacting a compound of the formula (XVIII)

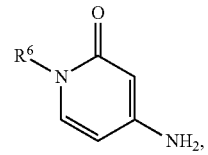
(XVIII)

in which $R^6$ has the meaning given above,
in an inert solvent with a compound of the formula (XV) and cyanothioacetamide in the presence of a suitable acid [cf., for example, Dyachenko et al., Russ. J. Chem. 1997, 33 (7), 1014-1017, 1998, 34 (4), 557-563; Dyachenko et al., Chemistry of Heterocyclic Compounds 1998, 34 (2), 188-194; Qintela et al., Eur. J. Med. Chem. 1998, 33, 887-897; Kandeel et al., Z. Naturforsch. 1987, 42b, 107-111; Reddy et al., J. Med. Chem. 2006, 49, 607-615; Evdokimov et al., Org. Lett. 2006, 8, 899-902].

The compounds of the formula (XVIII) are commercially available or known from the literature, or they can be prepared analogously to processes known from the literature.

The compounds of the formula (XI) can be prepared by reacting a compound of the formula (XIX)

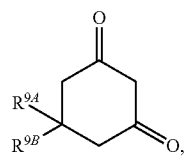
(XIX)

in which $R^{9A}$ and $R^{9B}$ have the meanings given above,
in an inert solvent with a compound of the formula (XV) and cyanothioacetamide in the presence of a suitable base [cf., for example, Dyachenko et al., Russ. J. Chem. 1997, 33 (7), 1014-1017, 1998, 34 (4), 557-563; Dyachenko et al., Chemistry of Heterocyclic Compounds 1998, 34 (2), 188-194; Qintela et al., Eur. J. Med. Chem. 1998, 33, 887-897; Kandeel et al., Z. Naturforsch. 1987, 42b, 107-111; Reddy et al., J. Med. Chem. 2006, 49, 607-615; Evdokimov et al., Org. Lett. 2006, 8, 899-902].

The compounds of the formula (XIX) are commercially available or known from the literature, or they can be prepared analogously to processes known from the literature. The compounds 5,6,7,8-tetrahydro-2-[[(2-methylphenyl)methyl]thio]-4-(2-thienyl)-3-quinolinecarbonitrile, 5,6,7,8-tetrahydro-2-[(2-phenylmethyl)thio]-4-(2-thienyl)-3-quinolinecarbonitrile, 5,6,7,8-tetrahydro-2-[[(2-methylphenyl)methyl]thio]-4-(4-pyridyl)-3-quinolinecarbonitrile, 5,6,7,8-tetrahydro-2-[(phenylmethyl)thio]-4-phenyl-3-quinolinecarbonitrile, 5,6,7,8-tetrahydro-2-[(phenylmethyl)thio]-4-(4-chlorophenyl)-3-quinolinecarbonitrile and 6,7-dihydro-4-(4-hydroxyphenyl)-2-[(phenylmethyl)thio]-5H-cyclopenta[b]pyridine-3-carbonitrile can be prepared analogously to the preparation process mentioned above or to processes known from the literature [cf., for example, Rodinovskaya et al., Synthesis 2006, 14, 2357-2370; Dyachenko et al., Chemistry of Heterocyclic Compounds 1997, 33 (10), 1203-1208; Awad et al., Phosphorus, Sulfur and Silicon 1991, 57, 293-301; Dyachenko V. D., Ukrainskii Khimicheskii Zhournal (Russian Edition) 2006, 72 (1-2), 116-120].

Inert solvents for the reactions (II)+(III)→(I-A) and (II)+(IV)→(I-B), are, for example, acyclic and cyclic ethers, such as 1,2-dimethoxyethane, tetrahydrofuran and dioxane, hydrocarbons, such as benzene, toluene, xylene, hexane and cyclohexane, or other solvents, such as dimethylformamide (DMF), dimethyl sulfoxide (DMSO), N-methylpyrrolidinone (NMP), acetonitrile or pyridine. It is also possible to use mixtures of the solvents mentioned. Preference is given to using the solvent tetrahydrofuran. The reaction is generally carried out in a temperature range of from 0° C. to +160° C., preferably in the range from +20° C. to +140° C., in particular at +50° C. to +140° C., if appropriate in a microwave. The reaction can be carried out at atmospheric, elevated or reduced pressure (for example in the range from 0.5 to 5 bar). The reaction is generally carried out at atmospheric pressure.

Inert solvents for the reactions (VI)+(VII)→(I-C), (IX)+(VII)→(I-E), (XI)+(VII)→(I-G) and (XIII)+(VII)→(II-A) are, for example, alcohols, such as methanol, ethanol, n-propanol, isopropanol, n-butanol and tert-butanol, ketones, such as acetone and methyl ethyl ketone, acyclic and cyclic ethers, such as diethyl ether, methyl tert-butyl ether, 1,2-dimethoxyethane, tetrahydrofuran and dioxane, esters, such as ethyl acetate or butyl acetate, hydrocarbons, such as benzene, toluene, xylene, hexane and cyclohexane, chlorinated hydrocarbons, such as dichloromethane, trichloromethane and chlorobenzene, or other solvents, such as dimethylformamide (DMF), dimethyl sulfoxide (DMSO), N-methylpyrrolidinone (NMP), acetonitrile or pyridine. Water is also suitable as solvent. It is also possible to use mixtures of the solvents mentioned. Preference is given to using the solvent dimethylformamide.

Suitable bases for the reaction (VI)+(VII)→(I-C), (IX)+(VII)→(I-E) and (XI)+(VII)→(I-G) are the customary inorganic or organic bases. These preferably include alkali metal hydroxides, such as lithium hydroxide, sodium hydroxide or potassium hydroxide, alkali metal carbonates, such as lithium carbonate, sodium carbonate, potassium carbonate or cesium carbonate, alkali metal bicarbonates, such as sodium bicarbonate or potassium bicarbonate, alkali metal alkoxides, such as sodium methoxide or potassium methoxide, sodium ethoxide or potassium ethoxide or potassium tert-butoxide, amides, such as sodium amide, lithium bis(trimethylsilyl)amide, sodium bis(trimethylsilyl)amide or potassium bis(trimethylsilyl)amide or lithium diisopropylamide, organometallic compounds, such as butyllithium or phenyllithium, or organic amines, such as triethylamine, diisopropylethylamine, pyridine, 1,8-diazabicyclo[5.4.0]undec-7-ene (DBU) or 1,5-diazabicyclo[4.3.0]non-5-ene (DBN). Preference is given to alkali metal carbonates and alkali metal bicarbonates.

Here, the base can be employed in an amount of from 1 to 10 mol, preferably from 1 to 5 mol, in particular from 1 to 4 mol, based on 1 mol of the compound of the formula (VII). The reaction is generally carried out in a temperature range of from −78° C. to +140° C., preferably in the range from −20° C. to +80° C., in particular at from 0° C. to +50° C., if appropriate in a microwave. The reaction can be carried out at atmospheric, elevated or reduced pressure (for example in the range from 0.5 to 5 bar). The reaction is generally carried out at atmospheric pressure.

Suitable inert solvents for the reactions (V)+(VIII)→(I-D), (X)+(VIII)→(I-F) and (XII)+(VIII)→(I-H) are in particular acyclic and cyclic ethers, such as diethyl ether, methyl tert-butyl ether, 1,2-dimethoxyethane, tetrahydrofuran and dioxane, hydrocarbons, such as benzene, toluene, xylene, hexane and cyclohexane, or other solvents, such as dimethylformamide (DMF), dimethyl sulfoxide (DMSO), N-methylpyrrolidinone (NMP) and pyridine. It is also possible to use mixtures of these solvents. Preference is given to using 1,2-dimethoxyethane.

Suitable bases for the reactions (V)+(VIII)→(I-D), (X)+(VIII)→(I-F) and (XII)+(VIII)→(I-H) are in particular alkali metal alkoxides, such as sodium methoxide or potassium methoxide, sodium ethoxide or potassium ethoxide or sodium tert-butoxide or potassium tert-butoxide, amides, such as sodium amide, lithium bis(trimethylsilyl)amide, sodium bis(trimethylsilyl)amide or potassium bis(trimethylsilyl)amide or lithium diisopropylamide, or organometallic compounds, such as butyllithium or phenyllithium. Preference is given to using potassium tert-butoxide.

Here, the base is generally employed in an amount of from 1 to 1.25 mol, preferably in an equimolar amount, based on 1 mol of the compound of the formula (VIII). The reactions (V)+(VIII)→(I-D), (X)+(VIII)→(I-F) and (XII)+(VIII)→(I-H) are generally carried out in a temperature range of from −20° C. to +120° C., preferably at from +20° C. to +100° C., if appropriate in a microwave. The reactions can be carried out at atmospheric, elevated or reduced pressure (for example in the range from 0.5 to 5 bar). The reactions are generally carried out at atmospheric pressure.

The alkali metal sulfide used for the reaction (V)→(VI) is preferably sodium sulfide in an amount of from 1 to 10 mol, preferably from 1 to 5 mol, in particular from 1 to 4 mol, based on 1 mol of the compound of the formula (V).

Suitable solvents for the reaction (V)→(VI) are all organic solvents which are inert under the reaction conditions. These preferably include dimethylformamide, N-methylpyrrolidinone, pyridine and acetonitrile. It is also possible to use mixtures of the solvents mentioned. Particular preference is given to dimethylformamide The reaction (V)→(VI) is generally carried out in a temperature range of from +20° C. to +140° C., preferably in the range from +20° C. to +120° C., in particular at from +60° C. to +100° C. The reaction can be carried out at atmospheric, elevated or reduced pressure (for example in the range from 0.5 to 5 bar). The reaction is generally carried out at atmospheric pressure.

The reaction (XVI)→(V) is generally carried at in a molar ratio of from 2 to 12 mol of copper(II) chloride and 2 to 12 mol of isopentyl nitrite, based on 1 mol of the compound of the formula (I-A).

Suitable solvents for the process step (XVI)→(V) are all organic solvents which are inert under the reaction conditions. These include acyclic and cyclic ethers, such as diethyl ether and tetrahydrofuran, esters, such as ethyl acetate or butyl acetate, hydrocarbons, such as benzene, toluene, xylene, hexane and cyclohexane, chlorinated hydrocarbons, such as dichloromethane, 1,2-dichloroethane and chlorobenzene, or other solvents, such as dimethylformamide, acetonitrile or pyridine. It is also possible to use mixtures of the solvents mentioned. Preferred solvents are acetonitrile and dimethylformamide.

The reaction is generally carried out in a temperature range of from −78° C. to +180° C., preferably in the range from 0° C. to +100° C., in particular at from +20° C. to +80° C., if appropriate in a microwave. The reaction can be carried out at atmospheric, elevated or reduced pressure (for example in the range from 0.5 to 5 bar). The reaction is generally carried out at atmospheric pressure.

The alkyli metal halide used for the reactions (IX)→(X) and (XI)→(XII) is preferably methyl iodide in an amount of from 1 to 10 mol, preferably from 1 to 5 mol, in particular from 1 to 4 mol, based on 1 mol of the compound of the formula (V). Inert solvents for the reactions (IX)→(X) and (XI)→(XII) are, for example, acyclic and cyclic ethers, such as diethyl ether, methyl tert-butyl ether, 1,2-dimethoxyethane, tetrahydrofuran and dioxane, hydrocarbons, such as benzene, toluene, xylene, hexane and cyclohexane, chlorinated hydrocarbons, such as dichloromethane, trichloromethane and chlorobenzene, or other solvents, such as dimethylformamide (DMF), dimethyl sulfoxide (DMSO), N-methylpyrrolidinone (NMP), acetonitrile or pyridine. It is also possible to use mixtures of the solvents mentioned. Preference is given to using the solvent dimethylformamide.

Suitable bases for the reaction (IX)→(X) and (XI)→(XII) are the customary inorganic or organic bases. These preferably include alkali metal carbonates, such as lithium carbonate, sodium carbonate, potassium carbonate or cesium carbonate, alkali metal bicarbonates, such as sodium bicarbonate or potassium bicarbonate, alkali metal alkoxides, amides, such as sodium amide, lithium bis(trimethylsilyl)amide, sodium bis(trimethylsilyl)amide or potassium bis(trimethylsilyl)amide or lithium diisopropylamide, organometallic compounds, such as butyllithium or phenyllithium, or organic amines, such as triethylamine, diisopropylethylamine, pyridine, 1,8-diazabicyclo[5.4.0]undec-7-ene (DBU) or 1,5-diazabicyclo[4.3.0]non-5-ene (DBN). Preference is given to alkali metal carbonates and alkali metal bicarbonates.

Here, the base can be employed in an amount of from 1 to 10 mol, preferably from 1 to 5 mol, in particular from 1 to 4 mol, based on 1 mol of the compound of the formula (IX) or (XI).

The reaction is generally carried out in a temperature range of from −78° C. to +140° C., preferably in the range from −20° C. to +80° C., in particular at from 0° C. to +50° C., if appropriate in a microwave. The reaction can be carried out at atmospheric, elevated or reduced pressure (for example in the range from 0.5 to 5 bar). The reaction is generally carried out at atmospheric pressure.

The process described above can be illustrated by Reaction Schemes 2 to 13 below:

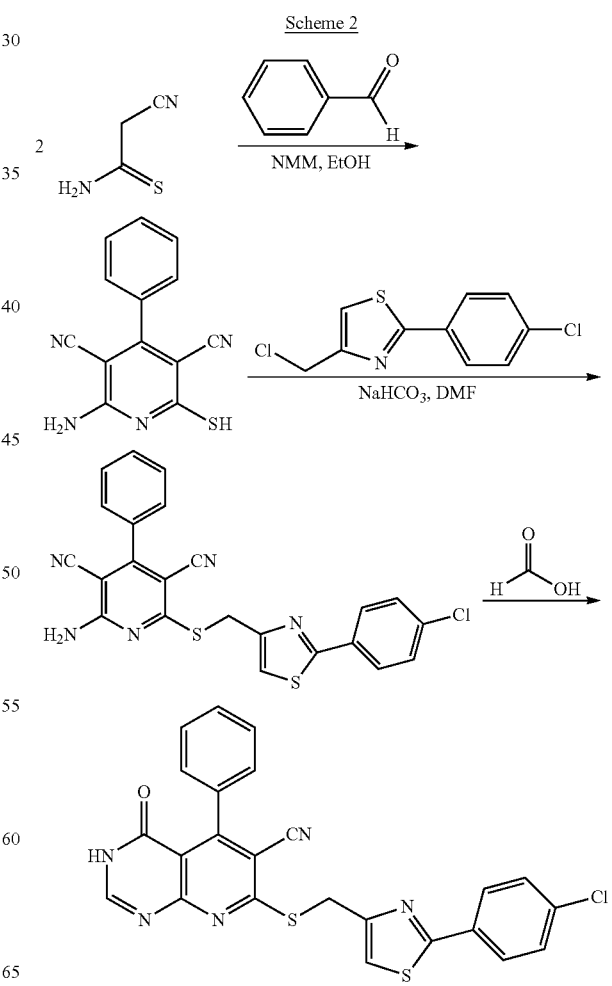

Scheme 3
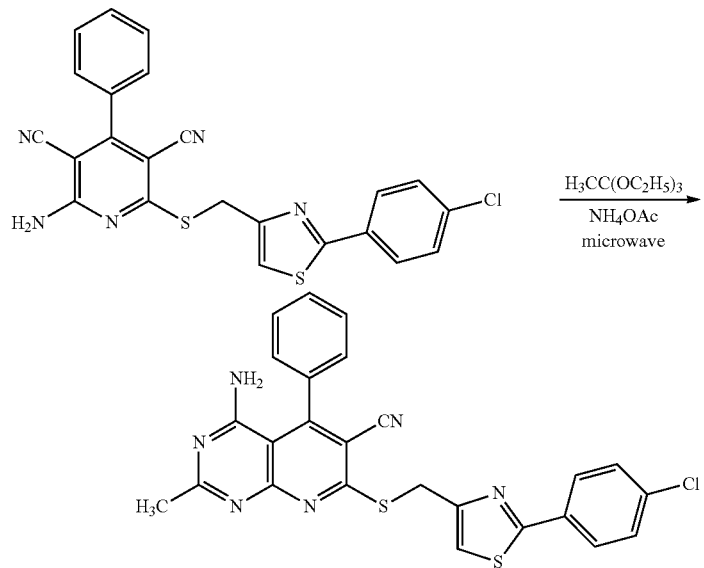
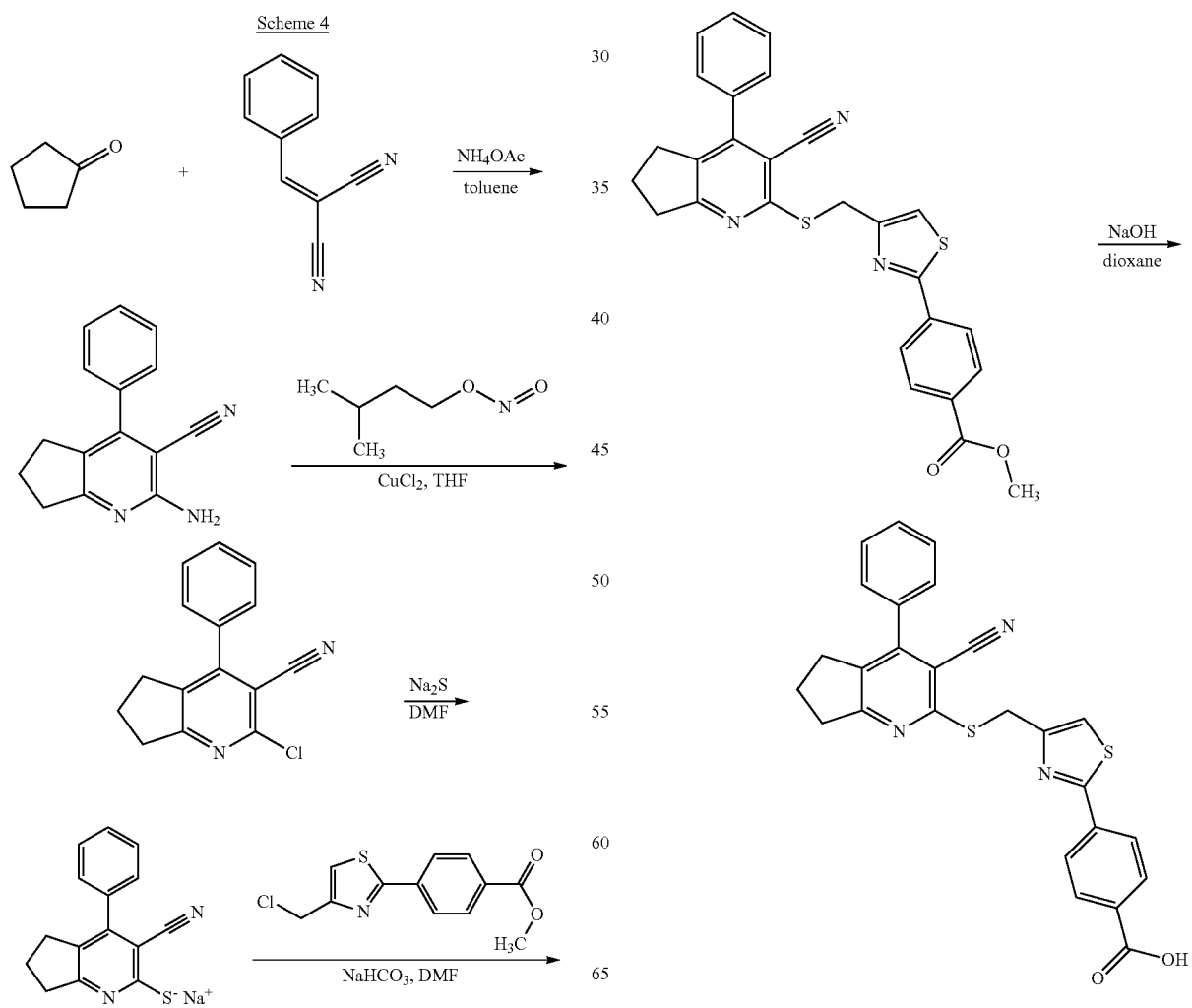

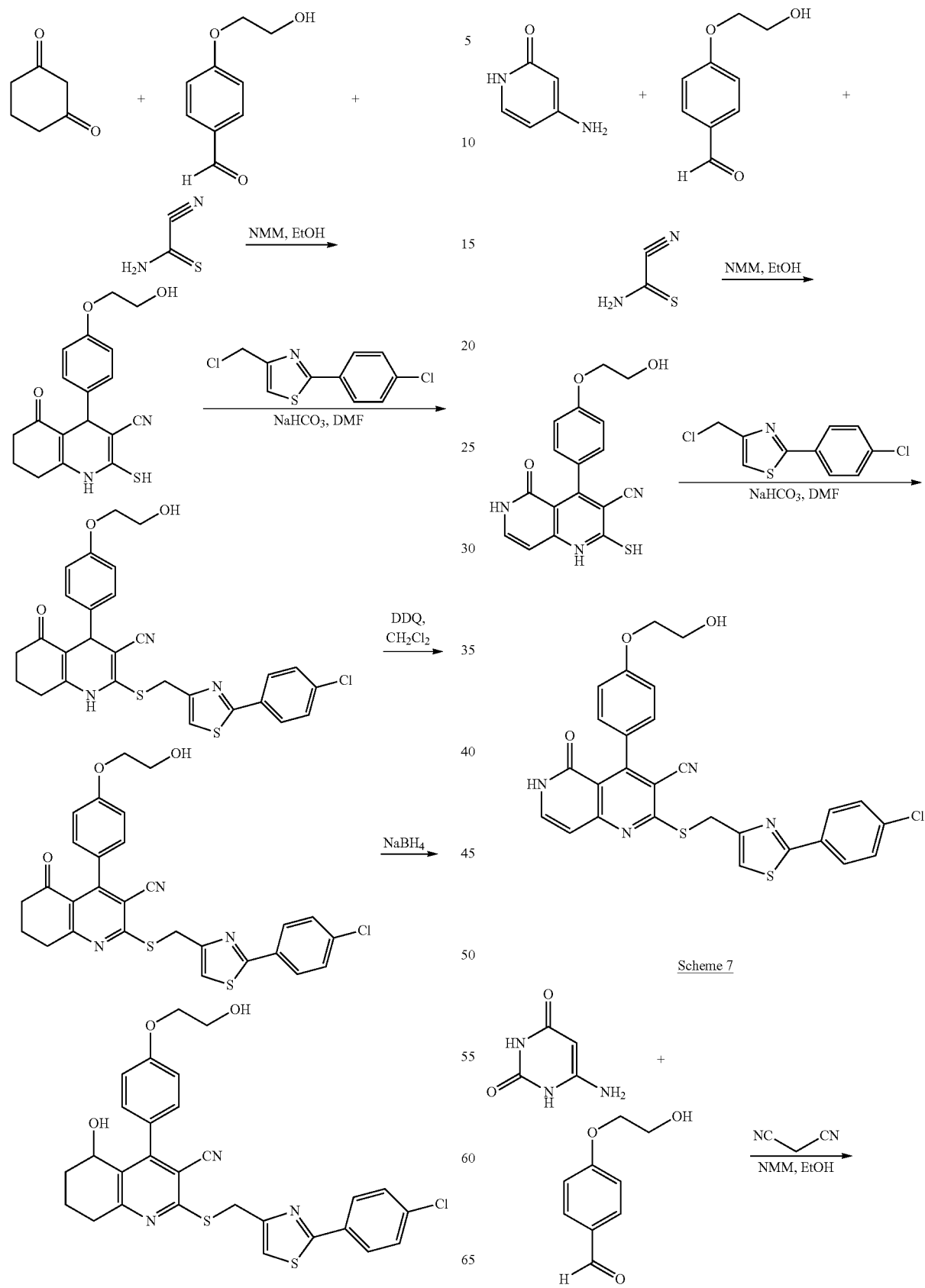

Scheme 9
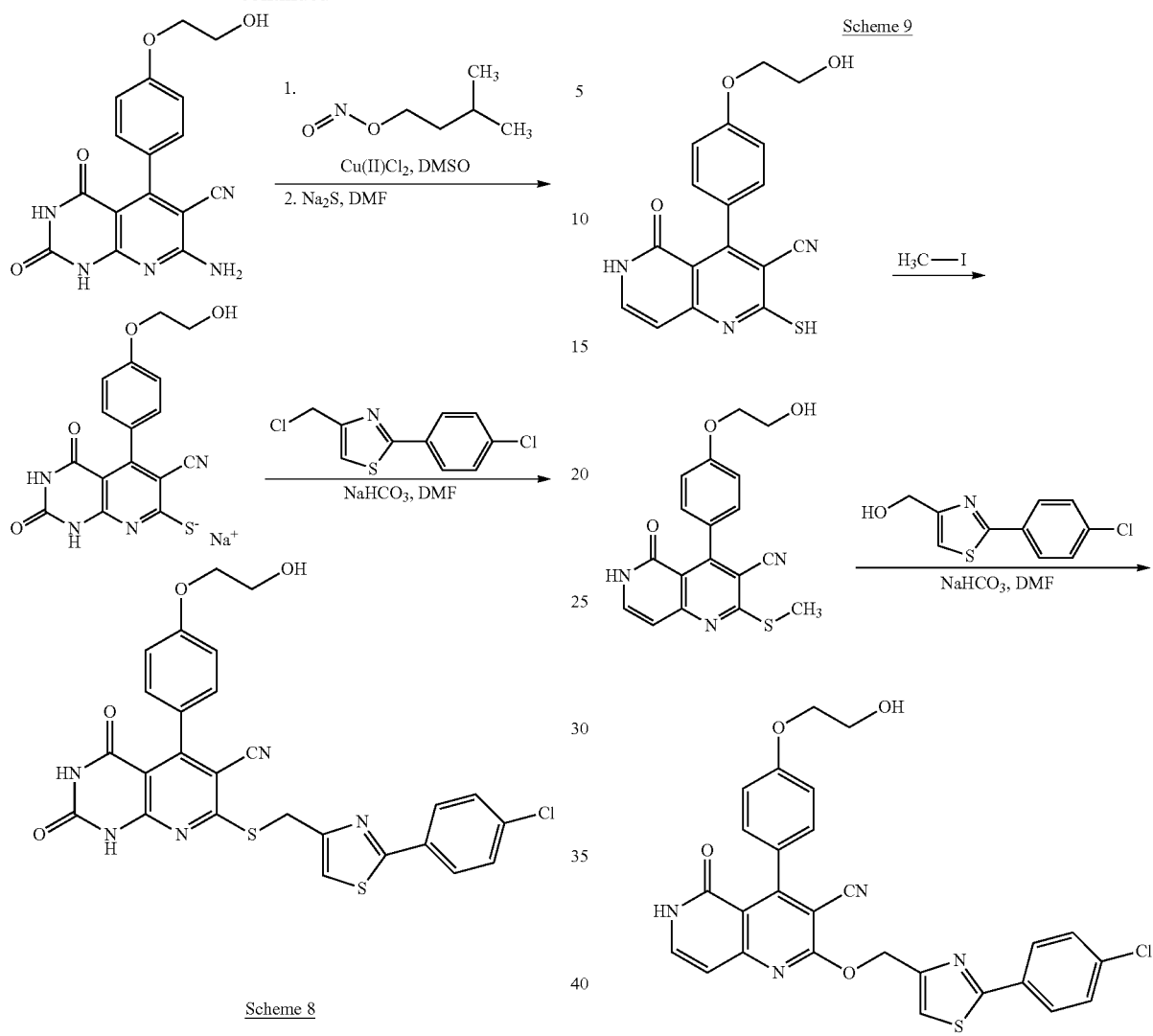
Scheme 8
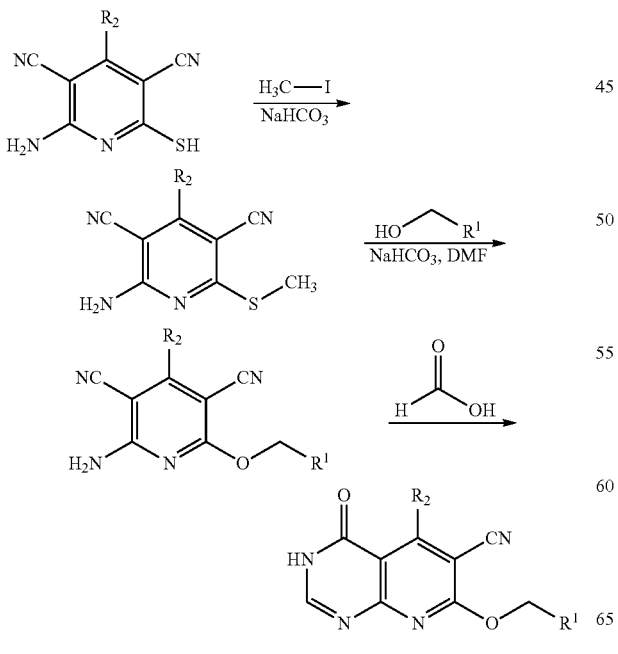
Scheme 10
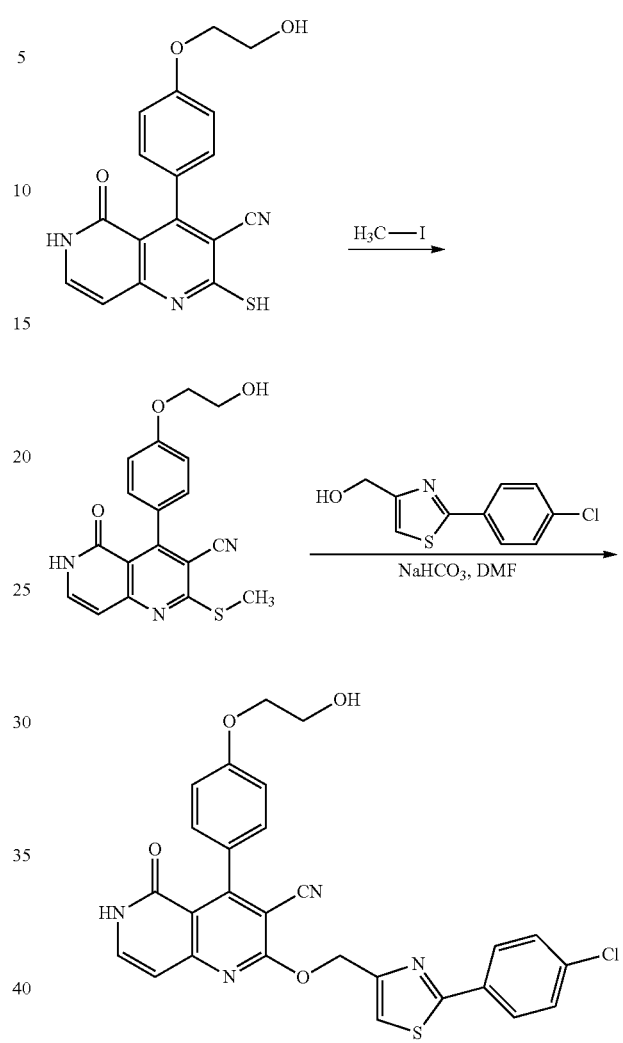

-continued

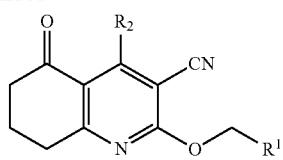

Scheme 11

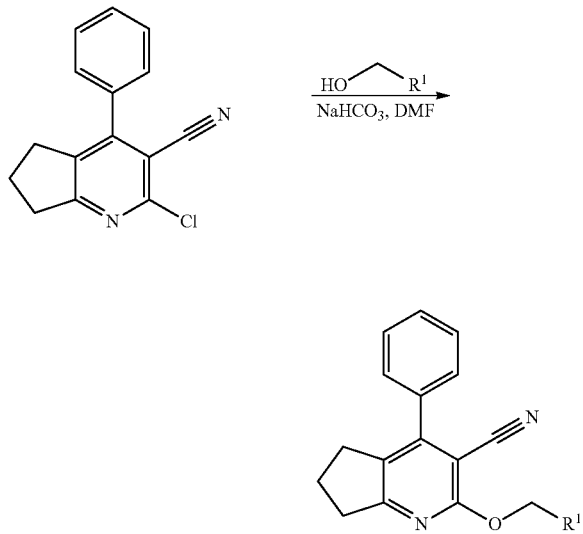

Scheme 12

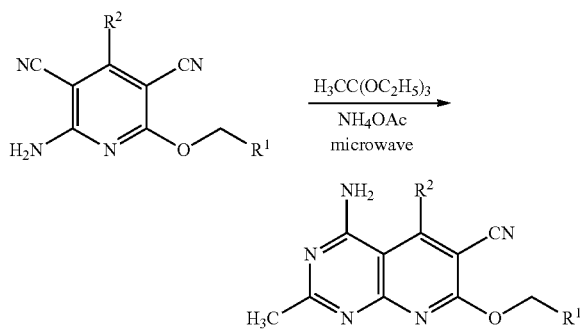

Scheme 13

-continued

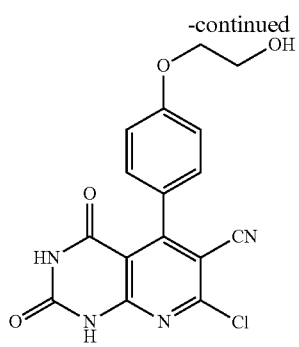

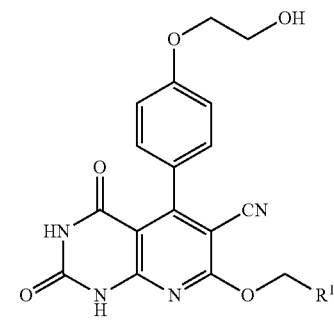

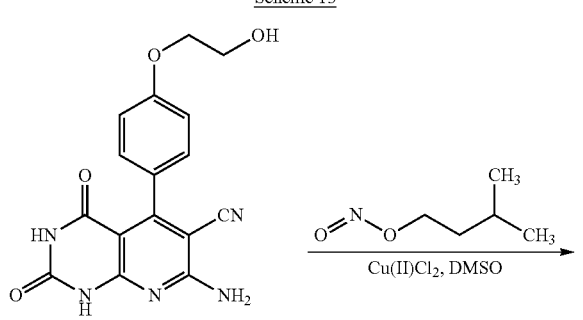

Surprisingly, the compounds according to the invention have an unforeseeable useful pharmacological activity spectrum and are therefore particularly suitable for the prevention and/or treatment of disorders.

The pharmaceutical activity of the compounds according to the invention can be explained by their action as potent, selective ligands at individual subtypes or a plurality of subtypes of adenosine receptors, in particular as selective ligands at adenosine A1 and/or A2b receptors. Here, they act as selective A1 agonists, as selective A1 antagonists or as selective dual A1/A2b agonists.

The compounds according to the invention act mainly as selective adenosine A1 agonists.

In the context of the present invention, "selective ligands at adenosine A1 and/or A2b receptors" are adenosine receptor ligands where firstly a marked activity at A1 and/or A2b adenosine receptor subtypes and secondly no or a considerably weaker activity (by a factor of 10 or more) at A2a and A3 adenosine receptor subtypes can be observed, where with respect to the test methods for activity/selectivity, reference is made to the tests described in section B-1.

Depending on their particular structure, the compounds according to the invention can act as full or as partial adenosine receptor agonists or as adenosine receptor antagonists. Partial adenosine receptor agonists are defined here as receptor ligands which trigger a functional response at adenosine receptors which is less than that of full agonists (such as, for example, adenosine itself). Accordingly, partial agonists have lower activity with respect to receptor activation than full agonists.

The compounds of the formula (I) are suitable alone or in combination with one or more other active ingredients for the prevention and/or treatment of various disorders, for example in particular hypertension and other disorders of the cardiovascular system (cardiovascular disorders), for cardio protection following lesions of the heart, and of metabolic disorders and kidney disorders.

In the context of the present invention, disorders of the cardiovascular system or cardiovascular disorders are to be understood as including, in addition to hypertension, for example the following disorders: peripheral and cardial vascular disorders, coronary heart disease, coronary restenosis, such as, for example, restenosis after balloon dilation of peripheral blood vessels, myocardial infarction, acute coronary syndrome, stable and unstable angina pectoris, heart failure, tachycardias, arrhythmias, atrial and ventricular fibrillation, impaired peripheral circulation, elevated levels of fibrinogen and of low density LDL, and elevated concentrations of plasminogen activator inhibitor 1 (PAI-1), especially coronary heart disease, acute coronary syndrome, angina pectoris, heart failure, myocardial infarction, atrial fibrillation and hypertension. In the context of the present invention, the term heart failure includes both acute and chronic manifestations of heart failure, as well as more specific or related types of disease, such as acute decompensated heart failure, right heart failure, left heart failure, global failure, ischemic cardiomyopathy, dilated cardiomyopathy, congenital heart defects, heart valve defects, heart failure associated with heart valve defects, mitral stenosis, mitral insufficiency, aortic stenosis, aortic insufficiency, tricuspid stenosis, tricuspid insufficiency, pulmonary stenosis, pulmonary valve insufficiency, combined heart valve defects, myocardial inflammation (myocarditis), chronic myocarditis, acute myocarditis, viral myocarditis, diabetic heart failure, alcoholic cardiomyopathy, cardiac storage disorders, and diastolic and systolic heart failure.

The compounds according to the invention are furthermore also suitable for reducing the myocard region affected by an infarct, and also for the prevention of secondary infarcts.

The compounds according to the invention are furthermore suitable for the prevention and/or treatment of thromboembolic disorders, reperfusion damage following ischemia, micro- and macrovascular lesions (vasculitis), edemas, ischemias such as myocardial infarction, stroke and transient ischemic attacks, and for organ protection in connection with transplants, bypass operations, catheter heart examinations and other surgical procedures.

Furthermore, the compounds according to the invention are suitable for the treatment and/or prevention of kidney diseases, in particular of renal insufficiency. In the context of the present invention, the term renal insufficiency comprises both acute and chronic forms of renal insufficiency, as well as underlying or related kidney diseases such as renal hypoperfusion, obstructive uropathy, glomerulonephritis, acute glomerulonephritis, tubulointerstitial diseases, nephropathic diseases such as primary and congenital kidney disease, nephritis, nephropathy induced by toxic substances, diabetic nephropathy, pyelonephritis, renal cysts and nephrosclerosis, which can be characterized diagnostically for example by abnormally reduced creatinine and/or water excretion, abnormally raised blood concentrations of urea, nitrogen, potassium and/or creatinine, altered activity of renal enzymes, such as, for example, glutamylsynthetase, altered urine osmolarity or urine volume, increased microalbuminuria, macroalbuminuria, lesions on glomeruli and arterioles, tubular dilatation, hyperphosphatemia and/or need for dialysis. The present invention also comprises the use of the compounds according to the invention for the treatment and/or prevention of sequelae of renal insufficiency, for example hypertension, pulmonary edema, heart failure, uraemia, anemia, electrolyte disturbances (for example hyperkalemia, hyponatremia) and disturbances in bone and carbohydrate metabolism.

Further indications for which the compounds according to the invention may be used are, for example, the prevention and/or treatment of disorders of the urogenital system, such as, for example, in irritable bladder, erectile dysfunction and female sexual dysfunction, but in addition also the prevention and/or treatment of inflammatory disorders, such as, for example, inflammatory dermatoses (psoriasis, acne, eczema, neurodermitis, dermatitis, keratitis, formation of scars, formation of warts, frostbites), of disorders of the central nervous system and neurodegenerative disorders (strokes, Alzheimer's disease, Parkinson's disease, dementia, epilepsy, depression, multiple sclerosis), of states of pain, cancerous diseases (skin cancer, liposarcomas, carcinomas of the gastrointestinal tract, the liver, pancreas, lung, kidney, ureter, prostate and the genital tract), and also of nausea and emesis associated with cancer therapies. Other areas of indication are, for example, the prevention and/or treatment of inflammatory and immune disorders (Crohn's disease, ulcerative colitis, lupus erythematodes, rheumatoid arthritis) and respiratory disorders, such as, for example, chronic obstructive pulmonary disease (chronic bronchitis, COPD), asthma, pulmonary emphysema, bronchiectases, cystic fibrosis (mucoviscidosis) and pulmonary hypertension, in particular pulmonary arterial hypertension.

Finally, the compounds according to the invention are also suitable for the prevention and/or treatment of diabetes, in particular diabetes mellitus, gestation diabetes, insulin-dependent diabetes and non-insulin-dependent diabetes, of diabetic sequelae such as, for example, retinopathy, nephropathy and neuropathy, of metabolic disorders (metabolic syndrome, hyperglycemia, hyperinsulinemia, insulin resistance, glucose intolerance, obesity (adipositas)) and also of arteriosclerosis and dyslipidemias (hypercholesterolemia, hypertriglyceridemia, elevated concentrations of postprandial plasma triglycerides, hypoalphalipoproteinemia, combined hyperlipidemias), in particular of diabetes, metabolic syndrome and dyslipidemias.

In addition, the compounds according to the invention can also be used for the treatment and/or prevention of disorders of the thyroid gland (hyperthyreosis), disorders of the pancreas (pancreatitis), fibrosis of the liver, viral diseases (HPV, HCMV, HIV), cachexia, osteoporosis, gout, incontinence, and also for wound healing and angiogenesis.

The present invention furthermore provides the use of the compounds according to the invention for the treatment and/or prevention of disorders, in particular the disorders mentioned above.

The present invention furthermore provides the use of the compounds according to the invention for preparing a medicament for the treatment and/or prevention of disorders, in particular the disorders mentioned above.

The present invention furthermore provides the compounds according to the invention for use in a method for the treatment and/or prophylaxis of coronary heart disease, acute coronary syndrome, angina pectoris, heart failure, myocardial infarction and atrial fibrillation.

The present invention furthermore provides the compounds according to the invention for methods for the treatment and/or prophylaxis of diabetes, metabolic syndrome and dyslipidemias.

The present invention furthermore provides a method for the treatment and/or prevention of disorders, in particular the disorders mentioned above, using an effective amount of at least one of the compounds according to the invention.

The compounds according to the invention can be used alone or, if required, in combination with other active ingredients. The present invention furthermore provides medicaments comprising at least one compound according to the invention and one or more further active ingredients, in particular for the treatment and/or prevention of the disorders mentioned above.

Suitable active ingredients for combination are, by way of example and by way of preference: active ingredients which modulate lipid metabolism, antidiabetics, hypotensive agents, perfusion-enhancing and/or antithrombotic agents, antioxidants, chemokine receptor antagonists, p38-kinase inhibitors, NPY agonists, orexin agonists, anorectics, PAF-AH inhibitors, antiphlogistics (COX inhibitors, LTB$_4$-receptor antagonists), analgesics for example aspirin, antidepressants and other psychopharmaceuticals.

The present invention relates in particular to combinations of at least one of the compounds according to the invention with at least one lipid metabolism-altering active ingredient, antidiabetic, blood pressure reducing active ingredient and/or agent having antithrombotic effects.

The compounds according to the invention can preferably be combined with one or more lipid metabolism-altering active ingredients, by way of example and by way of preference from the group of the HMG-CoA reductase inhibitors, inhibitors of HMG-CoA reductase expression, squalene synthesis inhibitors, ACAT inhibitors, LDL receptor inductors, cholesterol absorption inhibitors, polymeric bile acid adsorbers, bile acid reabsorption inhibitors, MTP inhibitors, lipase inhibitors, LpL activators, fibrates, niacin, CETP inhibitors, PPAR-α, PPAR-γ and/or PPAR-δ agonists, RXR modulators, FXR modulators, LXR modulators, thyroid hormones and/or thyroid mimetics, ATP citrate lyase inhibitors, Lp(a) antagonists, cannabinoid receptor 1 antagonists, leptin receptor agonists, bombesin receptor agonists, histamine receptor agonists and the antioxidants/radical scavengers; antidiabetics mentioned in the Rote Liste 2004/II, chapter 12, and also, by way of example and by way of preference, those from the group of the sulfonylureas, biguanides, meglitinide derivatives, glucosidase inhibitors, inhibitors of dipeptidylpeptidase IV (DPP-IV inhibitors), oxadiazolidinones, thiazolidinediones, GLP 1 receptor agonists, glucagon antagonists, insulin sensitizers, CCK 1 receptor agonists, leptin receptor agonists, inhibitors of liver enzymes involved in the stimulation of gluconeogenesis and/or glycogenolysis, modulators of glucose uptake and also potassium channel openers, such as, for example, those disclosed in WO 97/26265 and WO 99/03861;

hypotensive active ingredients, by way of example and by way of preference from the group of the calcium antagonists, angiotensin AII antagonists, ACE inhibitors, renin inhibitors, beta-receptor blockers, alpha-receptor blockers, aldosterone antagonists, mineralocorticoid receptor antagonists, ECE inhibitors, ACE/NEP inhibitors and the vasopeptidase inhibitors; and/or antithrombotic agents, by way of example and by way of preference from the group of the platelet aggregation inhibitors or the anticoagulants;

diuretics;

vasopressin receptor antagonists;

organic nitrates and NO donors;

compounds with positive inotropic activity;

compounds which inhibit the degradation of cyclic guanosine monophosphate (cGMP) and/or cyclic adenosine monophosphate (cAMP), such as, for example, inhibitors of phosphodiesterases (PDE) 1, 2, 3, 4 and/or 5, in particular PDE 5 inhibitors, such as sildenafil, vardenafil and tadalafil, and also PDE 3 inhibitors, such as milrinone;

natriuretic peptides, such as, for example, "atrial natriuretic peptide" (ANP, anaritide), "B-type natriuretic peptide" or "brain natriuretic peptide" (BNP, nesiritide), "C-type natriuretic peptide" (CNP) and also urodilatin;

agonists of the prostacyclin receptor (IP receptor), such as, by way of example, iloprost, beraprost, cicaprost;

inhibitors of the I$_f$ (funny channel) channel, such as, by way of example, ivabradine;

calcium sensitizers, such as, by way of example and by way of preference, levosimendan;

potassium supplements;

NO-independent, but heme-dependent stimulators of guanylate cyclase, such as, in particular, the compounds described in WO 00/06568, WO 00/06569, WO 02/42301 and WO 03/095451;

NO—and heme-independent activators of guanylate cyclase, such as, in particular, the compounds described in WO 01/19355, WO 01/19776, WO 01/19778, WO 01/19780, WO 02/070462 and WO 02/070510;

inhibitors of human neutrophil elastase (HNE), such as, for example, sivelestat and DX-890 (Reltran);

compounds which inhibit the signal transduction cascade, such as, for example, tyrosine-kinase inhibitors, in particular sorafenib, imatinib, gefitinib and erlotinib; and/or compounds which influence the energy metabolism of the heart, such as, for example, etomoxir, dichloroacetate, ranolazine and trimetazidine.

Lipid metabolism-altering active ingredients are to be understood as meaning, preferably, compounds from the group of the HMG-CoA reductase inhibitors, squalene synthesis inhibitors, ACAT inhibitors, cholesterol absorption inhibitors, MTP inhibitors, lipase inhibitors, thyroid hormones and/or thyroid mimetics, niacin receptor agonists, CETP inhibitors, PPAR-α agonists PPAR-γ agonists, PPAR-δ agonists, polymeric bile acid adsorbers, bile acid reabsorption inhibitors, antioxidants/radical scavengers and also the cannabinoid receptor 1 antagonists.

In a preferred embodiment of the invention, the compounds according to the invention are administered in combination with an HMG-CoA reductase inhibitor from the class of the statins, such as, by way of example and by way of preference, lovastatin, simvastatin, pravastatin, fluvastatin, atorvastatin, rosuvastatin, cerivastatin or pitavastatin.

In a preferred embodiment of the invention, the compounds according to the invention are administered in combination with a squalene synthesis inhibitor, such as, by way of example and by way of preference, BMS-188494 or TAK-475.

In a preferred embodiment of the invention, the compounds according to the invention are administered in combination with an ACAT inhibitor, such as, by way of example and by way of preference, avasimibe, melinamide, pactimibe, eflucimibe or SMP-797.

In a preferred embodiment of the invention, the compounds according to the invention are administered in combination with a cholesterol absorption inhibitor, such as, by way of example and by way of preference, ezetimibe, tiqueside or pamaqueside.

In a preferred embodiment of the invention, the compounds according to the invention are administered in combination with an MTP inhibitor, such as, by way of example and by way of preference, implitapide, BMS-201038, R-103757 or JTT-130.

In a preferred embodiment of the invention, the compounds according to the invention are administered in combination with a lipase inhibitor, such as, by way of example and by way of preference, orlistat.

In a preferred embodiment of the invention, the compounds according to the invention are administered in combination with a thyroid hormone and/or thyroid mimetic, such as, by way of example and by way of preference, D-thyroxine or 3,5,3'-triiodothyronine (T3).

In a preferred embodiment of the invention, the compounds according to the invention are administered in combination with an agonist of the niacin receptor, such as, by way of example and by way of preference, niacin, acipimox, acifran or radecol.

In a preferred embodiment of the invention, the compounds according to the invention are administered in combination with a CETP inhibitor, such as, by way of example and by way of preference, torcetrapib, JTT-705, BAY 60-5521, BAY 78-7499 or CETP vaccine (Avant).

In a preferred embodiment of the invention, the compounds according to the invention are administered in combination with a PPAR-γ agonist, such as, by way of example and by way of preference, pioglitazone or rosiglitazone.

In a preferred embodiment of the invention, the compounds according to the invention are administered in combination with a PPAR-δ agonist, such as, by way of example and by way of preference, GW-501516 or BAY 68-5042.

In a preferred embodiment of the invention, the compounds according to the invention are administered in combination with a polymeric bile acid adsorber, such as, by way of example and by way of preference, cholestyramine, colestipol, colesolvam, CholestaGel or colestimide.

In a preferred embodiment of the invention, the compounds according to the invention are administered in combination with a bile acid reabsorption inhibitor, such as, by way of example and by way of preference, ASBT (=IBAT) inhibitors, such as, for example, AZD-7806, S-8921, AK-105, BARI-1741, SC-435 or SC-635.

In a preferred embodiment of the invention, the compounds according to the invention are administered in combination with an antioxidant/radical scavenger, such as, by way of example and by way of preference, probucol, AGI-1067, BO-653 or AEOL-10150.

In a preferred embodiment of the invention, the compounds according to the invention are administered in combination with a cannabinoid receptor 1 antagonist, such as, by way of example and by way of preference, rimonabant or SR-147778.

Antidiabetics are to be understood as meaning, preferably, insulin and insulin derivatives, and also orally effective hypoglycemic active ingredients. Here, insulin and insulin derivatives include both insulins of animal, human or biotechnological origin and also mixtures thereof. The orally effective hypoglycemic active ingredients preferably include sulfonylureas, biguanides, meglitinide derivatives, glucosidase inhibitors and PPAR-gamma agonists.

In a preferred embodiment of the invention, the compounds according to the invention are administered in combination with insulin.

In a preferred embodiment of the invention, the compounds according to the invention are administered in combination with a sulfonylurea, such as, by way of example and by way of preference, tolbutamide, glibenclamide, glimepiride, glipizide or gliclazide.

In a preferred embodiment of the invention, the compounds according to the invention are administered in combination with a biguanide, such as, by way of example and by way of preference, metformin.

In a preferred embodiment of the invention, the compounds according to the invention are administered in combination with a meglitinide derivative, such as, by way of example and by way of preference, repaglinide or nateglinide.

In a preferred embodiment of the invention, the compounds according to the invention are administered in combination with a glucosidase inhibitor, such as, by way of example and by way of preference, miglitol or acarbose.

In a preferred embodiment of the invention, the compounds according to the invention are administered in combination with a DPP-IV inhibitor, such as, by way of example and by way of preference, sitagliptin and vildagliptin.

In a preferred embodiment of the invention, the compounds according to the invention are administered in combination with a PPAR-gamma agonist, for example from the class of the thiazolinediones, such as, by way of example and by way of preference, pioglitazone or rosiglitazone.

The hypotensive agents are preferably understood as meaning compounds from the group of the calcium antagonists, angiotensin AII antagonists, ACE inhibitors, beta-receptor blockers, alpha-receptor blockers and diuretics.

In a preferred embodiment of the invention, the compounds according to the invention are administered in combination with a calcium antagonist, such as, by way of example and by way of preference, nifedipine, amlodipine, verapamil or diltiazem.

In a preferred embodiment of the invention, the compounds according to the invention are administered in combination with an angiotensin AII antagonist, such as, by way of example and by way of preference, losartan, valsartan, candesartan, embusartan, olmesartan or telmisartan.

In a preferred embodiment of the invention, the compounds according to the invention are administered in combination with an ACE inhibitor, such as, by way of example and by way of preference, enalapril, captopril, lisinopril, ramipril, delapril, fosinopril, quinopril, perindopril or trandopril.

In a preferred embodiment of the invention, the compounds according to the invention are administered in combination with a beta-receptor blocker, such as, by way of example and by way of preference, propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the compounds according to the invention are administered in combination with an alpha-receptor blocker, such as, by way of example and by way of preference, prazosin.

In a preferred embodiment of the invention, the compounds according to the invention are administered in combination with a diuretic, such as, by way of example and by way of preference, furosemide, bumetanide, torsemide, bendroflumethiazide, chlorothiazide, hydrochlorothiazide, hydroflumethiazide, methyclothiazide, polythiazide, trichloromethiazide, chlorothalidone, indapamide, metolazone, quinethazone, acetazolamide, dichlorophenamide, methazolamide, glycerol, isosorbide, mannitol, amiloride or triamteren.

In a preferred embodiment of the invention, the compounds according to the invention are administered in combination with an aldosterone or mineralocorticoid receptor antagonist, such as, by way of example and by way of preference, spironolactone or eplerenone.

In a preferred embodiment of the invention, the compounds according to the invention are administered in combination with a vasopressin receptor antagonist, such as, by way of example and by way of preference, conivaptan, tolvaptan, lixivaptan or SR-121463.

In a preferred embodiment of the invention, the compounds according to the invention are administered in combination with an organic nitrate or NO donor, such as, by way of example and by way of preference, sodium nitroprusside, nitroglycerol, isosorbide mononitrate, isosorbide dinitrate, molsidomin or SIN-1, or in combination with inhalative NO.

In a preferred embodiment of the invention, the compounds according to the invention are administered in combination with a positive-inotropic compound, such as, by way of example and by way of preference, cardiac glycosides (digoxin), beta-adrenergic and dopaminergic agonists, such as isoproterenol, adrenaline, noradrenaline, dopamine or dobutamine.

In a preferred embodiment of the invention, the compounds according to the invention are administered in combination with antisympathotonics, such as reserpine, clonidine or alpha-methyldopa, or in combination with potassium channel agonists, such as minoxidil, diazoxide, dihydralazine or hydralazine, or with substances which release nitrogen oxide, such as glycerol nitrate or sodium nitroprusside.

Antithrombotics are to be understood as meaning, preferably, compounds from the group of the platelet aggregation inhibitors or the anticoagulants.

In a preferred embodiment of the invention, the compounds according to the invention are administered in combination with a platelet aggregation inhibitor, such as, by way of example and by way of preference, aspirin, clopidogrel, ticlopidine or dipyridamol.

In a preferred embodiment of the invention, the compounds according to the invention are administered in combination with a thrombin inhibitor, such as, by way of example and by way of preference, ximelagatran, melagatran, dabigatran, bivalirudin or clexane.

In a preferred embodiment of the invention, the compounds according to the invention are administered in combination with a GPIIb/IIIa antagonist, such as, by way of example and by way of preference, tirofiban or abciximab.

In a preferred embodiment of the invention, the compounds according to the invention are administered in combination with a factor Xa inhibitor, such as, by way of example and by way of preference, rivaroxaban (BAY 59-7939), DU-176b, apixaban, otamixaban, fidexaban, razaxaban, fondaparinux, idraparinux, PMD-3112, YM-150, KFA-1982, EMD-503982, MCM-17, MLN-1021, DX 9065a, DPC 906, JTV 803, SSR-126512 or SSR-128428.

In a preferred embodiment of the invention, the compounds according to the invention are administered in combination with heparin or a low molecular weight (LMW) heparin derivative.

In a preferred embodiment of the invention, the compounds according to the invention are administered in combination with a vitamin K antagonist, such as, by way of example and by way of preference, coumarin.

In the context of the present invention, particular preference is given to combinations comprising at least one of the compounds according to the invention and also one or more further active ingredients selected from the group consisting of HMG-CoA reductase inhibitors (statins), diuretics, beta-receptor blockers, organic nitrates and NO donors, ACE inhibitors, angiotensin AII antagonists, aldosterone and mineralocorticoid receptor antagonists, vasopressin receptor antagonists, platelet aggregation inhibitors and anticoagulants, and also their use for the treatment and/or prevention of the disorders mentioned above.

The present invention furthermore provides medicaments comprising at least one compound according to the invention, usually together with one or more inert nontoxic pharmaceutically suitable auxiliaries, and also their use for the purposes mentioned above.

The compounds according to the invention can act systemically and/or locally. For this purpose, they can be administered in a suitable manner, such as, for example, orally, parenterally, pulmonally, nasally, sublingually, lingually, buccally, rectally, dermally, transdermally, conjunctivally, otically or as an implant or stent.

For these administration routes, the compounds according to the invention can be administered in suitable administration forms.

Suitable for oral administration are administration forms which work in accordance with the prior art and release the compounds according to the invention rapidly and/or in modified form and which comprise the compounds according to the invention in crystalline and/or amorphicized and/or dissolved form, such as, for example, tablets (uncoated or coated tablets, for example with enteric coats or coats which dissolve in a delayed manner or are insoluble and which control the release of the compound according to the invention), films/wafers or tablets which dissolve rapidly in the oral cavity, films/lyophilizates, capsules (for example hard or soft gelatin capsules), sugar-coated tablets, granules, pellets, powders, emulsions, suspensions, aerosols or solutions.

Parenteral administration may take place by circumventing a bioabsorption step (for example intravenously, intraarterially, intracardially, intraspinally or intralumbarly), or with bioabsorption (for example intramuscularly, subcutaneously, intracutaneously, percutaneously or intraperitoneally). Administration forms suitable for parenteral administration are inter alia preparations for injection or infusion in the form of solutions, suspensions, emulsions, lyophilizates or sterile powders.

Suitable for other administration routes are, for example, medicaments suitable for inhalation (inter alia powder inhalers, nebulizers), nose drops, solutions or sprays, tablets to be administered lingually, sublingually or buccally, films/wafers or capsules, suppositories, preparations to be administered to ears or eyes, vaginal capsules, aqueous suspensions (lotions, shaking mixtures), lipophilic suspensions, ointments, creams, transdermal therapeutic systems (for example plasters), milk, pastes, foams, powders for pouring, implants or stents.

Preference is given to oral or parenteral administration, in particular to oral and intravenous administration.

The compounds according to the invention can be converted into the administration forms mentioned. This can be carried out in a manner known per se by mixing with inert non-toxic pharmaceutically suitable auxiliaries. These auxiliaries include inter alia carriers (for example microcrystalline cellulose, lactose, mannitol), solvents (for example liquid polyethylene glycols), emulsifiers and dispersants or wetting agents (for example sodium dodecyl sulfate, polyoxysorbitan oleate), binders (for example polyvinylpyrrolidone), synthetic and natural polymers (for example albumin), stabilizers (for example antioxidants, such as, for example, ascorbic acid), colorants (for example inorganic pigments, such as, for example, iron oxides), and flavor and/or odor corrigents.

In general, it has been found to be advantageous in the case of parenteral administration to administer amounts of about 0.001 to 1 mg/kg, preferably about 0.01 to 0.5 mg/kg of body weight to obtain effective results. In the case of oral administration, the dosage is from about 0.01 to 100 mg/kg, preferably from about 0.01 to 20 mg/kg and very particularly preferably from 0.1 to 10 mg/kg of body weight.

In spite of this, it may be necessary to deviate from the amounts mentioned, namely depending on body weight, administration route, individual response to the active ingredient, the type of preparation and the time or the interval at which administration takes place. Thus, in some cases it may be sufficient to administer less than the abovementioned minimum amount, whereas in other cases the upper limit mentioned has to be exceeded. In the case of the administration of relatively large amounts, it may be expedient to divide these into a plurality of individual doses which are administered over the course of the day.

The working examples below illustrate the invention. The invention is not limited to the examples.

The percentages in the tests and examples below are, unless indicated otherwise, percentages by weight; parts are parts by weight. Solvent ratios, dilution ratios and concentrations of liquid/liquid solutions are in each case based on volume.

A. EXAMPLES

Abbreviations Used:

| | |
|---|---|
| aq. | aqueous |
| br s | broad singulet (in NMR) |
| Ex. | Example |
| c | concentration |
| d | doublett (in NMR) |
| dd | doublet of doublets (in NMR) |
| TLC | thin-layer chromatography |
| DCI | direct chemical ionization (in MS) |
| DMF | N,N-dimethylformamide |
| DMSO | dimethyl sulfoxide |
| ee | enantiomeric excess |
| EI | electron impact ionization (in MS) |
| ent | enantiomer/enantiomerically pure |
| ESI | electrospray ionization (in MS) |
| Et | ethyl |
| m.p. | melting point |
| GC-MS | gas chromatography-coupled mass spectrometry |
| h | hour(s) |
| HATU | O-(7-azabenzotriazol-1-yl)-N,N,N',N'-tetramethyluronium hexafluorophosphate |
| HPLC | high-pressure, high-performance liquid chromatography |
| cat. | catalytic |
| conc. | concentrated |
| LC-MS | liquid chromatography-coupled mass spectrometry |
| lit. | literature (reference) |
| MeCN | acetonitrile |
| min | minute(s) |
| MS | mass spectrometry |
| NMP | N-methylpyrrolidone |
| NMR | nuclear magnetic resonance spectrometry |
| q | quartet (in NMR) |
| rac. | racemic |
| RP-HPLC | reversed-phase HPLC |
| RT | room temperature |
| $R_t$ | retention time (in HPLC) |
| s | singlet (in NMR) |
| t | triplet (in NMR) |
| t-Bu | tert-butyl |
| TFA | trifluoroacetic acid |
| THF | tetrahydrofuran |
| dil. | dilute |

HPLC, LC-MS and GC-MS Methods:

Method 1 (HPLC): instrument: Hewlett Packard Series 1050; column: Symmetry TM C18 3.9×150 mm; flow rate: 1.5 ml/min; mobile phase A: water, mobile phase B: acetonitrile; gradient: →0.6 min 10% B→3.8 min 100% B→5.0 min 100% B→5.5 min 10% B; stop time: 6.0 min; injection volume: 10 µl; diode array detector signal: 214 and 254 nm.

Method 2 (LC-MS): MS instrument type: Micromass ZQ; HPLC instrument type: Waters Alliance 2795; column: Merck Chromolith SpeedROD RP-18e 100 mm×4.6 mm; mobile phase A: 1 l of water+0.5 ml of 50% strength formic acid, mobile phase B: 1 l of acetonitrile+0.5 ml of 50% strength formic acid; gradient: 0.0 min 10% B→7.0 min 95% B→9.0 min 95% B; oven: 35° C.; flow rate: 0.0 min 1.0 ml/min→7.0 min 2.0 ml/min→9.0 min 2.0 ml/min; UV detection: 210 nm.

Method 3 (LC-MS): MS instrument type: Micromass ZQ; HPLC instrument type: HP 1100 series; UV DAD; column: Phenomenex Gemini 3µ 30 mm×3.00 mm; mobile phase A: 1 l of water+0.5 ml of 50% strength formic acid, mobile phase B: 1 l of acetonitrile+0.5 ml of 50% strength formic acid; gradient: 0.0 min 90% A→2.5 min 30% A→3.0 min 5% A→4.5 min 5% A; flow rate: 0.0 min 1 ml/min, 2.5 min/3.0 min/4.5 min. 2 ml/min; oven: 50° C.; UV detection: 210 nm.

Method 4 (LC-MS): instrument: Micromass Quattro LCZ with HPLC Agilent series 1100; column: Phenomenex Onyx Monolithic C18, 100 mm×3 mm. mobile phase A: 1 l of water+0.5 ml of 50% strength formic acid, mobile phase B: 1 l of acetonitrile+0.5 ml of 50% strength formic acid; gradient: 0.0 min 90% A→2 min 65% A→4.5 min 5% A→6 min 5% A; flow rate: 2 ml/min; oven: 40° C.; UV detection: 208-400 nm.

Method 5 (LC-MS): MS instrument type: Micromass ZQ; HPLC instrument type: Waters Alliance 2795; column: Phenomenex Synergi 2.5µ MAX-RP 100A Mercury 20 mm×4 mm; mobile phase A: 1 l of water+0.5 ml of 50% strength formic acid, mobile phase B: 1 l of acetonitrile+0.5 ml of 50% strength formic acid; gradient: 0.0 min 90% A→0.1 min 90% A→3.0 min 5% A→4.0 min 5% A→4.01 min 90% A; flow rate: 2 ml/min; oven: 50° C.; UV detection: 210 nm.

Method 6 (LC-MS): instrument: Micromass QuattroPremier with Waters HPLC Acquity; column: Thermo Hypersil GOLD 1.9µ 50×1 mm; mobile phase A: 1 l of water+0.5 ml of 50% strength formic acid, mobile phase B: 1 l of acetonitrile+0.5 ml of 50% strength formic acid; gradient: 0.0 min 90% A→0.1 min 90% A→1.5 min 10% A→2.2 min 10% A; oven: 50° C.; flow rate: 0.33 ml/min; UV detection: 210 nm.

Method 7 (LC-MS): MS instrument type: Waters ZQ; HPLC instrument type: Waters Alliance 2795; column: Phenomenex Onyx Monolithic C18, 100 mm×3 mm; mobile phase A: 1 l of water+0.5 ml of 50% strength formic acid, mobile phase B: 1 l of acetonitrile+0.5 ml of 50% strength formic acid; gradient: 0.0 min 90% A→2 min 65% A→4.5 min 5% A→6 min 5% A; flow rate: 2 ml/min; oven: 40° C.; UV detection: 210 nm.

Method 8 (LC-MS): instrument: Micromass Quattro LCZ with HPLC Agilent series 1100; column: Phenomenex Synergi 2.5µ MAX-RP 100A Mercury 20 mm×4 mm; mobile phase A: 1 l of water+0.5 ml of 50% strength formic acid, mobile phase B: 1 l of acetonitrile+0.5 ml of 50% strength formic acid; gradient: 0.0 min 90% A→0.1 min 90% A→3.0 min 5% A→4.0 min 5% A→4.1 min 90% A; flow rate: 2 ml/min; oven: 50° C.; UV detection: 208-400 nm.

Method 9 (LC-MS): instrument: Micromass Quattro LCZ with HPLC Agilent series 1100; column: Phenomenex Synergi 2µ Hydro-RP Mercury 20 mm×4 mm; mobile phase A: 1 l of water+0.5 ml of 50% strength formic acid, mobile phase B: 1 l of acetonitrile+0.5 ml of 50% strength formic acid; gradient: 0.0 min 90% A→2.5 min 30% A→3.0 min 5% A→4.5 min 5% A; flow rate: 0.0 min 1 ml/min, 2.5 min/3.0 min/4.5 min 2 ml/min; oven: 50° C.; UV detection: 208-400 nm.

Method 10 (LC-MS): MS instrument type: Micromass ZQ; HPLC instrument type: Waters Alliance 2795; column: Merck Chromolith SpeedROD RP-18e 100×4.6 mm; mobile phase A: 1 l of water+0.5 ml of 50% strength formic acid; mobile phase B: 1 l of acetonitrile+0.5 ml 50% strength formic acid; gradient: 0.0 min 10% B→7.0 min 95% B→9.0 min 95% B; oven: 35° C.; flow rate: 0.0 min 1.0 ml/min→7.0 min 2.0 ml/min→9.0 min 2.0 ml/min; UV detection: 210 nm.

Method 11 (LC-MS): instrument: Micromass Platform LCZ with HPLC Agilent series 1100; column: Thermo Hypersil GOLD 3µ 20×4 mm; mobile phase A: 1 l of water+0.5 ml of 50% strength formic acid, mobile phase B: 1 l of acetonitrile+0.5 ml of 50% strength formic acid; gradient: 0.0 min 100% A→0.2 min 100% A→2.9 min 30% A→3.1 min 10% A→5.5 min 10% A; oven: 50° C.; flow rate: 0.8 ml/min; UV detection: 210 nm.

Method 12 (LC-MS): MS instrument type: M-40 DCI (NH$_3$); HPLC instrument type: HP 1100 with DAD detection; column: Kromasil 100 RP-18, 60 mm×2.1 mm, 3.5 μm; mobile phase A: 5 ml HClO$_4$ (70% strength)/liter of water, mobile phase B: acetonitrile; gradient: 0 min 2% B→0.5 min 2% B→4.5 min 90% B→6.5 min 90% B→6.7 min 2% B→7.5 min 2% B; flow rate: 0.75 ml/min; column temperature: 30° C.; UV detection: 210 nm.

Method 13 (LC-MS): instrument: Micromass Quattro Micro MS with HPLC Agilent series 1100; column: Thermo Hypersil GOLD 3μ 20×4 mm; mobile phase A: 1 l of water+0.5 ml of 50% strength formic acid, mobile phase B: 1 l of acetonitrile+0.5 ml of 50% strength formic acid; gradient: 0.0 min 100% A 3.0 min 10% A 4.0 min 10% A 4.01 min 100% A (flow rate 2.5 ml) 5.00 min 100% A; oven: 50° C.; flow rate: 2 ml/min; UV detection: 210 nm Starting Materials and Intermediates:

Example 1A

2-Amino-4-[4-(2-hydroxyethoxy)phenyl]-6-sulfanylpyridine-3,5-dicarbonitrile

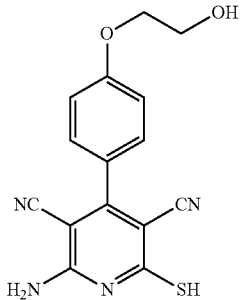 [SMILES: N#Cc1c(N)nc(S)c(C#N)c1-c1ccc(OCCO)cc1]

The preparation was carried out as described in WO 03/053441 for Example 6 (step 1).

LC-MS (Method 4): R$_t$=1.73 min; MS (ESIpos): m/z=313 [M+H]$^+$.

Example 2A

2-Amino-6-({[2-(4-chlorophenyl)-1,3-thiazol-4-yl]methyl}sulfanyl)-4-[4-(2-hydroxyethoxy)-phenyl]pyridine-3,5-dicarbonitrile

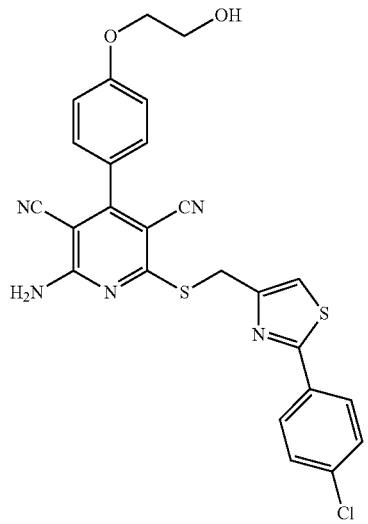

The preparation was carried out as described in WO 03/053441 for Example 6 (step 2).

LC-MS (Method 10): R$_t$=5.69 min; MS (ESIpos): m/z=520 [M+H]$^+$.

Example 3A

2-Amino-4-phenyl-6-sulfanylpyridine-3,5-dicarbonitrile

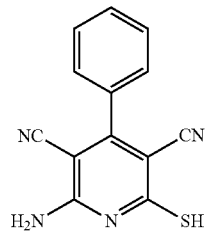

The preparation was carried out as described in WO 03/053441 for Example 6 (step 1).

MS (ESIpos): m/z=253 (M+H)$^+$

Example 4A

2-Amino-6-({[2-(4-chlorophenyl)-1,3-thiazol-4-yl]methyl}sulfanyl)-4-phenylpyridine-3,5-dicarbonitrile

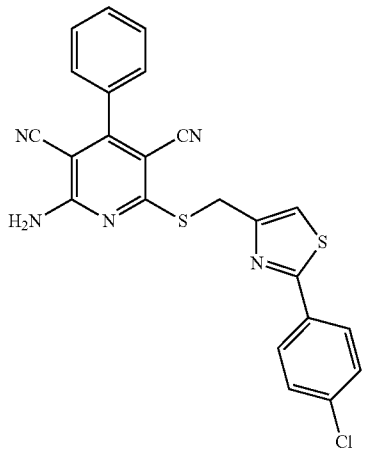 [SMILES: N#Cc1c(N)nc(SCc2csc(-c3ccc(Cl)cc3)n2)c(C#N)c1-c1ccccc1]

5.0 g (19.82 mmol) of the compound from Example 3A, 5.0 g (59.45 mmol) of sodium bicarbonate and 5.32 g (21.80 mmol) of 4-(chloromethyl)-2-(4-chlorophenyl)-1,3-thiazole were combined in 100 ml absolute DMF and stirred at room temperature overnight. The reaction mixture was poured into 700 ml of water. The precipitate formed was filtered off through a glass frit and washed with water. The residue was dried under reduced pressure.

Yield: 9.25 g (93% of theory, 92% pure)

LC-MS (Method 4): R$_t$=4.26 min; MS (ESIpos): m/z=460 [M+H]$^+$.

Example 5A 2-({[2-(4-Chlorophenyl)-1,3-thiazol-4-yl]methyl}thio)-4-(4-{[(2S)-2,3-dihydroxypropyl]oxy}phenyl)-5-oxo-1,4,5,6,7,8-hexahydroquinoline-3-carbonitrile

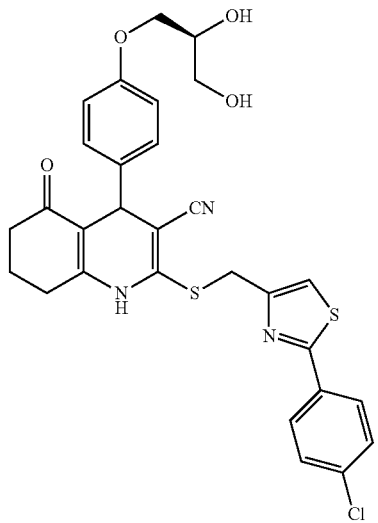 [SMILES: N#CC1=C(SCc2csc(-c3ccc(Cl)cc3)n2)NC2=C(C(=O)CCC2)C1c1ccc(OC[C@@H](O)CO)cc1]

150 mg (1.31 mmol) of 1,3-cyclohexanedione, 315 mg (1.31 mmol) of 4-{[(4R)-2,2-dimethyl-1,3-dioxolan-4-yl]methoxy}benzaldehyde [prepared analogously to Example 11A from WO 2006/027142] and 138 mg of 2-cyanoethanethioamide were initially charged in 4.3 ml of ethanol, 0.29 ml (2.62 mmol) of 4-methylmorpholine was added and the mixture was stirred at RT overnight.

After this time, 320 mg (1.31 mmol) of 4-(chloromethyl)-2-(4-chlorophenyl)-1,3-thiazole were added, and the reaction solution was stirred at RT overnight.

About 2 ml of water were added, and the reaction solution was purified by preparative HPLC (Chromasil, water/acetonitrile+0.1% TFA).

Yield: 214 mg (26% of theory)

$^1$H—NMR (400 MHz, DMSO-$d_6$): δ=9.91 (s, 1H), 7.91 (d, 2H), 7.54 (d, 2H), 7.49 (s, 1H), 6.98 (d, 2H), 6.78 (d, 2H), 4.48 (d, 1H), 4.41-4.35 (m, 2H), 3.93-3.87 (m, 1H), 3.80-3.70 (m, 2H), 3.41 (d, 2H), 2.67-2.49 (m, 2H), 2.24-2.16 (m, 2H), 1.98-1.74 (m, 2H).

LC-MS (Method 5): $R_t$=1.75 min; MS (ESIpos): m/z=580 [M+H]$^+$.

Example 6A

4-[4-(2-Hydroxyethoxy)phenyl]-2-mercapto-5-oxo-5,6-dihydro-1,6-naphthyridine-3-carbonitrile

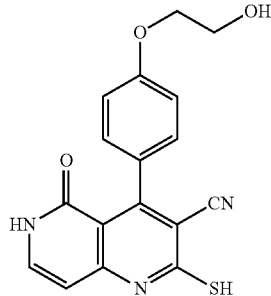 [SMILES: N#Cc1c(S)nc2cc[nH]c(=O)c2c1-c1ccc(OCCO)cc1]

1 g (9.08 mmol) of 4-aminopyridin-2(1H)-one [Searls, T., McLaughlin, L. W., Tetrahedron 55, 11985-11996 (1999)], 1.509 g (9.08 mmol) of 4-(2-hydroxyethoxy)benzaldehyde and 0.909 g (9.08 mmol) of 2-cyanoethanethioamide were initially charged in 50 ml of 2-propanol, 0.78 ml (13.62 mmol) of acetic acid was added and the mixture was stirred at reflux overnight.

The reaction mixture was concentrated and the crude product was subjected to chromatographic purification: Chromasil 100 C 18, 7 μm, 250×20 mm; mobile phase: water/acetonitrile/1% trifluoroacetic acid gradient; flow rate: 25 ml/min; 40° C.; detection: 210 nm.

Yield: 374 mg (12% of theory)

$^1$H—NMR (400 MHz, DMSO-$d_6$): δ=14.10 (s, 1H), 11.59 (d, 1H), 7.64-7.60 (m, 1H), 7.21 (d, 2H), 6.97 (d, 2H), 6.42 (d, 1H), 4.88 (br s, 1H), 4.06 (t, 2H), 3.75 (t, 2H).

LC-MS (Method 6): $R_t$=0.65 min; MS (ESIpos): m/z=340 [M+H]$^+$. (purity about 81%)

Example 7A

2-{4-[2-Amino-6-({[2-(4-chlorophenyl)-1,3-thiazol-4-yl]methyl}sulfanyl)-3,5-dicyanopyridin-4-yl]phenoxy}ethyl acetate

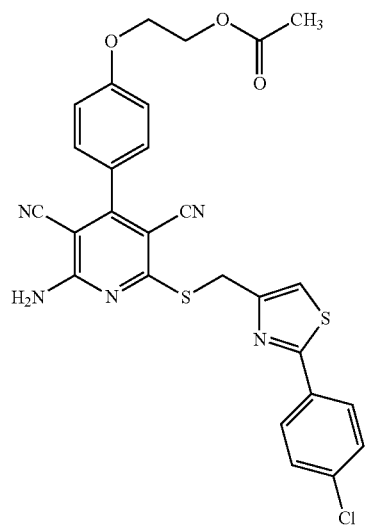 [SMILES: CC(=O)OCCOc1ccc(-c2c(C#N)c(N)nc(SCc3csc(-c4ccc(Cl)cc4)n3)c2C#N)cc1]

500 mg (0.96 mmol) of the compound from Example 2A were dissolved in 1.9 ml of acetic anhydride and heated under reflux for 1 h. About 1 ml of 1N hydrochloric acid were added, and the mixture was stirred for ten minutes. The resulting precipitate was filtered off and taken up in 8 ml of ethanol, stirred briefly and filtered off again. The precipitate was dried under reduced pressure.

Yield: 422 mg (77% of theory)

$^1$H—NMR (400 MHz, DMSO-$d_6$): δ=7.96 (s, 1H), 7.93 (d, 2H), 7.57 (d, 2H), 7.49 (d, 2H), 7.11 (d, 2H), 4.63 (s, 2H), 4.38-4.35 (m, 2H), 4.29-4.25 (m, 2H), 2.05 (s, 3H).

LC-MS (Method 7): $R_t$=4.08 min; MS (ESIpos): m/z=562 [M+H]$^+$.

Example 8A

2-{4-[7-({[2-(4-Chlorophenyl)-1,3-thiazol-4-yl]methyl}thio)-6-cyano-2-methyl-4-oxo-3,4-dihydropyrido[2,3-d]pyrimidin-5-yl]phenoxy}ethyl acetate

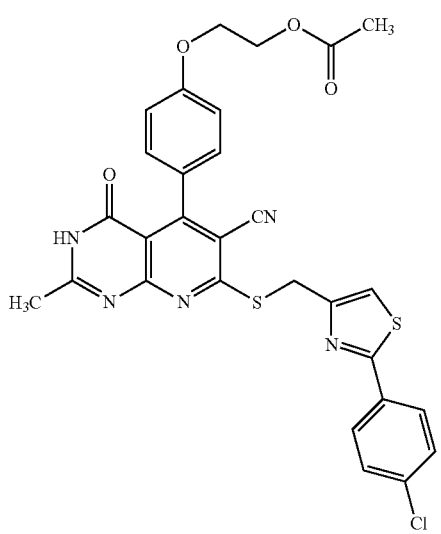 [SMILES: CC(=O)OCCOc1ccc(-c2c(C#N)c(SCc3csc(-c4ccc(Cl)cc4)n3)nc3nc(C)[nH]c(=O)c23)cc1]

200 mg (0.36 mmol) of the compound from Example 7A were dissolved in 0.7 ml of acetic anhydride and heated at reflux for 1 h. About 1 ml of 1N hydrochloric acid were added, and the mixture was stirred for another ten minutes. The precipitate formed was filtered off and taken up in 8 ml of ethanol, stirred briefly and filtered off again. The precipitate was dried under reduced pressure and then purified by preparative HPLC (column: YMC GEL ODS-AQ S-5/15 μm; mobile phase gradient: acetonitrile/water 10:90→95:5).

Yield: 24 mg (11% of theory)

$^1$H—NMR (400 MHz, DMSO-d$_6$): δ=8.28-8.00 (br s, 1H), 7.95 (d, 2H), 7.92 (s, 1H), 7.57 (d, 2H), 7.48 (d, 2H), 7.11 (d, 2H), 4.64 (s, 2H), 4.39-4.33 (m, 2H), 4.32-4.23 (m, 2H), 2.04 (s, 3H).

LC-MS (Method 7): R$_t$=2.39 min; MS (ESIpos): m/z=604 [M+H]$^+$.

Example 9A

7-Chloro-2,4-dioxo-5-phenyl-1,2,3,4-tetrahydropyrido[2,3-d]pyrimidine-6-carbonitrile

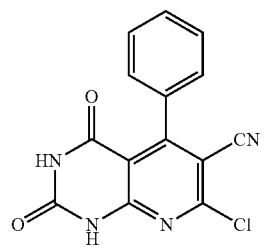 [SMILES: N#Cc1c(Cl)nc2[nH]c(=O)[nH]c(=O)c2c1-c1ccccc1]

1.0 g (3.04 mmol) of 7-amino-2,4-dioxo-5-phenyl-1,2,3,4-tetrahydropyrido[2,3-d]pyrimidine-6-carbonitrile [Assy, M. G. et al., J. Indian Chem. Soc. 1996, 73 (11), 623-624] was dissolved in 8 ml of DMSO, 0.82 ml (713 mg, 6.09 mmol) of isopentyl nitrite and 818 mg (6.09 mmol) of copper(II) chloride were added and the mixture was stirred at 80° C. overnight. The reaction mixture was cooled, and 6 ml of 1 N hydrochloric acid solution followed by 100 ml of water were then added. The precipitate formed was filtered off and dried under high vacuum. The product was not purified any further (purity according to LC-MS: about 82%).

Yield: 729 mg (64% of theory)

$^1$H—NMR (400 MHz, DMSO-d$_6$): δ=12.45 (br s, 1H), 11.59 (s, 1H), 7.50-7.43 (m, 3H), 7.36-7.29 (m, 2H).

LC-MS (Method 3): R$_t$=1.94 min; MS (ESIpos): m/z=299 [M+H]$^+$.

Example 10A

7-Amino-5-[4-(2-hydroxyethoxy)phenyl]-2,4-dioxo-1,2,3,4-tetrahydropyrido[2,3-d]pyrimidine-6-carbonitrile

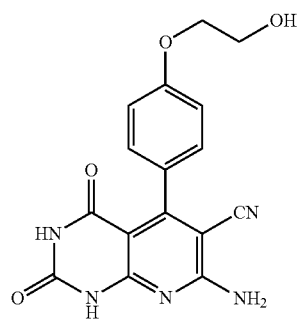 [SMILES: N#Cc1c(N)nc2[nH]c(=O)[nH]c(=O)c2c1-c1ccc(OCCO)cc1]

100 mg (0.602 mmol) of 4-(2-hydroxyethoxy)benzaldehyde, 76 mg (0.602 mmol) of 6-amino-1,2,3,4-tetrahydropyrimidine and 40 mg (0.602 mmol) of malononitrile were initially charged in 2 ml of ethanol, 0.13 ml (122 mg, 1.204 mmol) of 4-methylmorpholine was added and the mixture was stirred at reflux overnight. The reaction mixture was cooled, and about 20 ml of water were then added. The precipitate formed was filtered off and dried. The crude product was used without further purification for the subsequent reaction.

Yield: 128 mg (purity about 50%)

LC-MS (Method 5): R$_t$=0.74 min; MS (ESIpos): m/z=340 [M+H]$^+$.

Example 11A

7-Chloro-5-[4-(2-hydroxyethoxy)phenyl]-2,4-dioxo-1,2,3,4-tetrahydropyrido[2,3-d]pyrimidine-6-carbonitrile

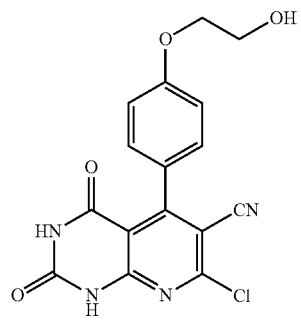 [SMILES: N#Cc1c(Cl)nc2[nH]c(=O)[nH]c(=O)c2c1-c1ccc(OCCO)cc1]

863 mg (about 1.272 mmol) of Example 10A were initially charged in 12 ml of DMSO/acetonitrile (1:1), 0.34 ml (298 mg, 2.54 mmol) of isopentyl nitrite and 342 mg (2.54 mmol) of copper(II) chloride were added and the mixture was stirred at 80° C. for 4 h. The reaction mixture was cooled, and 2.5 ml of 1 N hydrochloric acid solution followed by about 50 ml of water were then added. The precipitate formed was filtered off and the filtrate was evaporated. The crude product was purified by preparative HPLC (Chromasil, water/acetonitrile+0.1% TFA).

Yield: 143 mg (31% of theory)

LC-MS (Method 3): $R_t$=1.54 min; MS (ESIpos): m/z=359 [M+H]$^+$.

Example 12A 4-(Chloromethyl)-2-(4-chlorophenyl)-1,3-oxazole

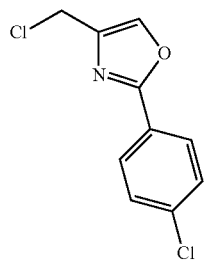 [SMILES: ClCc1coc(-c2ccc(Cl)cc2)n1]

408 mg (3.21 mmol) of 1,3-dichloroacetone and 500 mg (3.21 mmol) of 4-chlorobenzamide were combined and stirred at 135° C. for 1 h. The mixture was then cooled to RT, 1.1 ml of conc. sulfuric acid were added carefully and the mixture was stirred for another 5 min. Carefully, the mixture was poured onto ice. The precipitate was filtered off and washed with water. After drying, the crude product was used without further purification for the subsequent reaction.

Yield: 426 mg (49% of theory, 85% pure)

LC-MS (Method 11): $R_t$=3.78 min; MS (ESIpos): m/z=228 [M].

Example 13A 2-(4-Chlorophenyl)-4,5-dimethyl-1,3-oxazole 3-oxide

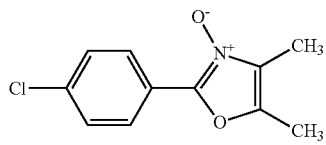

1.00 g (9.89 mmol) of diacetyl monoxime and 1.53 g (10.88 mmol) of 4-chlorobenzaldehyde were initially charged in 2 ml (34.94 mmol) of glacial acetic acid. Then, while the reaction mixture was cooled with ice, hydrogen chloride gas was introduced for 30 min. 10 ml of diethyl ether were then added to the reaction mixture. A precipitate was formed which was filtered off and washed twice with in each case 2 ml of diethyl ether. The precipitate was resuspended in about 5 ml of water and the suspension was made basic using 25% strength aqueous ammonia solution. The mixture was extracted four times with in each case 10 ml of dichloromethane. The combined organic phases were dried over magnesium sulfate and the solvent was removed on a rotary evaporator. Without further purification, the residue was used for the next reaction.

Yield: 1.85 g (84% of theory)

LC-MS (Method 5): $R_t$=2.29 min; MS (ESIpos): m/z=224 [M+H]$^+$.

Example 14A 4-(Chloromethyl)-2-(4-chlorophenyl)-5-methyl-1,3-oxazole

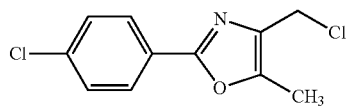

1.00 g (4.47 mmol) of the compound from Example 13A were initially charged in 15 ml of chloroform, and 1.5 ml (16.10 mmol) of phosphorus oxychloride were added carefully. With stirring, the reaction mixture was heated under reflux for 30 min. The reaction was then cooled to 0° C. and made slightly basic by addition of 25% strength aqueous ammonia solution. The mixture was extracted three times with in each case 20 ml of ethyl acetate. The combined organic phases were washed twice with in each case 5 ml of water and then dried over magnesium sulfate. The solvent was removed on a rotary evaporator. Without further purification, the residue was used for the subsequent steps.

Yield: 1.33 g (96% of theory, 78% pure)

$^1$H—NMR (400 MHz, DMSO-$d_6$): δ=7.95 (d, 2H), 7.60 (d, 2H), 4.77 (s, 2H), 2.44 (s, 3H).

LC-MS (Method 3): $R_t$=2.80 min; MS (ESIpos): m/z=242 [M+H]$^+$.

Example 15A

2-Amino-6-({[2-(4-chlorophenyl)-1,3-oxazol-4-yl]methyl}sulfanyl)-4-[4-(2-hydroxyethoxy)phenyl]pyridine-3,5-dicarbonitrile

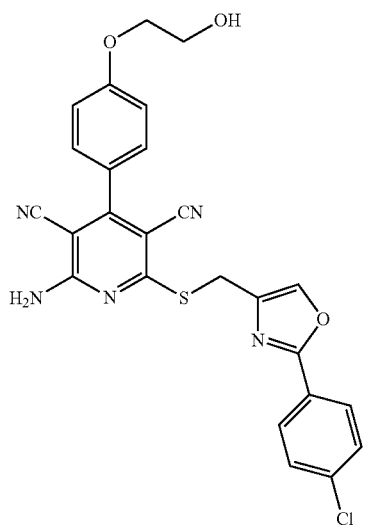 [SMILES: N#Cc1c(N)nc(SCc2coc(-c3ccc(Cl)cc3)n2)c(C#N)c1-c1ccc(OCCO)cc1]

500 mg (1.60 mmol) of Example 1A, 365 mg (1.60 mmol) of Example 12A and 403 mg (4.80 mmol) of sodium bicarbonate were dissolved in 11 ml of dry DMF. The reaction mixture was stirred at RT for 2 h. The reaction was diluted with about 5 ml of water and stirred for another 1 h. The precipitate formed was filtered off and dried in a drying cabinet at 40° C. Further purification is possible by preparative HPLC (column: YMC GEL ODS-AQ S-5/15 µm; mobile phase gradient: acetonitrile/water 10:90→95:5).

Yield: 665 mg (77% of theory)

$^1$H—NMR (400 MHz, DMSO-$d_6$): δ=8.37 (s, 1H), 8.31-7.89 (br. s, 2H), 7.97 (d, 2H), 7.60 (d, 2H), 7.46 (d, 2H), 7.10 (d, 2H), 4.91 (t, 1H), 4.41 (s, 2H), 4.08 (t, 2H), 3.74 (q, 2H).

LC-MS (Method 3): $R_t$=2.53 min; MS (ESIpos): m/z=504 [M+H]$^+$.

Example 16A

2-Amino-4-phenyl-6,7-dihydro-5H-cyclopenta[b]pyridine-3-carbonitrile

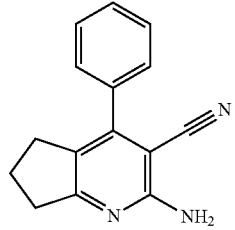 [SMILES: N#Cc1c(N)nc2c(c1-c1ccccc1)CCC2]

In 12 ml of toluene, 500 mg (5.94 mmol) of cyclopentanone, 916 mg (5.94 mmol) of benzylidenemalononitrile and 1.00 g (13.1 mmol) of ammonium acetate were heated under reflux for 2 h. The mixture was washed with 10 ml of a saturated aqueous sodium bicarbonate solution and then with 10 ml of water, dried over magnesium sulfate and freed from the solvent on a rotary evaporator. The residue was purified by preparative HPLC (column: YMC GEL ODS-AQ S-5, 15 µm; mobile phase gradient: acetonitrile/water 10:90→95:5).

Yield: 250 mg (18% of theory)

$^1$H—NMR (400 MHz, DMSO-$d_6$): δ=7.53-7.43 (m, 5H), 6.68 (s, 2H), 2.83 (t, 2H), 2.62 (t, 2H), 1.95 (m, 2H).

LC-MS (Method 6): $R_t$=1.08 min; MS (ESIpos): m/z=235 [M+H]$^+$.

Example 17A

2-Chloro-4-phenyl-6,7-dihydro-5H-cyclopenta[b]pyridine-3-carbonitrile

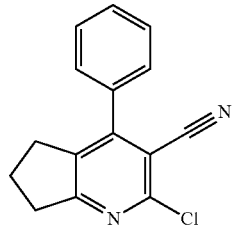 [SMILES: N#Cc1c(Cl)nc2c(c1-c1ccccc1)CCC2]

Under argon, 500 mg (2.12 mmol) of the compound from Example 16A, 0.57 ml (4.25 mmol) of isopentyl nitrite and 571 mg (4.25 mmol) of copper(II) chloride in 21 ml of tetrahydrofuran were heated under reflux for 6 h. After cooling, 1 N hydrochloric acid was added and the reaction mixture was extracted with ethyl acetate. The organic phase was washed with water and a saturated aqueous sodium chloride solution, dried over magnesium sulfate and freed from the solvent on a rotary evaporator. The residue was purified by preparative HPLC (column: YMC GEL ODS-AQ S-5, 15 µm; mobile phase gradient: acetonitrile/water 10:90→95:5).

Yield: 158 mg (29% of theory)

LC-MS (Method 3): $R_t$=2.63 min; MS (ESIpos): m/z=254 [M+H]$^+$.

Example 18A

Sodium [3-cyano-4-phenyl-6,7-dihydro-5H-cyclopenta[b]pyridine-2-thiolate]

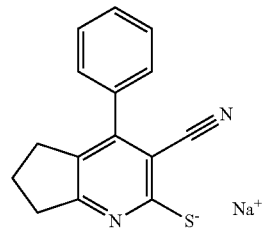 [SMILES: N#Cc1c([S-])nc2c(c1-c1ccccc1)CCC2 ; [Na+]]

147 mg (1.89 mmol) of sodium sulfide are added to a solution of 400 mg (1.57 mmol) of the compound from Example 17A in 4.8 ml DMF, and the mixture was stirred at 30° C. for 5 h. Without further work-up, the reaction mixture was directly reacted further.

LC-MS (Method 4): $R_t$=4.68 min; MS (ESIpos): m/z=483 [M+H]$^+$.

Example 19A

5-Oxo-4-(1H-pyrazol-3-yl)-2-sulfanyl-5,6-dihydro-1,6-naphthyridine-3-carbonitrile

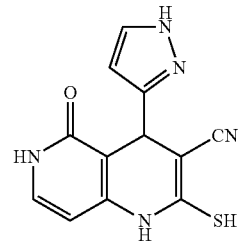 [SMILES: N#CC1=C(S)Nc2cc[nH]c(=O)c2C1c1cc[nH]n1]

573 mg (5.20 mmol) of 4-aminopyridin-2(1H)-one, 500 mg (5.02 mmol) of pyrazole-3-carbaldehyde and 521 mg (5.20 mmol) of 2-cyanoethanethioamide were initially charged in 25 ml of 2-propanol, 0.45 ml (7.81 mmol) of acetic acid was added and the mixture was stirred at reflux for 48 h. The precipitate was removed by filtration, and the filtrate was evaporated and reacted further without further purification.

Yield: 608 mg (4% of theory, purity about 9%)

LC-MS (Method 13): $R_t$=1.09 min; MS (ESIpos): m/z=272 [M+H]$^+$.

Example 20A 2-({[2-(4-Chlorophenyl)-1,3-thiazol-4-yl]methyl}sulfanyl)-5-oxo-4-(1H-pyrazol-3-yl)-1,4,5,6-tetrahydro-1,6-naphthyridine-3-carbonitrile

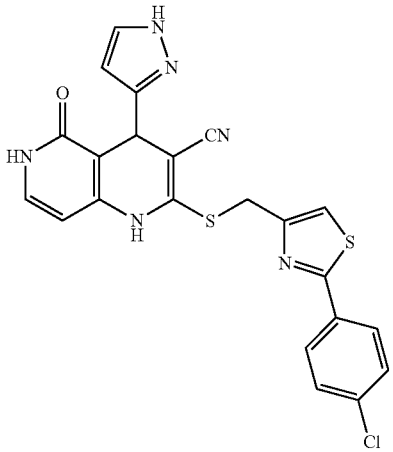 [SMILES: N#CC1=C(SCc2csc(-c3ccc(Cl)cc3)n2)Nc2cc[nH]c(=O)c2C1c1cc[nH]n1]

608 mg (about 0.20 mmol) of Example 19A were dissolved in 2 ml of DMF, 55 mg (0.22 mmol) of 4-chloromethyl-2-(4-chlorophenyl)thiazole and 68 mg (0.81 mmol) of sodium bicarbonate were added and the mixture was stirred at RT for 4 h. A little water was added to the reaction mixture, such that a clear solution was formed. This solution was purified by preparative HPLC (Chromasil, water/acetonitrile+0.1% TFA).

Yield: 31 mg (32% of theory)

$^1$H—NMR (400 MHz, DMSO-$d_6$): δ=11.25 (br s, 1H), 9.99 (s, 1H), 7.80 (d, 2H), 7.53-7.42 (m, 4H), 7.22 (d, 1H), 6.03 (d, 1H), 5.92 (d, 1H), 4.70 (s, 1H), 4.56 (d, 1H), 4.29 (d, 1H).

LC-MS (Method 5): $R_t$=1.54 min; MS (ESIpos): m/z=479 [M+H]$^+$.

Example 21A

4-[4-(2-Hydroxyethoxy)phenyl]-2-(methylsulfanyl)-5-oxo-5,6-dihydro-1,6-naphthyridine-3-carbonitrile

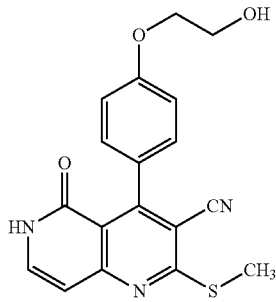 [SMILES: CSc1nc2cc[nH]c(=O)c2c(-c2ccc(OCCO)cc2)c1C#N]

283 mg (0.83 mmol) of Example 6A were initially charged in 5.7 ml of DMF and cooled to 0° C. 118 mg (0.83 mmol) of iodomethane and 140 mg (1.67 mmol) of sodium bicarbonate were added, and the mixture was stirred at 0° C. for 1 h. Water was added to the reaction mixture, and the precipitate was filtered off. The precipitate was dried overnight in a drying cabinet at 50° C. and reacted without further purification.

Yield: 198 mg (67% of theory)

$^1$H—NHR (400 MHz, DMSO-$d_6$): δ=11.49 (br s, 1H), 7.60 (d, 1H), 7.22 (d, 2H), 6.98 (d, 2H), 6.58 (d, 1H), 4.90 (br s, 1H), 4.05 (t, 2H), 3.80-3.70 (m, 2H), 2.69 (s, 3H).

LC-MS (Method 5): $R_t$=1.43 min; MS (ESIpos): m/z=354 [M+H]$^+$.

Example 22A

2-Amino-6-({[2-(4-chlorophenyl)-1,3-thiazol-4-yl]methyl}sulfanyl)-5-cyano-4-[4-(2-hydroxyethoxy)phenyl]pyridine-3-carboxamide

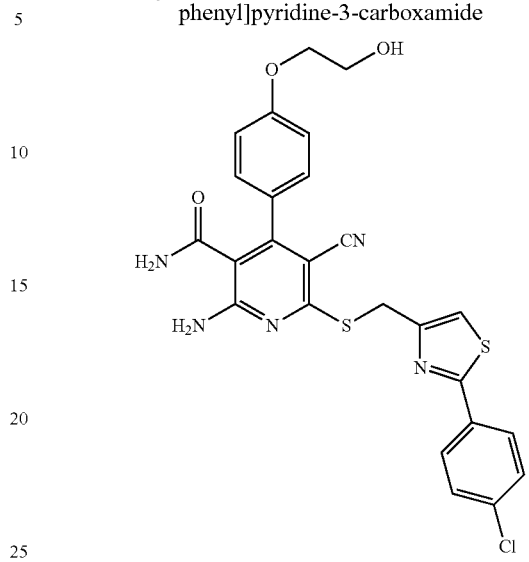

500 mg (0.961 mmol) of the compound from Example 2A were suspended in 24 ml of 50% strength sulfuric acid and stirred at 100° C. overnight. After cooling, the reaction solution formed was poured onto ice. The precipitate formed was filtered off with suction and dissolved in DMF/THF and then purified by preparative HPLC (Chromasil, water/acetonitrile+0.1% TFA).

Yield: 81 mg (16% of theory)

$^1$H—NHR (400 MHz, DMSO-$d_6$): δ=7.93 (d, 2H), 7.89 (s, 1H), 7.58 (d, 2H), 7.32 (d, 2H), 7.29 (d, 2H), 7.18 (br s, 2H), 6.98 (d, 2H), 4.61 (s, 2H), 4.03 (t, 2H), 3.71 (t, 2H).

LC-MS (Method 5): $R_t$=1.93 min; MS (ESIpos): m/z=538 [M+H]$^+$.

Example 23A

2-{4-[7-({[2-(4-Chlorophenyl)-1,3-oxazol-4-yl]methyl}sulfanyl)-6-cyano-2-methyl-4-oxo-3,4-dihydropyrido[2,3-d]pyrimidin-5-yl]phenoxy}ethyl acetate

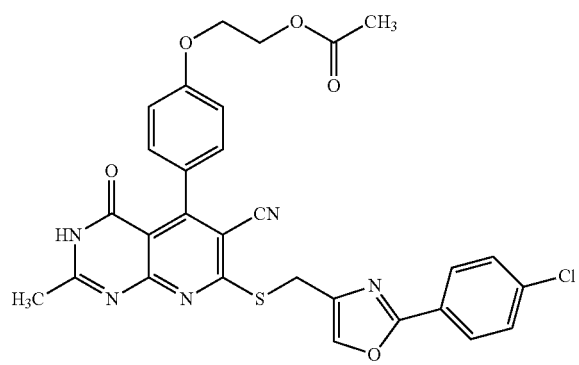 [SMILES: CC(=O)OCCOc1ccc(-c2c(C#N)c(SCc3coc(-c4ccc(Cl)cc4)n3)nc3nc(C)[nH]c(=O)c23)cc1]

For 1 h, 770 mg (1.528 mmol) of 2-amino-6-({[2-(4-chlorophenyl)-1,3-oxazol-4-yl]methyl}sulfanyl)-4-[4-(2-hydroxyethoxy)phenyl]pyridine-3,5-dicarbonitrile were heated under reflux in 2.883 ml (30.557 mmol) of acetic anhydride. 1 N hydrochloric acid was then added to the cooled reaction mixture, and the precipitated solid was filtered off, washed with water and diethyl ether and dried under reduced pressure. The crude product was purified by preparative HPLC (mobile phase gradient: acetonitrile/water 10:90→95:5, with 0.1% TFA added). This gave 102 mg (11% of theory) of the target compound.

$^1$H—NHR (400 MHz, DMSO-$d_6$): δ=11.15 (s, 1H), 8.30 (s, 1H), 7.97 (d, 2H), 7.61 (d, 2H), 7.55 (d, 2H), 7.18 (d, 2H), 4.57 (s, 2H), 4.38-4.35 (m, 2H), 4.31-4.29 (m, 2H), 2.24 (s, 3H), 2.05 (s, 3H).

LC-MS (Method 5): $R_t$=2.29 min; MS (ESIpos): m/z=588 [M+H]$^+$.

Example 24A

2-{4-[7-({[2-(4-Chlorophenyl)-1,3-thiazol-4-yl]methyl}sulfanyl)-6-cyano-2-ethyl-4-oxo-3,4-dihydropyrido[2,3-d]pyrimidin-5-yl]phenoxy}ethyl propanoate

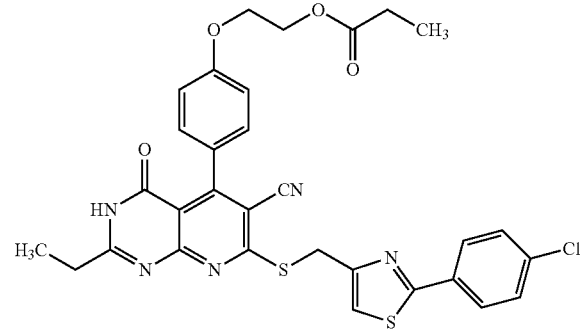 [SMILES: CCC(=O)OCCOc1ccc(-c2c(C#N)c(SCc3csc(-c4ccc(Cl)cc4)n3)nc3nc(CC)[nH]c(=O)c23)cc1]

For 1 h, 100 mg (0.192 mmol) of 2-amino-6-({[2-(4-chlorophenyl)-1,3-thiazol-4-yl]methyl}sulfanyl)-4-[4-(2-hydroxyethoxy)phenyl]pyridine-3,5-dicarbonitrile were heated under reflux in 0.493 ml (3.846 mmol) of propanoic anhydride. The cooled reaction mixture was then purified directly by preparative HPLC (mobile phase gradient: acetonitrile/water 10:90→95:5, with 0.1% TFA added). This gave 44 mg (36% of theory) of the target compound.

$^1$H—NHR (400 MHz, DMSO-$d_6$): δ=11.13 (s, 1H), 7.95 (d, 2H), 7.84 (s, 1H), 7.59-7.53 (m, 4H), 7.18 (d, 2H), 4.77 (s, 2H), 4.40-4.37 (m, 2H), 4.31-4.29 (m, 2H), 2.56-2.53 (m, 2H), 2.35 (q, 2H), 1.14 (t, 3H), 1.03 (t, 3H).

LC-MS (Method 5): $R_t$=2.61 min; MS (ESIpos): m/z=632 [M+H]$^+$.

WORKING EXAMPLES

Example 1

7-({[2-(4-Chlorophenyl)-1,3-thiazol-4-yl]methyl}thio)-4-oxo-5-phenyl-3,4-dihydropyrido[2,3-d]pyrimidine-6-carbonitrile

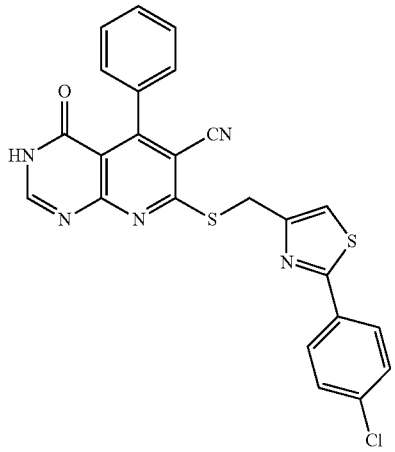 [SMILES: N#Cc1c(SCc2csc(-c3ccc(Cl)cc3)n2)nc2nc[nH]c(=O)c2c1-c1ccccc1]

Seven Batches of the Following Size were Prepared:

50 mg (0.11 mmol) of Example 4A were dissolved in 200 μl of THF, 0.6 ml (16.3 mmol) of formic acid were added and the mixture was irradiated in a microwave at 180° C. for 30 min.

The seven reaction solutions were combined and carefully poured into a mixture of semiconcentrated sodium bicarbonate solution and ethyl acetate (vigorous evolution of gas). The two phases were separated, and the aqueous phase was extracted once with ethyl acetate. The combined organic phases were washed with saturated aqueous sodium chloride solution, dried over sodium sulfate, filtered and concentrated. The crude product was purified by preparative HPLC [Chromasil, water/acetonitrile+0.3% formic acid]. This gave 32 mg, which were separated once more by preparative HPLC [Waters Symmetry C 18, 7 μm, 300×19 mm; mobile phase: acetonitrile+0.2% trifluoroacetic acid; flow rate: 25 ml/min; RT; detection: 210 nm].

Yield: 4 mg (1% of theory)

$^1$H—NHR (400 MHz, DMSO-$d_6$): δ=12.61 (br s, 1H), 8.39 (s, 1H), 7.97 (d, 2H), 7.79 (s, 1H), 7.58 (d, 2H), 7.48-7.40 (m, 3H), 7.38-7.31 (m, 2H), 4.80 (s, 2H).

LC-MS (Method 10): $R_t$=5.39 min; MS (ESIpos): m/z=488 [M+H]$^+$.

Example 2

2-({[2-(4-Chlorophenyl)-1,3-thiazol-4-yl]methyl}thio)-4-[4-(2-hydroxyethoxy)phenyl]-5-oxo-5,6,7,8-tetrahydroquinoline-3-carbonitrile

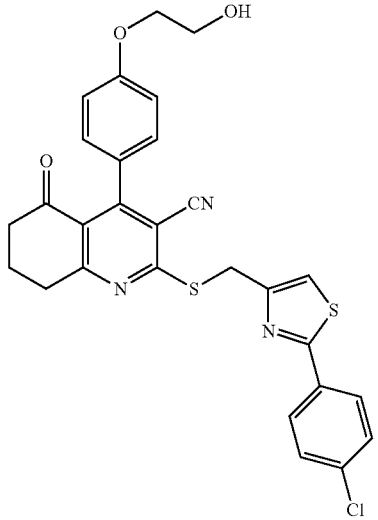 [SMILES: N#Cc1c(SCc2csc(-c3ccc(Cl)cc3)n2)nc2c(c1-c1ccc(OCCO)cc1)C(=O)CCC2]

100 mg (0.874 mmol) of 1,3-cyclohexanedione, 150 mg (0.874 mmol) of 4-(hydroxyethoxy)benzaldehyde and 92 mg (0.874 mmol) of 2-cyanoethanethioamide were initially charged in 2.9 ml of ethanol and stirred with 179 mg (1.748 mmol) of N-methylmorpholine at RT overnight. 213 mg (0.874 mmol) of 4-(chloromethyl)-2-(4-chlorophenyl)-1,3-thiazole were then added, and the mixture was stirred at RT for a further 2.5 hours. The reaction mixture was diluted with water and dichloromethane, the two phase were separated and the aqueous phase was extracted four times with dichloromethane. The combined organic phases were washed in each case once with 0.5 N hydrochloric acid and saturated aqueous sodium chloride solution, dried over sodium sulfate, filtered and concentrated. The crude product was purified by preparative HPLC [Chromasil, water/acetonitrile+0.15% hydrochloric acid].

Yield: 27 mg (6% of theory)

$^1$H—NHR (400 MHz, DMSO-$d_6$): δ=7.97 (d, 2H), 7.76 (s, 1H), 7.58 (d, 2H), 7.20 (d, 2H), 6.98 (d, 2H), 4.90 (br s, 1H), 4.78 (s, 2H), 4.05 (t, 2H), 3.74 (t, 2H), 3.24 (t, 2H), 2.58 (t, 2H), 2.11 (Quintett, 2H).

LC-MS (Method 4): $R_t$=4.26 min; MS (ESIpos): m/z=548 [M+H]$^+$.

Example 3

2-({[2-(4-Chlorophenyl)-1,3-thiazol-4-yl]methyl}thio)-4-(4-{[(2S)-2,3-dihydroxypropyl]oxy}-phenyl)-5-oxo-5,6,7,8-tetrahydroquinoline-3-carbonitrile

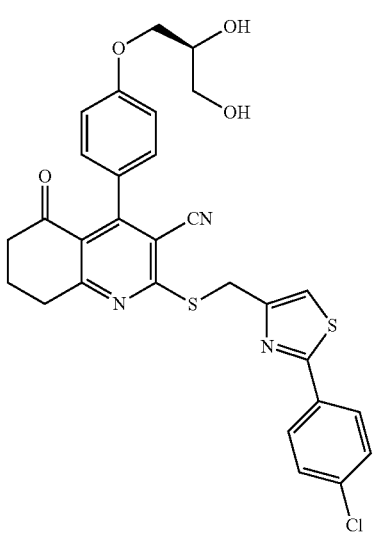 [SMILES: N#Cc1c(SCc2csc(-c3ccc(Cl)cc3)n2)nc2c(c1-c1ccc(OC[C@@H](O)CO)cc1)C(=O)CCC2]

At RT, 100 mg (0.172 mmol) of the compound from Example 5A and 40 mg (0.174 mmol) of 2,3-dichloro-5,6-dicyano-1,4-benzoquinone were stirred overnight in 6 ml of dichloromethane. The reaction solution was diluted with dichloromethane and water, and the two phases were separated. The aqueous phase was extracted twice with dichloromethane. The combined organic phases were concentrated and purified by preparative HPLC (Chromasil, water/acetonitrile+0.1% TFA).

Yield: 78 mg (78% of theory)

$^1$H—NHR (400 MHz, DMSO-d$_6$): δ=7.97 (d, 2H), 7.78 (s, 1H), 7.58 (d, 2H), 7.19 (d, 2H), 6.98 (d, 2H), 4.99 (br s, 1H), 4.78 (s, 2H), 4.70 (br s, 1H), 4.08 (dd, 1H), 3.92 (dd, 1H), 3.85-3.78 (m, 1H), 3.24 (t, 2H), 2.58 (t, 2H), 2.10 (quintet, 2H).

LC-MS (Method 8): R$_t$=2.45 min; MS (ESIpos): m/z=578 [M+H]$^+$.

Example 4

2-({[2-(4-Chlorophenyl)-1,3-thiazol-4-yl]methyl}thio)-4-(4-{[(2S)-2,3-dihydroxypropyl]oxy}-phenyl)-5-hydroxy-5,6,7,8-tetrahydroquinoline-3-carbonitrile

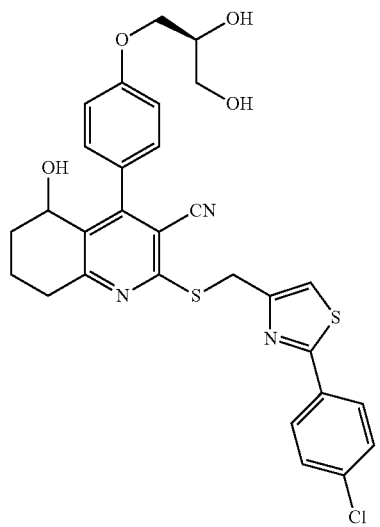 [SMILES: N#Cc1c(SCc2csc(-c3ccc(Cl)cc3)n2)nc2c(c1-c1ccc(OC[C@@H](O)CO)cc1)C(O)CCC2]

25 mg (0.043 mmol) of the compound from Example 3 were initially charged in 1 ml of THF and 0.1 ml of methanol, 0.8 mg (0.022 mmol) of sodium borohydride was added with stirring and the mixture was stirred at RT for 16 h. The reaction solution was diluted with about 2 ml of water and purified by preparative HPLC (Chromasil, water/acetonitrile+0.1% TFA).

Yield: 15.8 mg (63% of theory)

$^1$H—NHR (500 MHz, DMSO-d$_6$): δ=7.97-7.90 (m, 2H), 7.68 (s, 1H), 7.59-7.42 (m, 3H), 7.26 (br s, 1H), 7.03 (d, 2H), 4.88 (br s, 1H), 4.70 (dd, 2H), 4.39 (s, 1H), 4.09-4.02 (m, 1H), 3.93-3.89 (m, 1H), 3.83-3.78 (m, 1H), 3.45 (d, 2H), 3.12 (dd, 1H), 2.93-2.84 (m, 1H), 2.18-2.08 (m, 1H), 1.86-1.72 (m, 2H), 1.62-1.54 (m, 1H).

LC-MS (Method 5): R$_t$=2.23 min; MS (ESIpos): m/z=580 [M+H]$^+$.

Example 5

2-({[2-(4-Chlorophenyl)-1,3-oxazol-4-yl]methyl}thio)-4-[4-(2-hydroxyethoxy)phenyl]-5-oxo-5,6-dihydro-1,6-naphthyridine-3-carbonitrile

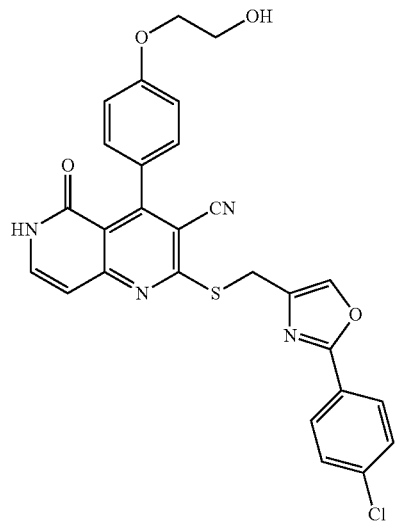 [SMILES: N#Cc1c(SCc2coc(-c3ccc(Cl)cc3)n2)nc2cc[nH]c(=O)c2c1-c1ccc(OCCO)cc1]

75 mg (about 0.179 mmol) of the compound from Example 6A and 66 mg (0.197 mmol) of 12A were initially charged in 3.5 ml of DMF, 45 mg (0.537 mmol) of sodium bicarbonate were added and the mixture was stirred at RT for 16 h. The reaction solution was diluted with about 2 ml of water and purified by preparative HPLC (Chromasil, water/acetonitrile+0.1% TFA).

Yield: 37 mg (39% of theory)

$^1$H—NHR (400 MHz, DMSO-d$_6$): δ=11.49 (d, 1H), 8.28 (s, 1H), 7.98 (d, 2H), 7.63-7.58 (m, 3H), 7.22 (d, 2H), 6.98 (d, 2H), 6.77 (d, 1H), 4.90 (t, 1H), 4.59 (s, 2H), 4.04 (t, 2H), 3.74 (q, 2H).

LC-MS (Method 6): R$_t$=1.27 min; MS (ESIpos): m/z=531 [M+H]$^+$.

The examples listed in Table 1 were prepared from the appropriate starting materials analogously to Example 5 with subsequent purification [preparative HPLC (Chromasil, water/acetonitrile+0.1% TFA)]:

TABLE 1

| Example No. | Structure (yield) | LC-MS: R$_t$ [min] (Method); MS (ESI): m/z [M + H]$^+$ | $^1$H-NMR (DMSO-d$_6$): |
|---|---|---|---|
| 6 | 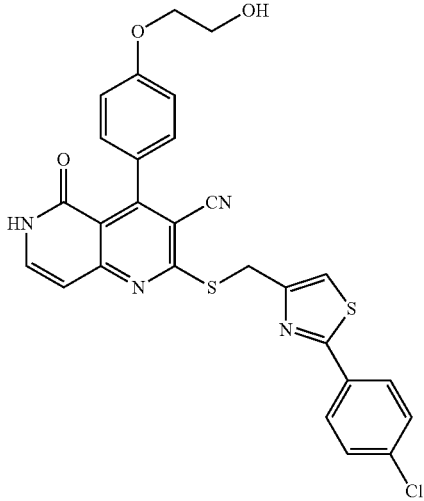 (12% of theory) | 2.15 min (Method 5); m/z = 547 | δ (400 MHz) = 11.50 (d, 1H), 7.95 (d, 2H), 7.81 (s, 1H), 7.63-7.55 (m, 3H), 7.22 (d, 2H), 6.98 (d, 2H), 6.72 (d, 1H), 4.79 (s, 2H), 4.05 (t, 2H), 3.75 (t, 2H). |
| 7 | 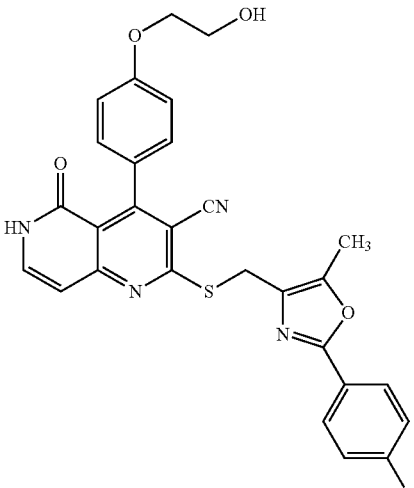 (4% of theory) | 2.71 min (Method 3); m/z = 545 | δ (400 MHz) = 11.49 (d, 1H), 7.92 (d, 2H), 7.63-7.55 (m, 3H), 7.22 (d, 2H), 6.98 (d, 2H), 6.67 (d, 1H), 4.90 (t, 1H), 4.59 (s, 2H), 4.05 (t, 2H), 3.74 (q, 2H), (s, 3H), 2.51 (s, 3H). |

Example 8

4-Amino-7-({[2-(4-chlorophenyl)-1,3-oxazol-4-yl]methyl}thio)-5-[4-(2-hydroxyethoxy)phenyl]-2-methylpyrido[2,3-d]pyrimidine-6-carbonitrile

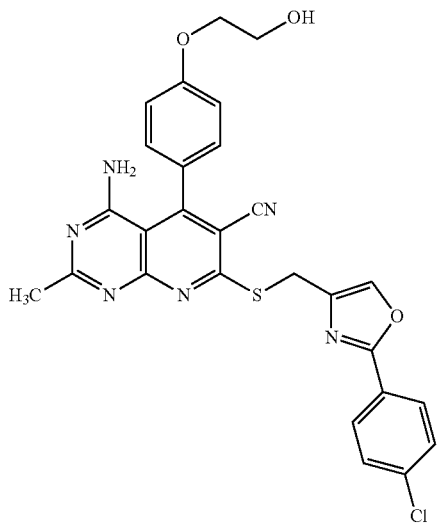 [SMILES: Cc1nc(N)c2c(-c3ccc(OCCO)cc3)c(C#N)c(SCc3coc(-c4ccc(Cl)cc4)n3)nc2n1]

50 mg (0.10 mmol) of the compound from Example 15A, 113 mg (0.69 mmol) of triethyl orthoformate and 38 mg (0.50 mmol) of ammonium acetate were combined and reacted in a microwave at 160° C. for 10 min. After cooling to RT, the reaction was purified directly by preparative HPLC (column: YMC GEL ODS-AQ S-5/15 μm; mobile phase gradient: acetonitrile/water 10:90→95:5).

Yield: 20 mg (36% of theory)

$^1$H—NHR (400 MHz, DMSO-$d_6$): δ=8.21 (s, 1H), 8.17 (br. s, 1H), 7.97 (d, 2H), 7.60 (d, 2H), 7.47 (d, 2H), 7.20 (d, 2H), 4.92 (t, 1H), 4.88 (br. s, 1H), 4.60 (s, 2H), 4.10 (t, 2H), 3.75 (q, 2H), (s, 3H hidden).

LC-MS (Method 3): $R_t$=1.98 min; MS (ESIpos): m/z=545 [M+H]$^+$.

Example 9

4-Amino-7-({[2-(4-chlorophenyl)-1,3-thiazol-4-yl]methyl}sulfanyl)-5-[4-(2-hydroxyethoxy)phenyl]-2-methylpyrido[2,3-d]pyrimidine-6-carbonitrile

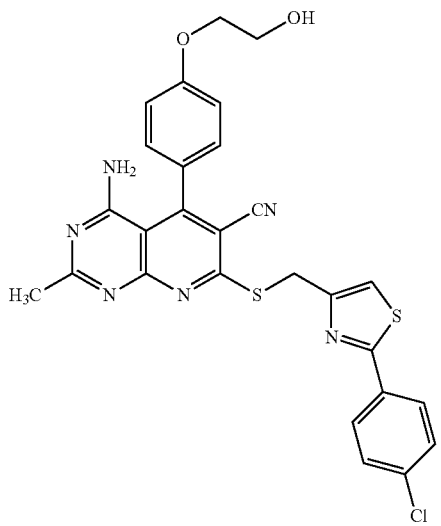 [SMILES: Cc1nc(N)c2c(-c3ccc(OCCO)cc3)c(C#N)c(SCc3csc(-c4ccc(Cl)cc4)n3)nc2n1]

The compound was prepared analogously to Example 5 from Example 2A.

Yield: 32 mg (14% of theory)

$^1$H—NHR (400 MHz, DMSO-$d_6$): δ=8.27-8.03 (br s, 2H), 7.97 (s, 1H), 7.93 (d, 2H), 7.58 (d, 2H), 7.48 (d, 2H), 7.12 (d, 2H), 4.63 (s, 2H), 4.39-4.34 (m, 2H), 4.31-4.26 (m, 2H), 2.03 (s, 3H).

LC-MS (Method 5): $R_t$=2.42 min; MS (ESIpos): m/z=562 [M+H]$^+$.

Example 10

7-({[2-(4-Chlorophenyl)-1,3-thiazol-4-yl]methyl}thio)-5-[4-(2-hydroxyethoxy)phenyl]-2-methyl-4-oxo-3,4-dihydropyrido[2,3-d]pyrimidine-6-carbonitrile

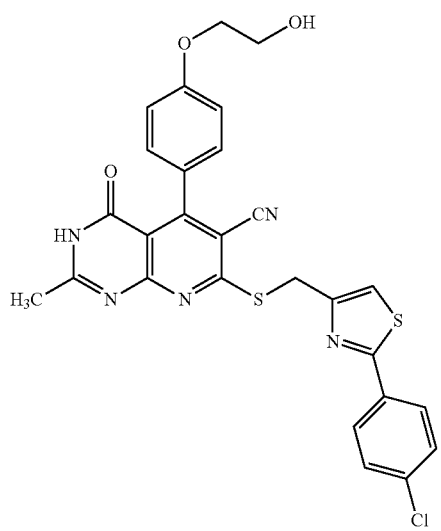 [SMILES: Cc1nc2nc(SCc3csc(-c4ccc(Cl)cc4)n3)c(C#N)c(-c3ccc(OCCO)cc3)c2c(=O)[nH]1]

24 mg (0.04 mmol) of the compound from Example 8A were initially charged in 2.3 ml of a 2:1 mixture of dioxane and water, and 1.9 mg (0.08 mmol) of lithium hydroxide were added. The reaction mixture was stirred at RT for 4 h. A further 1.9 mg (0.08 mmol) of lithium hydroxide were added, and the mixture was stirred for another 4 h. 2 ml of water were added to the reaction. The mixture was extracted three times in total with in each case 4 ml of ethyl acetate. The combined organic phases were dried over magnesium sulfate and the solvent was removed on a rotary evaporator. The residue was purified by preparative HPLC (column: YMC GEL ODS-AQ S-5/15 μm; mobile phase gradient: acetonitrile/water 10:90→95:5).

Yield: 15 mg (68% of theory)

$^1$H—NHR (500 MHz, DMSO-$d_6$): δ=11.14 (s, 1H), 7.94 (d, 2H), 7.83 (s, 1H), 7.57 (d, 2H), 7.53 (d, 2H), 7.16 (d, 2H), 4.89 (t, 1H), 4.77 (s, 2H), 4.12-4.08 (m, 2H), 3.78-3.73 (m, 2H), 2.23 (s, 3H).

LC-MS (Method 3): $R_t$=2.74 min; MS (ESIpos): m/z=562 [M+H]$^+$.

Example 11

7-({[2-(4-Chlorophenyl)-1,3-thiazol-4-yl]methyl}thio)-2,4-dioxo-5-phenyl-1,2,3,4-tetrahydropyrido[2,3-d]pyrimidine-6-carbonitrile

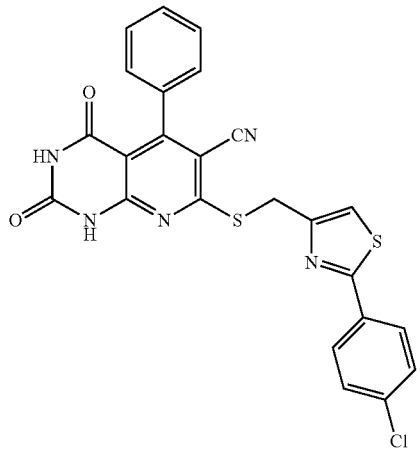 [SMILES: N#Cc1c(SCc2csc(-c3ccc(Cl)cc3)n2)nc2[nH]c(=O)[nH]c(=O)c2c1-c1ccccc1]

100 mg (0.275 mmol) of the compound from Example 9A were dissolved in 0.55 ml of DMF, 25 mg (0.329 mmol) of sodium sulfide were added and the mixture was stirred at RT overnight. The reaction solution was then diluted with 1 ml of DMF, 74 mg (0.302 mmol) of 4-(chloromethyl)-2-(4-chlorophenyl)-1,3-thiazole and 69 mg (0.825 mmol) of sodium bicarbonate were added and the mixture was stirred at RT for 45 min. Water was added to the reaction mixture. The precipitate formed was triturated with THF/Methanol (5 ml/2 ml) and then filtered off. This gave 21 mg (15% of theory) of the product as a solid. For further purification, the filtrate was purified by preparative HPLC (Chromasil, water/acetonitrile+0.1% TFA). This gave another 70 mg (50% of theory) of the product.

Total yield: 91 mg (65% of theory)

$^1$H—NHR (400 MHz, DMSO-$d_6$): δ=12.23 (s, 1H), 11.39 (s, 1H), 8.08 (s, 1H), 7.93 (d, 2H), 7.58 (d, 2H), 7.46-7.38 (m, 3H), 7.30-7.27 (m, 2H), 4.72 (s, 2H).

LC-MS (Method 3): $R_t$=2.80 min; MS (ESIpos): m/z=504 [M+H]$^+$.

Example 12

7-({[2-(4-Chlorophenyl)-1,3-thiazol-4-yl]methyl}sulfanyl)-5-[4-(2-hydroxyethoxy)phenyl]-2,4-dioxo-1,2,3,4-tetrahydropyrido[2,3-d]pyrimidine-6-carbonitrile

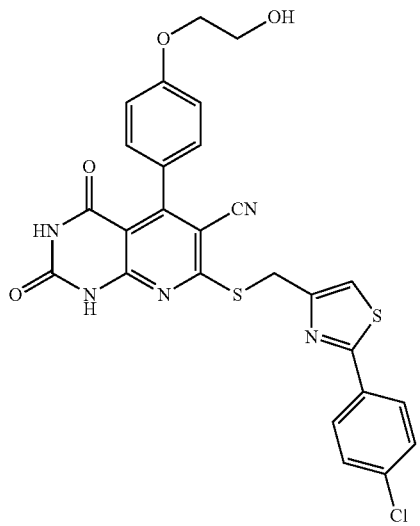 [SMILES: N#Cc1c(SCc2csc(-c3ccc(Cl)cc3)n2)nc2[nH]c(=O)[nH]c(=O)c2c1-c1ccc(OCCO)cc1]

100 mg (0.229 mmol) of the compound from Example 11A were dissolved in 0.46 ml of DMF, 21 mg (0.274 mmol) of sodium sulfide were added and the mixture was stirred at RT overnight. 33 mg (0.137 mmol) of 4-(chloromethyl)-2-(4-chlorophenyl)-1,3-thiazole and 23 mg (0.275 mmol) of sodium bicarbonate were then added, and the reaction solution was stirred at RT for 2 h. Water was added to the reaction mixture for further purification via a preparative HPLC (Chromasil, water/acetonitrile+0.1% TFA) purified.

Yield: 39 mg (75% of theory)

$^1$H—NHR (400 MHz, DMSO-$d_6$): δ=12.20 (s, 1H), 11.36 (s, 1H), 8.06 (s, 1H), 7.94 (d, 2H), 7.58 (d, 2H), 7.21 (d, 2H), 6.98 (d, 2H), 4.89 (t, 1H), 4.72 (s, 2H), 4.05 (t, 2H), 3.73 (q, 2H).

LC-MS (Method 6): $R_t$=1.21 min; MS (ESIpos): m/z=564 [M+H]$^+$.

Example 13

Methyl 4-(4-{[(3-cyano-4-phenyl-6,7-dihydro-5H-cyclopenta[b]pyridin-2-yl)sulfanyl]methyl}-1,3-thiazol-2-yl)benzoate

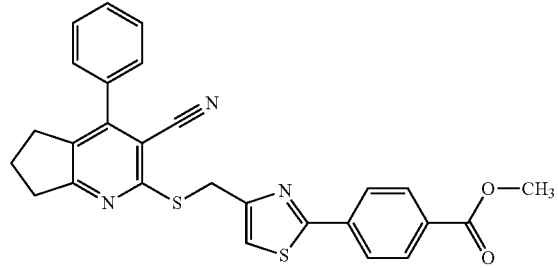 [SMILES: COC(=O)c1ccc(-c2nc(CSc3nc4c(c(-c5ccccc5)c3C#N)CCC4)cs2)cc1]

315 mg (1.18 mmol) of methyl 4-[4-(chloromethyl)-1,3-thiazol-2-yl]benzoate (prepared as described in WO 2005/011685) and 329 mg (3.92 mmol) of sodium bicarbonate are added to the reaction mixture from Example 18A, and the mixture is stirred at RT for 16 h. 50 ml of water were added, and the reaction was extracted with ethyl acetate. The organic phase was washed with water and a saturated aqueous sodium chloride solution, dried over magnesium sulfate and freed from the solvent on a rotary evaporator. The residue was purified by preparative HPLC (column: YMC GEL ODS-AQ S-5, 15 μm; mobile phase gradient: acetonitrile/water 10:90→95:5).

Yield: 100 mg (21% of theory)

$^1$H—NHR (400 MHz, DMSO-$d_6$): δ=8.08 (s, 4H), 7.77 (s, 1H), 7.53 (m, 5H), 4.74 (s, 2H), 3.88 (s, 3H), 3.12 (t, 2H), 2.80 (t, 2H), 2.07 (m, 2H).

LC-MS (Method 4): $R_t$=4.68 min; MS (ESIpos): m/z=483 [M+H]$^+$.

Example 14

4-(4-{[(3-Cyano-4-phenyl-6,7-dihydro-5H-cyclopenta[b]pyridin-2-yl)sulfanyl]methyl}-1,3-thiazol-2-yl)benzoic acid

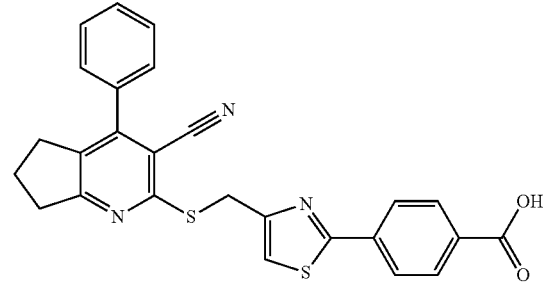 [SMILES: N#Cc1c(SCc2csc(-c3ccc(C(=O)O)cc3)n2)nc2c(c1-c1ccccc1)CCC2]

80 mg (0.17 mmol) of the compound from Example 13 were dissolved in 1.7 ml of dioxane, and 0.33 ml of a 1N aqueous sodium hydroxide solution were added. The reaction mixture was stirred at 50° C. for 3 h. 0.36 ml of 1N hydrochloric acid was then added to the mixture, and the resulting precipitate was filtered off, washed with water and dried.

Yield: 58 mg (72% of theory)

$^1$H—NHR (400 MHz, DMSO-$d_6$): δ=13.19 (s, 1H), 8.06 (s, 4H), 7.77 (s, 1H), 7.53 (m, 5H), 4.73 (s, 2H), 3.13 (t, 2H), 2.80 (t, 2H), 2.07 (m, 2H).

LC-MS (Method 4): $R_t$=4.16 min; MS (ESIpos): m/z=469 [M+H]$^+$.

Example 15

2-({[2-(4-Chlorophenyl)-1,3-thiazol-4-yl]methyl}sulfanyl)-5-oxo-4-(1H-pyrazol-3-yl)-5,6-dihydro-1,6-naphthyridine-3-carbonitrile

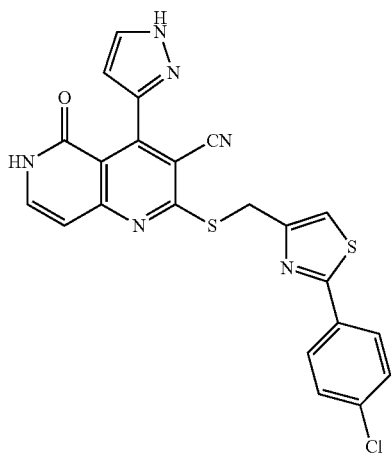 [SMILES: N#Cc1c(SCc2csc(-c3ccc(Cl)cc3)n2)nc2cc[nH]c(=O)c2c1-c1cc[nH]n1]

At 40° C., 28 mg (0.06 mmol) of Example 20A and 14 mg (0.06 mmol) of 2,3-dichloro-5,6-dicyano-1,4-benzoquinone in 1 ml of DMSO were stirred overnight. The reaction mixture was purified by preparative HPLC (Chromasil, water/acetonitrile+0.1% TFA).

Yield: 10 mg (36% of theory)

$^1$H—NHR (400 MHz, DMSO-$d_6$): δ=13.08 (br s, 1H), 11.58 (br s, 1H), 7.95 (d, 2H), 7.82-7.70 (m, 2H), 7.63 (t, 1H), 7.58 (d, 2H), 6.71 (d, 1H), 6.39 (br s, 1H), 4.79 (d, 2H).

LC-MS (Method 3): $R_t$=2.44 min; MS (ESIpos): m/z=477 [M+H]$^+$.

Example 16

2-{[2-(4-Chlorophenyl)-1,3-thiazol-4-yl]methoxy}-4-[4-(2-hydroxyethoxy)phenyl]-5-oxo-5,6-dihydro-1,6-naphthyridine-3-carbonitrile

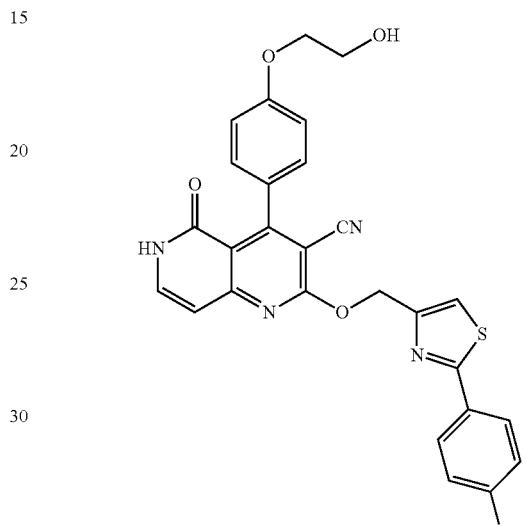

64 mg (0.57 mmol) of potassium tert-butoxide were suspended in 3.5 ml of DMF, 96 mg (0.42 mmol) of [2-(4-chlorophenyl)-1,3-thiazol-4-yl]methanol [Simiti, I. et al. Arch. Pharm. 1972, 305, 509-515] and then 100 mg (0.28 mmol) of the compound from Example 21A were added and the mixture was stirred at 60° C. for 16 h. Another 64 mg (0.57 mmol) of potassium tert-butoxide were added, and the reaction was stirred once more at 80° C. overnight. Water was added, and the reaction solution was extracted 3 times with ethyl acetate. The organic phase was dried over magnesium sulfate, filtered off and concentrated on a rotary evaporator, The crude product was and purified by preparative HPLC (Chromasil, water/acetonitrile).

Yield: 7 mg (5% of theory)

$^1$H—NHR (400 MHz, DMSO-$d_6$): δ=11.47 (br s, 1H), 7.98 (d, 2H), 7.91 (s, 1H), 7.63-7.55 (m, 3H), 7.23 (d, 2H), 6.98 (d, 2H), 6.56 (d, 1H), 5.72 (s, 2H), 4.90 (t, 1H), 4.06 (t, 2H), 3.76 (q, 2H).

LC-MS (Method 3): $R_t$=2.52 min; MS (ESIpos): m/z=531 [M+H]$^+$.

Example 17

7-({[2-(4-Chlorophenyl)-1,3-thiazol-4-yl]methyl}sulfanyl)-5-[4-(2-hydroxyethoxy)phenyl]-2,2-dimethyl-4-oxo-1,2,3,4-tetrahydropyrido[2,3-d]pyrimidine-6-carbonitrile

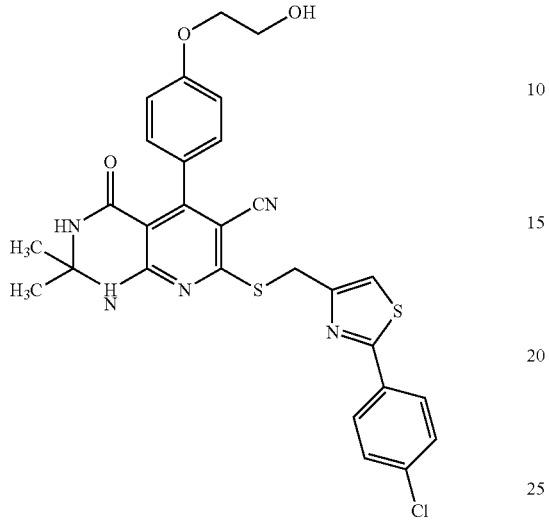

50 mg (0.093 mmol) of the compound from Example 22A were initially charged in 2 ml of acetone, a spatula tip of 4-toluenesulfonic acid monohydrate was added and the mixture was stirred at reflux for 1 h. After cooling, the reaction solution was concentrated and the residue was purified directly by preparative HPLC (Chromasil, water/acetonitrile+0.1% TFA).

Yield: 30 mg (56% of theory)

$^1$H—NHR (400 MHz, DMSO-$d_6$): δ=8.80 (s, 1H), 8.12 (s, 1H), 7.96 (d, 2H), 7.82 (s, 1H), 7.58 (d, 2H), 7.18 (d, 2H), 6.92 (d, 2H), 4.89 (t, 1H), 4.67 (s, 2H), 4.03 (t, 2H), 3.73 (q, 2H), 1.50 (s, 6H).

LC-MS (Method 6): $R_t$=1.29 min; MS (ESIpos): m/z=578 [M+H]$^+$.

Example 18

7-({[2-(4-Chlorophenyl)-1,3-thiazol-4-yl]methyl}sulfanyl)-5-[4-(2-hydroxyethoxy)phenyl]-2-methyl-4-oxo-1,2,3,4-tetrahydropyrido[2,3-d]pyrimidine-6-carbonitrile

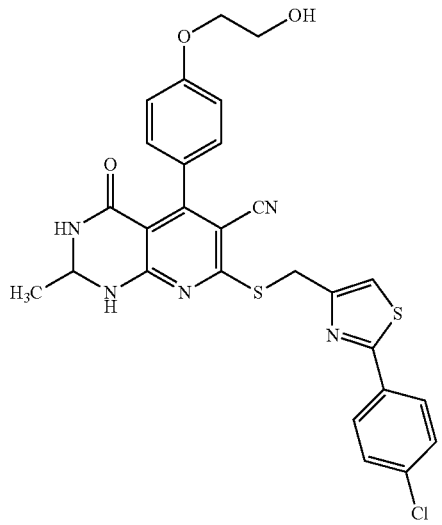 [SMILES: CC1NC(=O)c2c(nc(SCc3csc(-c4ccc(Cl)cc4)n3)c(C#N)c2-c2ccc(OCCO)cc2)N1]

Under argon, 138 mg (0.256 mmol) of the compound from Example 22A were initially charged in 3 ml of acetaldehyde, a spatula tip of 4-toluenesulfonic acid monohydrate was added and the mixture was stirred at RT for 1 h. 2.5 ml of methanol were then added to the reaction solution, and after 2 h the mixture was concentrated and the residue was purified by column chromatography (silica gel, toluene/acetonitrile 2:1→1:1).

Yield: 14 mg (10% of theory)

$^1$H—NHR (400 MHz, DMSO-$d_6$): δ=8.74 (s, 1H), 8.05 (s, 1H), 7.97 (d, 2H), 7.82 (s, 1H), 7.58 (d, 2H), 7.20 (d, 2H), 6.92 (d, 2H), 5.02 (q, 1H), 4.89 (t, 1H), 4.68 (s, 2H), 4.03 (t, 2H), 3.73 (q, 2H), 1.41 (d, 3H).

LC-MS (Method 3): $R_t$=2.41 min; MS (ESIpos): m/z=564 [M+H]$^+$.

Example 19

7-({[2-(4-Chlorophenyl)-1,3-oxazol-4-yl]methyl}sulfanyl)-5-[4-(2-hydroxyethoxy)phenyl]-2-methyl-4-oxo-3,4-dihydropyrido[2,3-d]pyrimidine-6-carbonitrile

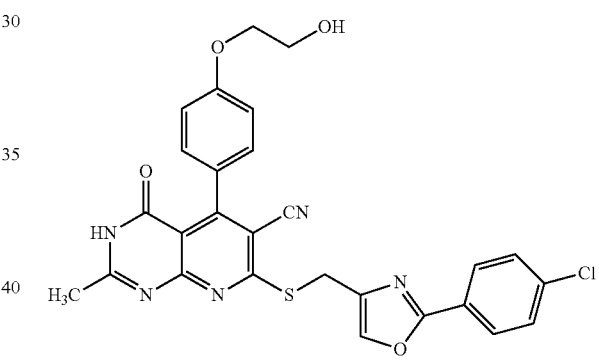

95 mg (0.162 mmol) of 2-{4-[7-({[2-(4-chlorophenyl)-1,3-oxazol-4-yl]methyl}sulfanyl)-6-cyano-2-methyl-4-oxo-3,4-dihydropyrido[2,3-d]pyrimidin-5-yl]phenoxy}ethyl acetate were initially charged in 10 ml of a dioxane/water mixture 2:1, 7.7 mg (0.323 mmol) of lithium hydroxide were added and the mixture was stirred at RT for 5 h. The reaction mixture was then diluted with water, acidified with 1N hydrochloric acid and extracted with ethyl acetate. The organic phase was dried over sodium sulfate, the drying agent was filtered off and the filtrate was concentrated. The residue was purified by preparative HPLC (mobile phase gradient: acetonitrile/water 10:90→95:5, with 0.1% TFA added). This gave 88 mg (99% of theory) of the target compound.

$^1$H—NHR (400 MHz, DMSO-$d_6$): δ=11.15 (s, 1H), 8.30 (s, 1H), 7.97 (d, 2H), 7.61 (d, 2H), 7.54 (d, 2H), 7.16 (d, 2H), 4.57 (s, 2H), 4.09 (t, 2H), 3.75 (t, 2H), 2.25 (s, 3H).

LC-MS (Method 6): $R_t$=1.27 min; MS (ESIpos): m/z=546 [M+H]$^+$.

Example 20

7-({[2-(4-Chlorophenyl)-1,3-thiazol-4-yl]methyl}sulfanyl)-5-[4-(2-hydroxyethoxy)phenyl]-2-(2-methoxyethyl)-4-oxo-3,4-dihydropyrido[2,3-d]pyrimidine-6-carbonitrile

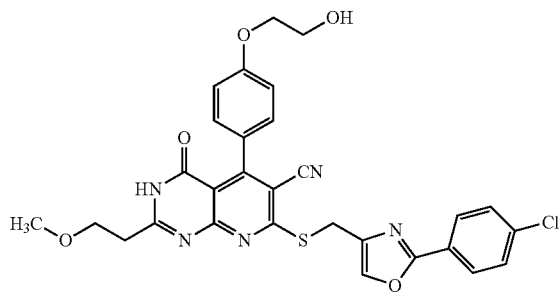 [SMILES: COCCc1nc2nc(SCc3coc(-c4ccc(Cl)cc4)n3)c(C#N)c(-c3ccc(OCCO)cc3)c2c(=O)[nH]1]

731 mg (3.846 mmol) of 3-methoxypropanoic anhydride were added to 100 mg (0.192 mmol) of 2-amino-6-({[2-(4-chlorophenyl)-1,3-thiazol-4-yl]methyl}sulfanyl)-4-[4-(2-hydroxyethoxy)phenyl]pyridine-3,5-dicarbonitrile, and the mixture was stirred at 140° C. for 1 h. The reaction mixture was then purified by preparative HPLC (mobile phase gradient: acetonitrile/water 10:90-95:5, with 0.1% TFA added). This gave 51 mg (44% of theory) of the target compound.

$^1$H—NHR (400 MHz, DMSO-$d_6$): δ=8.41-8.02 (m, 1H), 7.95 (d, 2H), 7.92 (s, 1H), 7.57 (d, 2H), 7.48 (d, 2H), 7.12 (d, 2H), 4.64 (s, 2H), 4.40-4.38 (m, 2H), 4.29-4-27 (m, 2H), 3.55 (t, 2H), 3.20 (s, 3H), 2.57 (t, 2H).

LC-MS (Method 6): $R_t$=1.48 min; MS (ESIpos): m/z=606 [M+H]$^+$.

Example 21

7-({[2-(4-Chlorophenyl)-1,3-thiazol-4-yl]methyl}sulfanyl)-2-ethyl-5-[4-(2-hydroxyethoxy)phenyl]-oxo-3,4-dihydropyrido[2,3-d]pyrimidine-6-carbonitrile

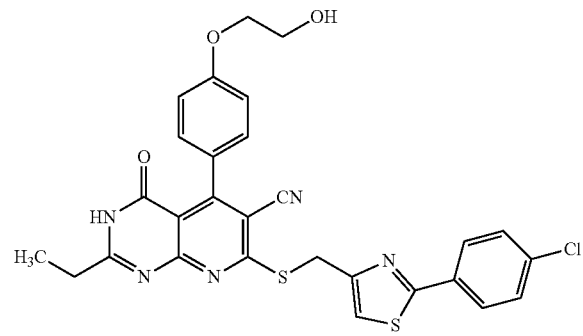 [SMILES: CCc1nc2nc(SCc3csc(-c4ccc(Cl)cc4)n3)c(C#N)c(-c3ccc(OCCO)cc3)c2c(=O)[nH]1]

40 mg (0.063 mmol) of 2-{4-[7-({[2-(4-chlorophenyl)-1,3-thiazol-4-yl]methyl}sulfanyl)-6-cyano-2-ethyl-4-oxo-3,4-dihydropyrido[2,3-d]pyrimidin-5-yl]phenoxy}ethyl propanoate were initially charged in 4 ml of a dioxane/water mixture 2:1, 3 mg (0.127 mmol) of lithium hydroxide were added and the mixture was stirred at RT. After 3 h, the reaction mixture was purified by preparative HPLC (mobile phase gradient: acetonitrile/water 10:90→95:5, with 0.1% TFA added). This gave 27 mg (70% of theory) of the target compound.

$^1$H—NHR (400 MHz, DMSO-$d_6$): δ=11.13 (s, 1H), 7.95 (d, 2H), 7.85 (s, 1H), 7.57 (d, 2H), 7.54 (d, 2H), 7.16 (d, 2H), 4.77 (s, 2H), 4.09 (t, 2H), 3.75 (t, 2H), 2.55-2.52 (m, 2H), 1.12 (t, 3H).

LC-MS (Method 6): $R_t$=1.39 min; MS (ESIpos): m/z=576 [M+H]$^+$.

B. Assessing the Pharmacological and Physiological Activity

The pharmacological and physiological activity of the compounds according to the invention can be demonstrated in the following assays:

B-1. Indirect Determination of the Adenosine Agonism by Way of Gene Expression

Cells of the CHO (Chinese Hamster Ovary) permanent line are transfected stably with the cDNA for the adenosine receptor subtypes A1, A2a and A2b. The adenosine A1 receptors are coupled to the adenylate cyclase by way of $G_i$ proteins, while the adenosine A2a and A2b receptors are coupled by way of $G_s$ proteins. In correspondence with this, the formation of cAMP in the cell is inhibited or stimulated, respectively. After that, expression of the luciferase is modulated by way of a cAMP-dependent promoter. The luciferase test is optimized, with the aim of high sensitivity and reproducibility, low variance and good suitability for implementation on a robot system, by varying several test parameters, such as cell density, duration of the growth phase and the test incubation, forskolin concentration and medium composition. The following test protocol is used for pharmacologically characterizing cells and for the robot-assisted substance screening:

The stock cultures are grown, at 37° C. and under 5% $CO_2$, in DMEM/F12 medium containing 10% FCS (fetal calf serum) and in each case split 1:10 after 2-3 days. The test cultures are seeded in 384-well plates with 2000 cells per well and grown at 37° C. for approx. 48 hours. The medium is then replaced with a physiological sodium chloride solution (130 mM sodium chloride, 5 mM potassium chloride, 2 mM calcium chloride, 20 mM HEPES, 1 mM magnesium chloride hexahydrate, 5 mM sodium bicarbonate, pH 7.4). The substances to be tested, which are dissolved in DMSO, are pipetted into the test cultures (maximum final concentration of DMSO in the test mixture: 0.5%) in a dilution series of from $5 \times 10^{-11}$M to $3 \times 10^{-6}$M (final concentration). 10 minutes later, forskolin is added to the A1 cells and all the cultures are subsequently incubated at 37° C. for four hours. After that, 35 μl of a solution which is composed of 50% lysis reagent (30 mM disodium hydrogenphosphate, 10% glycerol, 3% TritonX100, 25 mM TrisHCl, 2 mM dithiothreitol (DTT), pH 7.8) and 50% luciferase substrate solution (2.5 mM ATP, 0.5 mM luciferin, 0.1 mM coenzyme A, 10 mM tricine, 1.35 mM magnesium sulfate, 15 mM DTT, pH 7.8) are added to the test cultures, which are shaken for approx. 1 minute and the luciferase activity is measured using a camera system. The $EC_{50}$ values are determined, i.e., the concentrations at which 50% of the luciferase answer is inhibited in the case of the A1 cell, and, respectively, 50% of the maximum stimulation with the corresponding substance is achieved in the case of the A2b and A2a cells. The adenosine-analogous compound NECA (5-N-ethylcarboxamidoadenosine), which binds to all adenosine receptor subtypes with high affinity and possesses an agonistic effect, is used in these experiments as the reference compound [Klotz, K. N., Hessling, J., Hegler, J., Owman, C., Kull, B., Fredholm, B. B., Lohse, M. J., "Comparative pharmacology of human adenosine receptor subtypes—characterization of stably transfected receptors in CHO cells", Naunyn Schmiedebergs Arch. Pharmacol., 357 (1998), 1-9).

Table 1 below lists the EC50 values of representative working examples for the receptor stimulation on adenosine A1, A2a and A2b receptor subtypes:

TABLE 1

| Example No. | EC50 A1 [nM] (1 μM forskolin) | EC50 A2a [nM] | EC50 A2b [nM] |
|---|---|---|---|
| 2 | 7.9 | >3000 | 207 |
| 3 | 2.6 | >3000 | 66 |
| 9 | <0.04 | 68 | 38 |
| 10 | 0.4 | 1370 | 213 |
| 12 | 2 | 2000 | 880 |
| 13 | 21 | 3000 | 1250 |

B-2. Studies on Isolated Blood Vessels

The caudal artery of anesthetized rats is excised and mounted in a conventional apparatus for measuring isolated blood vessels. The vessels are perfused in a heated bath and contracted using phenylephrine. The extent of the contraction is determined using a contraction meter. Test substances are added to the precontracted blood vessels, and the reduction of the contraction of the vessels is measured. A reduction of contraction corresponds to a dilation of the vessels. The concentration at which the contraction of the blood vessels is reduced by 50% is given as the $EC_{50}$ value of a test substance with respect to its relaxing properties.

B-3. Measurement of Blood Pressure and Heart Rate on Awake Rats

Various dosages of test substances are administered orally to awake SHR rats (spontaneously hypertensive rats) carrying an internal transmitter capable of measuring permanently both blood pressure and heart rate (telemetric monitoring of hemodynamic parameters). Blood pressure, heart rate and their changes are then recorded over a period of 24 hours.

B-4. Measurement of Blood Pressure and Heart Rate on Awake Marmosets

Various concentrations of the test substances are administered orally to awake marmosets which carry an internal transmitter capable of measuring permanently both blood pressure and heart rate (telemetric monitoring of hemodynamic parameters). Blood pressure, heart rate and their changes are then recorded for a period of 6-24 hours.

B-5. Indirect Determination of Adenosine Antagonism Via Gene Expression

Cells of the permanent line CHO K1 (Chinese Hamster Ovary) are stably transfected with a reporter construct (CRE luciferase) and the cDNA for the adenosine receptor subtypes A2a or A2b. A2a or A2b receptors are coupled via Gαs proteins to adenylate cyclase. Through receptor activation, the adenylate cyclase is activated and therefore the cAMP level in the cell is increased. Via the reporter construct, a cAMP-dependent promoter, the change in the cAMP level is coupled to luciferase expression. For determination of adenosine antagonism on the adenosine receptor subtype A1, once again CHO K1 cells are stably transfected, but this time with a $Ca^{2+}$-sensitive reporter construct (NFAT-TA-Luc; Clontech) and an A1-Gα16 fusion construct. This receptor chimera is, in contrast to the native A1 receptor (Gαi-coupling), coupled to phospholipase C. The luciferase is expressed here as a function of the cytosolic $Ca^{2+}$ concentration.

The permanent cell lines are cultured in DMEM/F12 (Cat. No. BE04-687Q; BioWhittaker) with 10% FCS (fetal calf serum) and various additives (20 ml/liter 1M HEPES (Cat. No. 15630; Gibco), 20 ml/liter GlutaMAX (Cat. No. 35050-038, Gibco), 14 ml/liter MEM sodium pyruvate (Cat. No. 11360-039; Gibco) 10 ml/liter PenStrep (Cat. No. 15070-063; Gibco)) at 37° C. under 5% carbon dioxide, and split twice weekly.

For testing in the 384-well plate format, the cells are sown at 2000 cells/well in 25/well sowing medium and cultured at 37° C. under 5% carbon dioxide until substance testing. The A2a and A2b cells are sown, 24 h before substance testing, in medium with additives and 5% FCS, the base medium used for the A2a cells being DMEM/F12 and the base medium used for the A2b cells being OptiMEM (Cat. No. 31985-047; Gibco). The A1-Gα16 cells are sown, 48 h before substance testing, in OptiMEM with 2.5% dialysed FCS and additives. On the day of the test, prior to the addition of the substance, the medium is replaced by 25 μl of Cafty buffer (Cat. No. T21-154; PAA) with 2 mM calcium chloride and 0.1% BSA (bovine serum albumin). Dilution series in Cafty buffer with 2 mM calcium chloride and 0.1% BSA (bovine serum albumin) and a suitable agonist concentration are prepared from the substances to be tested, which are dissolved in DMSO. The substances are pipetted at a final concentration from $5 \times 10^{-5}$ M to $2.56 \times 10^{-11}$ M to the test cultures, with the DMSO content on the cells not exceeding 0.5%. NECA (5-N-ethyl-carboxamido-adenosine) at a final concentration of 30 nM, which roughly corresponds to the $EC_{50}$ concentration, is used as agonist for the A2a and A2b cells. 25 nM CPA (N6-cyclopentyl adenosine), which roughly corresponds to the $EC_{75}$ concentration, is used as agonist for the A1-Gα16 cells. After adding the substances, the cell plates are incubated for 3-4 h at 37° C. under 5% carbon dioxide. Then 25 μl of a solution consisting to 50% of lysis reagent (30 nM disodium hydrogen phosphate, 10% glycerol, 3% Triton X-100, 25 mM TrisHCl, 2 mM dithiothreitol (DTT), pH 7.8) and to 50% of luciferase substrate solution (2.5 mM ATP, 0.5 mM luciferin, 0.1 mM coenzyme A, 10 mM Tricin, 1.35 mM magnesium sulfate, 15 mM DTT, pH 7.8) is added to the cells directly before measurement. The luciferase activity is detected with a luminescence reader. The $IC_{50}$ values are determined, i.e. the concentration at which the luciferase response, produced by the respective agonist, is inhibited to 50%. ZM241385, for the A2a and A2b cells, and DPCPX (1,3-dipropyl-8-cyclo-pentylxanthine), for the A1-Gα16 cells, are used as reference antagonist.

C. Working Examples of Pharmaceutical Compositions

The compounds of the invention can be converted into pharmaceutical preparations in the following ways:

Tablet:

Composition:

100 mg of the compound of the invention, 50 mg of lactose (monohydrate), 50 mg of maize starch (native), 10 mg of polyvinylpyrrolidone (PVP 25) (from BASF, Ludwigshafen, Germany) and 2 mg of magnesium stearate.

Tablet weight 212 mg, diameter 8 mm, radius of curvature 12 mm.

Production:

The mixture of compound of the invention, lactose and starch is granulated with a 5% strength solution (m/m) of the PVP in water. The granules are dried and mixed with the magnesium stearate for 5 minutes. This mixture is compressed in a conventional tablet press (see above for format of the tablet). A guideline compressive force for the compression is 15 kN.

Suspension which can be Administered Orally:
Composition:
    1000 mg of the compound of the invention, 1000 mg of ethanol (96%), 400 mg of Rhodigel® (xanthan gum from FMC, Pennsylvania, USA) and 99 g of water.
    10 ml of oral suspension correspond to a single dose of 100 mg of the compound of the invention.
Production:
    The Rhodigel is suspended in ethanol, and the compound of the invention is added to the suspension. The water is added while stirring. The mixture is stirred for about 6 h until the swelling of the Rhodigel is complete.
Solution which can be Administered Orally:
Composition:
    500 mg of the compound of the invention, 2.5 g of polysorbate and 97 g of polyethylene glycol 400.20 g of oral solution correspond to a single dose of 100 mg of the compound of the invention.
Production:
    The compound of the invention is suspended in the mixture of polyethylene glycol and polysorbate with stirring. The stirring process is continued until the compound of the invention has completely dissolved.
i.v. Solution:
    The compound of the invention is dissolved in a concentration below the saturation solubility in a physiologically tolerated solvent (e.g. isotonic saline, 5% glucose solution and/or 30% PEG 400 solution). The solution is sterilized by filtration and used to fill sterile and pyrogen-free injection containers.

The invention claimed is:
1. A compound of the formula (I)

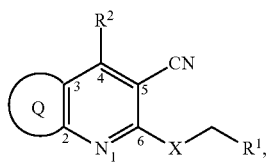

(I)

in which
ring Q represents a group of the formula

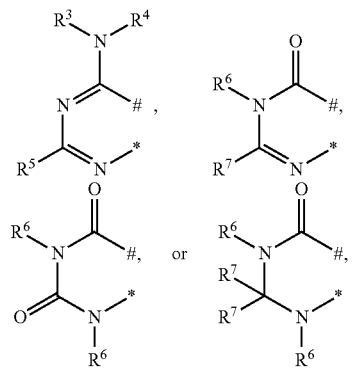

where
* represents in each case the point of attachment to the C2 atom,
# represents in each case the point of attachment to the C3 atom, $R^3$ represents hydrogen or $(C_1-C_4)$-alkyl,
$R^4$ represents hydrogen or $(C_1-C_4)$-alkyl,
$R^5$ represents hydrogen, $(C_1-C_4)$-alkyl or amino,
$R^6$ represents in each case hydrogen, $(C_1-C_4)$-alkyl or allyl,
in which $(C_1-C_4)$-alkyl may be substituted by a substituent selected from the group consisting of hydroxycarbonyl, $(C_1-C_4)$-alkoxycarbonyl and amino,
$R^7$ represents in each case hydrogen, $(C_1-C_4)$-alkyl, trifluoromethyl, amino, mono-$(C_1-C_4)$-alkylamino or di-$(C_1-C_4)$-alkylamino,
in which $(C_1-C_4)$-alkyl may be substituted by 1 or 2 substituents independently of one another selected from the group consisting of hydroxyl, methoxy and amino, and either
i) $R^{8A}$ represents in each case hydrogen, hydroxyl, $(C_1-C_4)$-alkoxy or mono-$(C_1-C_4)$-alkylamino,
in which $(C_2-C_4)$-alkoxy and mono-$(C_2-C_4)$-alkylamino may be substituted by a hydroxyl substituent,
and
$R^{8B}$ represents hydrogen,
or
$R^{8A}$ together with $R^{8B}$ forms an oxo, N—$(C_1-C_4)$-alkylimino, N—$(C_1-C_4)$-alkoxyimino or $(C_1-C_4)$-alkoxycarbonylmethylidene group,
and
$R^{9A}$ and $R^{9B}$ independently of one another represent in each case hydrogen or $(C_1-C_4)$-alkyl or together with the carbon atom to which they are attached form a spiro-linked 3-to 5-membered cycloalkyl ring,
and
$R^{10}$ represents hydrogen, $(C_1-C_4)$-alkyl or phenyl,
in which $(C_1-C_4)$-alkyl may be substituted by 1 or 2 substituents independently of one another selected from the group consisting of hydroxyl and amino,
X represents S or O,
$R^1$ represents a 5- to 10-membered heteroaryl,
where $(C_6-C_{10})$-aryl and 5- to 10-membered heteroaryl may be substituted by 1 or 2 substituents independently of one another selected from the group consisting of halogen, nitro, cyano, $(C_1-C_6)$-alkyl, trifluoromethyl, hydroxyl, $(C_1-C_6)$-alkoxy, amino, mono-$(C_1-C_6)$-alkylamino, di-$(C_1-C_6)$-alkylamino, hydroxycarbonyl, $(C_1-C_6)$-alkoxycarbonyl, aminocarbonyl, mono-$(C_1-C_6)$-alkylaminocarbonyl, di-$(C_1-C_6)$-alkylaminocarbonyl, pyrrolidino, piperidino, morpholino, piperazino and N'-$(C_1-C_4)$-alkylpiperazino, phenyl and 5- or 6-membered heteroaryl,
in which phenyl and 5- or 6-membered heteroaryl may be substituted by 1 to 3 substituents independently of one another selected from the group consisting of halogen, nitro, cyano, $(C_1-C_6)$-alkyl, difluoromethyl, trifluoromethyl, hydroxyl, $(C_1-C_6)$-alkoxy, difluoromethoxy, trifluoromethoxy, amino, mono-$(C_1-C_6)$-alkylamino, di-$(C_1-C_6)$-alkyl-amino, hydroxycarbonyl and $(C_1-C_6)$-alkoxycarbonyl,
$R^2$ represents $(C_5-C_6)$-cycloalkyl, 5- or 6-membered heterocyclyl, phenyl or 5- or 6-membered heteroaryl,
where $(C_5-C_6)$-cycloalkyl may be substituted by 1 or 2 substituents independently of one another selected from the group consisting of $(C_1-C_6)$-alkyl, hydroxyl, oxo, $(C_1-C_6)$-alkoxy, amino, mono-$(C_1-C_6)$-alkylamino and di-$(C_1-C_6)$-alkylamino,
in which $(C_1-C_6)$-alkyl and $(C_1-C_6)$-alkoxy may be substituted by 1 or 2 substituents independently of one another selected from the group consisting of hydroxyl, $(C_1-C_4)$-alkoxy and $(C_3-C_7)$-cycloalkyl, in which ($C_3$-$C_7$)-cycloalkyl for its part may be substituted by 1 or 2 substituents independently of one another selected from the group consisting of ($C_1$-$C_4$)-alkyl, hydroxyl, oxo and ($C_1$-$C_4$)-alkoxy, and where 5- or 6-membered heterocyclyl may be substituted by 1 to 3 substituents independently of one another selected from the group consisting of oxo, thioxo, hydroxyl, ($C_1$-$C_6$)-alkyl, ($C_1$-$C_6$)-alkoxy, ($C_1$-$C_6$)-alkylcarbonyl, amino, mono-($C_1$-$C_6$)-alkylamino, di-($C_1$-$C_6$)-alkylamino and ($C_3$-$C_7$)-cycloalkyl, in which ($C_1$-$C_6$)-alkyl may be substituted by 1 to 3 substituents independently of one another selected from the group consisting of fluorine, oxo, hydroxyl, trifluoromethyl, ($C_1$-$C_4$)-alkoxy, ($C_1$-$C_4$)-alkylcarbonyloxy, amino, mono-($C_1$-$C_4$)-alkylamino, di-($C_1$-$C_4$)-alkylamino and ($C_3$-$C_7$)-cycloalkyl, in which ($C_3$-$C_7$)-cycloalkyl for its part may be substituted by 1 or 2 substituents independently of one another selected from the group consisting of ($C_1$-$C_4$)-alkyl, hydroxyl, oxo and ($C_1$-$C_4$)-alkoxy, and in which ($C_1$-$C_6$)-alkylcarbonyl may be substituted by a substituent selected from the group consisting of hydroxyl and ($C_1$-$C_4$)-alkoxy, and in which ($C_3$-$C_7$)-cycloalkyl may be substituted by 1 or 2 substituents independently of one another selected from the group consisting of ($C_1$-$C_4$)-alkyl, hydroxyl, oxo and ($C_1$-$C_4$)-alkoxy, and where phenyl and 5- or 6-membered heteroaryl may be substituted by 1 to 3 substituents independently of one another selected from the group consisting of halogen, cyano, hydroxyl, ($C_1$-$C_6$)-alkyl, ($C_1$-$C_6$)-alkoxy, ($C_3$-$C_7$)-cycloalkoxy and —$NR^A R^B$, in which ($C_1$-$C_6$)-alkyl may be substituted by 1 to 3 substituents selected from the group consisting of fluorine, and in which ($C_1$-$C_6$)-alkoxy may be substituted by 1 to 3 substituents independently of one another selected from the group consisting of fluorine, trifluoromethyl, ($C_3$-$C_7$)-cycloalkyl, oxo, hydroxyl, ($C_1$-$C_4$)-alkoxy, hydroxycarbonyl, amino, mono-($C_1$-$C_4$)-alkylamino and di-($C_1$-$C_4$)-alkylamino, and in which ($C_3$-$C_7$)-cycloalkoxy may be substituted by 1 or 2 substituents independently of one another selected from the group consisting of ($C_1$-$C_4$)-alkyl, hydroxyl, oxo and ($C_1$-$C_4$)-alkoxy, and in which $R^A$ represents hydrogen or ($C_1$-$C_6$)-alkyl, in which ($C_1$-$C_6$)-alkyl for its part may be substituted by a substituent selected from the group consisting of hydroxyl and ($C_1$-$C_4$)-alkoxy, $R^B$ represents hydrogen, ($C_1$-$C_6$)-alkyl, ($C_3$-$C_7$)-cycloalkyl, ($C_1$-$C_4$)-alkylsulfonyl or ($C_3$-$C_7$)-cycloalkylsulfonyl, in which ($C_1$-$C_6$)-alkyl for its part may be substituted by 1 or 2 substituents independently of one another selected from the group consisting of ($C_3$-$C_7$)-cycloalkyl, oxo, hydroxyl, ($C_1$-$C_4$)-alkoxy, hydroxycarbonyl, amino, mono-($C_1$-$C_4$)-alkylamino and di-($C_1$-$C_4$)-alkylamino, and in which ($C_3$-$C_7$)-cycloalkyl for its part may be substituted by 1 or 2 substituents independently of one another selected from the group consisting of ($C_1$-$C_4$)-alkyl, hydroxyl, oxo and ($C_1$-$C_4$)-alkoxy, or in which two adjacent substituents at the phenyl together with the carbon atoms to which they are attached may form a 1,3-dioxolane or 2,2-difluoro-1,3-dioxolane, or an N-oxide, salt, or salt of the N-oxide thereof, except for the compounds 5,6,7,8-tetrahydro-2-[[(2-methylphenyl)methyl]thio]-4-(2-thienyl)-3-quinolinecarbonitrile, 5,6,7,8-tetrahydro-2-[(2-phenylmethyl)thio]-4-(2-thienyl)-3-quinolinecarbonitrile, 5,6,7,8-tetrahydro-2-[[(2-methylphenyl)methyl]thio]-4-(4-pyridyl)-3-quinolinecarbonitrile, 5,6,7,8-tetrahydro-2-[(phenylmethyl)thio]-4-phenyl-3-quinolinecarbonitrile, 5,6,7,8-tetrahydro-2-[(phenylmethyl)thio]-4-(4-chlorophenyl)-3-quinolinecarbonitrile, 6,7-dihydro-4-(4-hydroxyphenyl)-2-[(phenylmethyl)thio]-5H-cyclopentapyridine-3-carbonitrile.

2. The compound of the formula (I) as claimed in claim 1 in which ring Q represents a group of the formula

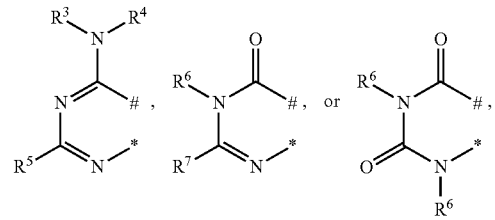

where

* represents in each case the point of attachment to the C2 atom, # represents in each case the point of attachment to the C3 atom, $R^3$ represents hydrogen or methyl, $R^4$ represents hydrogen or methyl, $R^5$ represents hydrogen or methyl, $R^6$ represents in each case hydrogen or methyl, $R^7$ represents in each case hydrogen or methyl, and either i) $R^{8A}$ represents in each case hydrogen or hydroxyl, and $R^{8B}$ represents hydrogen, or ii) $R^{8A}$ together with $R^{8B}$ forms an oxo group, and $R^{9A}$ and $R^{9B}$ independently of one another represent in each case hydrogen or methyl, X represents S or O, $R^1$ represents a 5- or 6-membered heteroaryl, where phenyl and 5- or 6-membered heteroaryl are substituted by 1 or 2 substituents independently of one another selected from the group consisting of fluorine, chlorine, cyano, ($C_1$-$C_4$)-alkyl, trifluoromethyl, hydroxyl, ($C_1$-$C_4$)-alkoxy, amino, hydroxycarbonyl, ($C_1$-$C_4$)-alkoxycarbonyl, aminocarbonyl, phenyl and 5- or 6-membered heteroaryl, in which phenyl and 5- or 6-membered heteroaryl may be substituted by 1 to 3 substituents independently of one another selected from the group consisting of fluorine, chlorine, nitro, cyano, ($C_1$-$C_4$)-alkyl, difluoromethyl, trifluoromethyl, hydroxyl, ($C_1$-$C_4$)-alkoxy, difluoromethoxy, trifluoromethoxy, amino, hydroxycarbonyl and ($C_1$-$C_4$)-alkoxy-carbonyl, R² represents cyclohexyl, tetrahydropyranyl, piperidinyl, piperazinyl, morpholinyl, phenyl, pyrazolyl, imidazolyl, oxazolyl, thiazolyl or pyridyl,
  where cyclohexyl may be substituted by a substituent selected from the group consisting of hydroxyl and $(C_1-C_4)$-alkoxy,
  in which (C2-C4)-alkoxy may be substituted by 1 or 2 substituents independently of one another selected from the group consisting of hydroxyl and methoxy, and
  where piperidinyl, piperazinyl and morpholinyl may be substituted by a substituent selected from the group consisting of $(C_1-C_4)$-alkyl, hydroxyl, $(C_1-C_4)$-alkoxy and $(C_1-C_4)$-alkylcarbonyl,
  in which $(C_1-C_4)$-alkyl may be substituted by 1 or 2 substituents independently of one another selected from the group consisting of hydroxyl, methoxy, ethoxy, methylcarbonyloxy and ethylcarbonyloxy, and
  in which $(C_1-C_4)$-alkylcarbonyl may be substituted by a substituent selected from the group consisting of hydroxyl, methoxy and ethoxy, and
  where phenyl and pyridyl may be substituted by 1 to 3 substituents independently of one another selected from the group consisting of fluorine, chlorine, cyano, hydroxyl, $(C_1-C_4)$-alkyl and $(C_1-C_4)$-alkoxy,
  in which $(C_2-C_4)$-alkoxy may be substituted by 1 or 2 substituents independently of one another selected from the group consisting of oxo, hydroxyl, $(C_1-C_4)$-alkoxy, hydroxycarbonyl and amino, and
  where pyrazolyl, imidazolyl, oxazolyl and thiazolyl may be substituted by 1 or 2 substituents independently of one another selected from the group consisting of fluorine, chlorine, cyano, hydroxyl, $(C_1-C_4)$-alkyl and $(C_1-C_4)$-alkoxy,
  in which (C2-C4)-alkoxy may be substituted by 1 or 2 substituents independently of one another selected from the group consisting of oxo, hydroxyl, $(C_1-C_4)$-alkoxy, hydroxycarbonyl and amino, except for the compound 5,6,7,8-tetrahydro-2-[[(2-methylphenyl)methyl]thio]-4-(4-pyridyl)-3-quinolinecarbonitrile.

3. The compound of the formula (I) as claimed in claim 1 in which
  ring Q represents a group of the formula

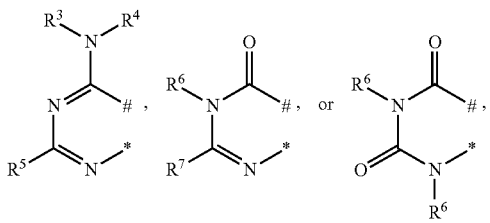

where
  * represents in each case the point of attachment to the C2 atom,
  # represents in each case the point of attachment to the C3 atom,
  $R^3$ represents hydrogen,
  $R^4$ represents hydrogen,
  $R^5$ represents hydrogen or methyl,
  $R^6$ represents in each case hydrogen or methyl, and
  $R^7$ represents hydrogen or methyl,
  X represents S or O,
  $R^1$ represents a 5- or 6-membered heteroaryl,
  where phenyl and 5- or 6-membered heteroaryl are substituted by 1 or 2 substituents independently of one another selected from the group consisting of fluorine, chlorine, cyano, methyl, ethyl, trifluoromethyl, hydroxyl, methoxy, ethoxy, amino, hydroxycarbonyl, methoxycarbonyl, ethoxycarbonyl, aminocarbonyl, phenyl and 5- or 6-membered heteroaryl,
  in which phenyl and 5- or 6-membered heteroaryl may be substituted by 1 to 3 substituents independently of one another selected from the group consisting of fluorine, chlorine, methyl, ethyl, difluoromethyl, trifluoromethyl, hydroxyl, methoxy, ethoxy, amino, hydroxycarbonyl, methoxycarbonyl and ethoxycarbonyl,
  $R^2$ represents phenyl, pyrazolyl or pyridyl,
  where phenyl and pyridyl may be substituted by 1 or 2 substituents independently of one another selected from the group consisting of fluorine, chlorine, cyano, hydroxyl, $(C_1-C_4)$-alkyl and $(C_1-C_4)$-alkoxy,
  in which $(C_2-C_4)$-alkoxy may be substituted by 1 or 2 substituents independently of one another selected from the group consisting of oxo, hydroxyl, $(C_1-C_4)$-alkoxy, hydroxycarbonyl and amino, and
  where pyrazolyl may be substituted by a substituent selected from the group consisting of fluorine, chlorine, cyano, hydroxyl, $(C_1-C_4)$-alkyl and $(C_1-C_4)$-alkoxy,
  in which $(C_2-C_4)$-alkoxy may be substituted by 1 or 2 substituents independently of one another selected from the group consisting of oxo, hydroxyl, $(C_1-C_4)$-alkoxy, hydroxycarbonyl and amino.

4. The compound of the formula (I) as claimed in claim 1, in which
  ring Q represents a group of the formula

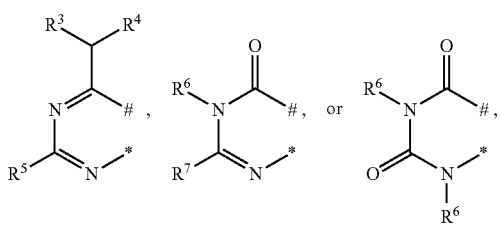

in which
  * represents in each case the point of attachment to the C2 atom,
  # represents in each case the point of attachment to the C3 atom,
  $R^3$ represents hydrogen,
  $R^4$ represents hydrogen,
  $R^5$ represents methyl,
  $R^6$ represents hydrogen, and
  $R^7$ represents hydrogen or methyl,
  X represents S or O,
  $R^1$ represents thiazolyl or oxazolyl,
  where thiazolyl and oxazolyl are substituted by a phenyl substituent,
  in which phenyl may be substituted by a substituent selected from the group consisting of fluorine, chlorine, cyano, methyl, methoxy, hydroxycarbonyl and methoxycarbonyl, and
  where thiazolyl and oxazolyl may be substituted by a substituent selected from the group consisting of fluorine, chlorine, cyano, methyl, ethyl, methoxy, amino, hydroxycarbonyl and methoxycarbonyl, $R^2$ represents a group of the formula

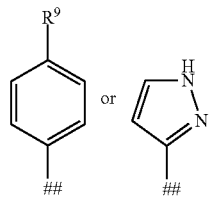

where ## represents the point of attachment to the bicycle, in which $R^9$ represents hydrogen or $(C_1-C_4)$-alkoxy, in which (C2-C4)-alkoxy may be substituted by 1 or 2 hydroxyl substituents.

5. A process for preparing compounds of the formula (I) as defined in claim 1, comprising

[A] reacting a compound of the formula (II)

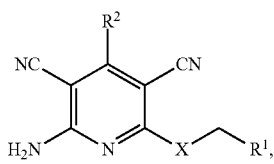

in which X, $R^1$ and $R^2$ each have the meanings given in claim 1, in an inert solvent or in the absence of a solvent with a compound of the formula (III)

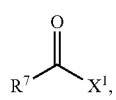

in which $R^7$ has the meaning given in claim 1 and $X^1$ represents hydroxyl or —OC(O)$R^7$, in which $R^7$ has the meaning given above, to give a compound of the formula (I-A)

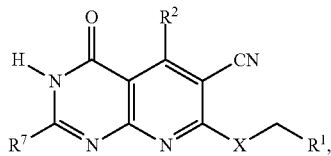

which X, $R^1$, $R^2$ and $R^7$ each have the meanings given above, or

[B] reacting a compound of the formula (II) in an inert solvent or in the absence of a solvent in the presence of a suitable source of ammonia with a compound of the formula (IV)

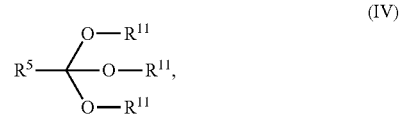

in which $R^5$ has the meaning given in claim 1 and $R^{11}$ represents $(C_1-C_4)$-alkyl, to give compounds of the formula (I-B)

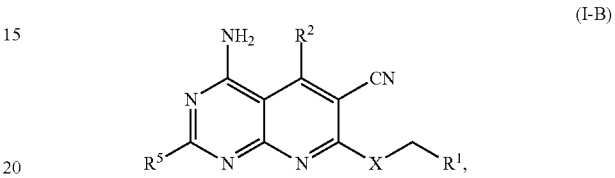

in which X, $R^1$, $R^2$ and $R^5$ each have the meanings given in claim 1, or

[C] reacting a compound of the formula (V)

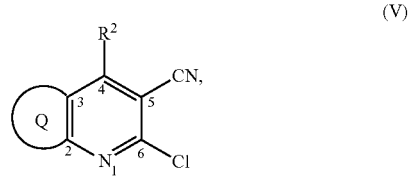

in which $R^2$ has the meaning given in claim 1 and ring Q represents a group of the formula

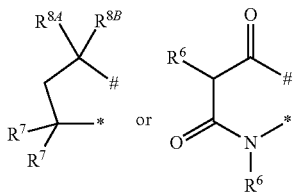

where

* represents in each case the point of attachment to the C2 atom, # represents in each case the point of attachment to the C3 atom, $R^6$ represents hydrogen, $(C_1-C_4)$-alkyl or allyl, in which $(C_1-C_4)$-alkyl may be substituted by a substituent selected from the group consisting of hydroxycarbonyl, $(C_1-C_4)$-alkoxycarbonyl and amino, $R^7$ represents in each case hydrogen or $(C_1-C_4)$-alkyl, and either i) $R^{8A}$ and $R^{8B}$ represent hydrogen, or ii) $R^{8A}$ together with $R^{8B}$ forms an oxo group, in an inert solvent initially with an alkali metal sulfide to give a compound of the formula (VI)

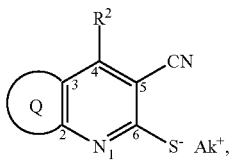
(VI)

in which $R^2$ has the meaning given above,
  $Ak^+$ represents an alkali metal salt, and
  ring Q represents a group of the formula

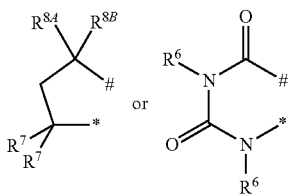

where
  * represents in each case the point of attachment to the C2 atom,
  # represents in each case the point of attachment to the C3 atom,
  $R^6$ represents in each case hydrogen, $(C_1-C_4)$-alkyl or allyl,
  in which $(C_1-C_4)$-alkyl may be substituted by a substituent selected from the group consisting of hydroxycarbonyl, $(C_1-C_4)$-alkoxycarbonyl and amino,
  $R^7$ represents hydrogen or $(C_1-C_4)$-alkyl, and either
  i) $R^{8A}$ and $R^{8B}$ represent hydrogen, or
  ii) $R^{8A}$ together with $R^{8B}$ forms an oxo group,
  in the presence of a suitable base with a compound of the formula (VII)

(VII)

in which $R^1$ has the meaning given in claim 1 and
  $X^2$ represents a suitable leaving group,
  to give a compound of the formula (I-C)

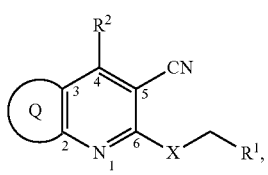
(I-C)

in which $R^1$ and $R^2$ each have the meanings given above, ring Q represents a group of the formula

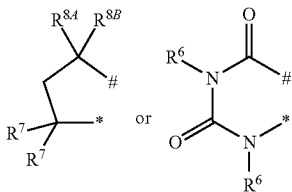

where
  * represents in each case the point of attachment to the C2 atom,
  # represents in each case the point of attachment to the C3 atom,
  $R^6$ represents hydrogen, $(C_1-C_4)$-alkyl or allyl,
  in which $(C_1-C_4)$-alkyl may be substituted by a substituent selected from the group consisting of hydroxycarbonyl, $(C_1-C_4)$-alkoxycarbonyl and amino,
  $R^7$ represents hydrogen or $(C_1-C_4)$-alkyl, and either
  i) $R^{8A}$ and $R^{8B}$ represent hydrogen, or
  ii) $R^{8A}$ together with $R^{8B}$ forms an oxo group, or
  [D] reacting a compound of the formula (V) in an inert solvent in the presence of a base with a compound of the formula (VIII)

(VIII)

in which $R^1$ has the meaning given in claim 1
  to give compounds of the formula (I-D)

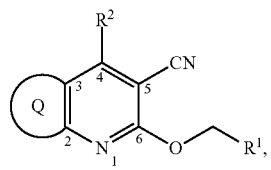
(I-D)

in which $R^1$ and $R^2$ each have the meanings given in claim 1, and
  ring Q represents a group of the formula

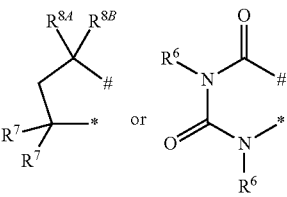

where
  * represents in each case the point of attachment to the C2 atom,
  # represents in each case the point of attachment to the C3 atom,
  $R^6$ represents in each case hydrogen, $(C_1-C_4)$-alkyl or allyl,
  in which $(C_1-C_4)$-alkyl may be substituted by a substituent selected from the group consisting of hydroxycarbonyl, $(C_1-C_4)$-alkoxycarbonyl and amino, $R^7$ represents hydrogen or $(C_1-C_4)$-alkyl, and either i) $R^{8A}$ and $R^{8B}$ represent hydrogen, or ii) $R^{8A}$ together with $R^{8B}$ forms an oxo group, or

[E] reacting a compound of the formula (IX)

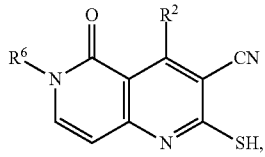

(IX)

in which $R^2$ and $R^6$ each have the meanings given in claim 1, is reacted in an inert solvent in the presence of a suitable base with a compound of the formula (VII) to give a compound of the formula (I-E)

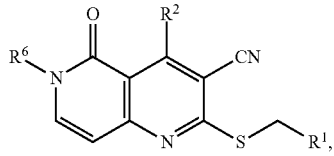

(I-E)

in which $R^1$, $R^2$ and $R^6$ each have the meanings given in claim 1, or

[F] converting a compound of the formula (IX) in an inert solvent in the presence of a suitable base with an alkyl halide into a compound of the formula (X)

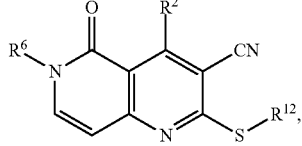

(X)

in which $R^2$ and $R^6$ each have the meanings given in claim 1, and $R^{12}$ represents $(C_1-C_4)$-alkyl, and reacting the compound of formula (X) in an inert solvent in the presence of a suitable base with a compound of the formula (VIII) to give a compound of the formula (I-F)

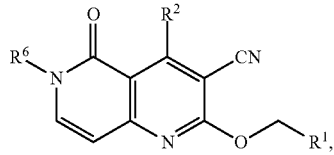

(I-F)

in which $R^1$, $R^2$ and $R^6$ each have the meanings given in claim 1, or

[G] reacting a compound of the formula (XI)

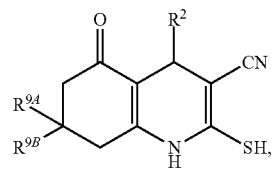

(XI)

in which $R^2$, $R^{9A}$ and $R^{9B}$ each have the meanings given in claim 1, in an inert solvent in the presence of a suitable base with a compound of the formula (VII) and optionally with addition of a suitable oxidizing agent to give a compound of the formula (I-G)

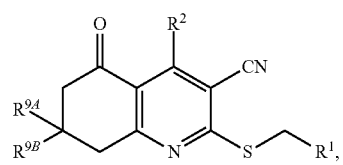

(I-G)

in which $R^1$, $R^2$, $R^{9A}$ and $R^{9B}$ each have the meanings given in claim 1, or

[H] converting a compound of the formula (XI) in an inert solvent in the presence of a suitable base with an alkyl halide into a compound of the formula (XII)

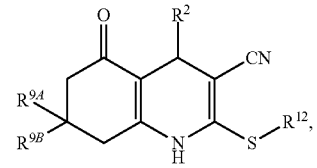

(XII)

in which $R^2$, $R^{9A}$ and $R^{9B}$ each have the meanings given in claim 1, and $R^{12}$ represents $(C_1-C_4)$-alkyl, and reacting the compound of formula (XII) in an inert solvent in the presence of a suitable base with a compound of the formula (VIII), optionally with addition of a suitable oxidizing agent to give a compound of the formula (I-H)

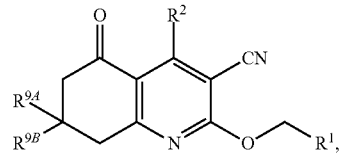

(I-H)

in which $R^1$, $R^2$, $R^{9A}$ and $R^{9B}$ each have the meanings given in claim 1, any protective groups present are then cleaved off and the resulting compounds of the formulae (I-A), (I-B), (I-C), (I-D), (I-E), (I-F), (I-G) and (I-H) are optionally converted with the appropriate (i) solvents and/or (ii) bases or acids into their salts.

6. A medicament comprising a compound of the formula (I) as defined in claim 1 in combination with an inert nontoxic pharmaceutically suitable auxiliary.

7. A medicament comprising a compound of the formula (I) as defined in claim 1 in combination with one or more further active ingredients selected from the group consisting of lipid metabolism-altering active ingredients, antidiabetics, antihypertensive drugs and antithrombotic drugs.

8. A method for the treatment of coronary heart disease, acute coronary syndrome, angina pectoris, heart failure, myocardial infarction, atrial fibrillation and hypertension in humans and animals comprising the step of administering an effective amount of at least one compound of the formula (I) as defined in claim 1.

9. A method for the treatment of diabetes, metabolic syndrome and dyslipidemias in humans and animals comprising the step of administering an effective amount of at least one compound of the formula (I) as defined in claim 1.

\* \* \* \* \*